(12) United States Patent
Du Prez et al.

(10) Patent No.: US 10,246,548 B2
(45) Date of Patent: Apr. 2, 2019

(54) COMPOSITIONS COMPRISING A POLYMERIC NETWORK

(71) Applicants: UNIVERSITEIT GENT, Ghent (BE); ECOLE SUPÉRIEURE DE PHYSIQUE ET DE CHIMIE INDUSTRIELLES DE LA VILLE DE PARIS, Paris (FR); CENTRE NATIONAL DE LA RECHERCHE SCIENTIFIQUE—CNRS, Paris (FR)

(72) Inventors: Filip Du Prez, Ghent (BE); Johan Winne, Melle (BE); Wim Denissen, Ghent (BE); Ludwik Leibler, Paris (FR); Renaud Nicolaÿ, Verrières-le-Buisson (FR)

(73) Assignees: UNIVERSITEIT GENT (BE); ECOLE SUPÉRIEURE DE PHYSIQUE ET DE CHIMIE INDUSTRIELLES DE LA VILLE DE PARIS (FR); CENTRE NATIONAL DE LA RECHERCHE SCIENTIFIQUE—CNRS (FR)

(*) Notice: Subject to any disclaimer, the term of this patent is extended or adjusted under 35 U.S.C. 154(b) by 0 days.

(21) Appl. No.: 15/533,648

(22) PCT Filed: Dec. 17, 2015

(86) PCT No.: PCT/EP2015/080259
§ 371 (c)(1),
(2) Date: Jun. 6, 2017

(87) PCT Pub. No.: WO2016/097169
PCT Pub. Date: Jun. 23, 2016

(65) Prior Publication Data
US 2017/0327625 A1    Nov. 16, 2017

(30) Foreign Application Priority Data
Dec. 19, 2014 (EP) .................................... 14290398

(51) Int. Cl.
*C08G 63/02* (2006.01)
*C08G 18/67* (2006.01)
(Continued)

(52) U.S. Cl.
CPC ........ *C08G 18/675* (2013.01); *B29B 17/0042* (2013.01); *B29B 17/0404* (2013.01);
(Continued)

(58) Field of Classification Search
USPC .............. 528/502 R; 523/400, 533; 264/106
See application file for complete search history.

(56) References Cited

U.S. PATENT DOCUMENTS

| 4,131,731 A | 12/1978 | Lai et al. |
| 2014/0088223 A1 | 3/2014 | Leibler et al. |

FOREIGN PATENT DOCUMENTS

EP    2 740 755 A1    6/2014

OTHER PUBLICATIONS

Ana Sanchez-Sanchez et al: "pH-responsive single-chain polymer nanoparticles utilizing dynamic covalent enamine bonds", Chemical Communications, vol. 50, No. 15, Jan. 1, 2014 (Jan. 1, 2014), p. 1871. (Year: 2014).*
(Continued)

*Primary Examiner* — Terressa Boykin
(74) *Attorney, Agent, or Firm* — Lathrop Gage LLP; James H. Velema, Esq.

(57) ABSTRACT

The present invention relates to a composition comprising a polymeric network having at least one unit of formula (I), (II), and/or (III);

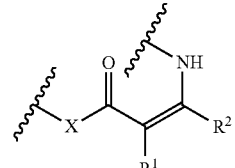

(I)

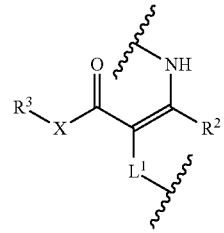

(II)

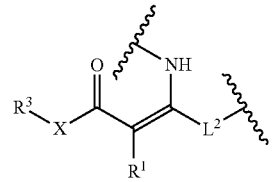

(III)

wherein the composition is obtained by contacting at least one compound A comprising at least two functions selected from the group of function of formula —X—C(=O)—CHR1-C(=O)—$R^2$, —C(=O)—C≡C—$R^2$; or —C(=O)—$CR^1$=$CR^2$—$NR^4R^5$; wherein at least 25% by weight of compounds A have a functionality ≤5, with % by weight relative to the total weight of compounds A; with at least one compound B comprising at least one —$NH_2$, or
(Continued)

—$NH_3^+$ groups; wherein X, $R^1$, $R^2$, $R^3$, $R^4$, $R^5$, $L^1$ and $L^2$ have the same meaning as that defined in the claims. The present invention also relates to a compound comprising at least two units and at most 5 units of formula (I), (II), and/or (III), described hereinabove. The present invention also relates to processes for preparing the composition and the compounds, to material, articles, and polymers comprising or using the compositions and compounds, and the use thereof.

18 Claims, 11 Drawing Sheets

(51) Int. Cl.
*C08G 83/00* (2006.01)
*C08J 3/24* (2006.01)
*C08J 11/04* (2006.01)
*B29B 17/00* (2006.01)
*B29B 17/04* (2006.01)
*C07C 225/16* (2006.01)
*C07C 229/30* (2006.01)
*C07D 295/185* (2006.01)
*C08G 18/72* (2006.01)
*C08J 11/06* (2006.01)

(52) U.S. Cl.
CPC .......... *C07C 225/16* (2013.01); *C07C 229/30* (2013.01); *C07D 295/185* (2013.01); *C08G 18/72* (2013.01); *C08G 83/008* (2013.01); *C08J 3/247* (2013.01); *C08J 11/04* (2013.01); *C08J 11/06* (2013.01); *C08J 2375/14* (2013.01); *Y02P 20/143* (2015.11); *Y02W 30/62* (2015.05); *Y02W 30/625* (2015.05); *Y02W 30/70* (2015.05)

(56) References Cited

OTHER PUBLICATIONS

Amamoto et al. (2011) "Repeatable photoinduced self-healing of covalently cross-linked polymers through reshuffling of trithiocarbonate units," Angew. Chem. Int. Ed. 50(7):1660-1663.
Bowman et al. (Mar. 2, 2012) "Covalent adaptable networks: reversible bond structures incorporated in polymer networks," Angew. Chem. Int. Ed. 51:4272-4274.
Brutman et al. (Jun. 12, 2014) "Polylactide Vitrimers," ACS Macro Letters. 3(7):607-610.
Capelot et al. (Jun. 11, 2012) "Catalytic Control of the Vitrimer Glass Transition," ACS Macro Letters. 1(7):789-792.
Capelot et al. (Apr. 26, 2012) "Metal-Catalyzed Transesterification for Healing and Assembling of Thermosets," J. Am. Chem. Soc. 134(18):7664-7667.
Chen (2002) "A thermally re-mendable cross-linked polymeric material," Science. 295(5560):1698-1702.
Clemens (1985) "Acetoacetylation with 2,2,6-trimethyl-4H-1,3-dioxin-4-one: a convenient alternative to diketene," The Journal of Organic Chemistry. 50(14):2431-2435.
Crespy et al. (2008) "100 years of bakelite, the material of a 1000 uses," Angew. Chem. Int. Ed. 47(18):3322-3328.
Gaylord et al. (1961) "Book Reviews: Preparative Methods of Polymer Chemistry," Journal of Polymer Science. 51:S77.
Kloxin et al. (2010) "Covalent Adaptable Networks (CANs): A Unique Paradigm in Cross-Linked Polymers," Macromolecules. 43(6):2643-2653.
Kloxin et al. (Apr. 12, 2013) "Covalent adaptable networks: smart, reconfigurable and responsive network systems," Chem. Soc. Rev. 42:7161-7173.
Lei et al. (Feb. 20, 2014) "Room-Temperature Self-Healable and Remoldable Cross-linked Polymer Based on the Dynamic Exchange of Disulfide Bonds," Chem. Mater. 26(6):2038-2046.
Lu et al. (May 8, 2012) "Making Insoluble Polymer Networks Malleable via Olefin Metathesis," J. Am. Chem. Soc. 134 (20):8424-8427.
Lu et al. (Aug. 6, 2012) "Olefin Metathesis for Effective Polymer Healing via Dynamic Exchange of Strong Carbon—Carbon Double Bonds," J. Am. Chem. Soc. 134(34):14226-14231.
Montarnal et al. (2011) "Silica-Like Malleable Materials from Permanent Organic Networks," Science. 334 (6058):965-968.
Nicolay et al. (2010) "Responsive Gels Based on a Dynamic Covalent Trithiocarbonate Cross-Linker," Macromolecules. 43(9):4355-4361.
Rekondo et al. (Sep. 13, 2013) "Catalyst-free room-temperature self-healing elastomers based on aromatic disulfide metathesis," Materials Horizons. 2014(1):237-240.
Sanchez-Sanchez et al. (Jan. 1, 2014) "pH-responsive single-chain polymer nanoparticles utilising dynamic covalent enamine bonds," Chem. Commun. 50(15):1871-1874.
Scott et al. (2005) "Photoinduced plasticity in cross-linked polymers," Science. 308(5728):1615-1617.
Trumbo (1991) "Michael addition polymers from bisacetoacetates," Polymer Bulletin. 26(5):481-485.
Witzeman et al. (1991) "Transacetoacetylation with tert-butyl acetoacetate: synthetic applications," The Journal of Organic Chemistry. 56:1713-1718.
International Search Report with Written Opinion corresponding to International Patent Application No. PCT/EP2015/080259, dated Feb. 16, 2016.

\* cited by examiner

COMPOSITIONS COMPRISING A POLYMERIC NETWORK

RELATED APPLICATIONS

This application is a 35 U.S.C. § 371 filing of International Application No. PCT/EP2015/080259, filed Dec. 17, 2015, which claims priority to European Patent Application No. 14290398.8, filed Dec. 19, 2014, each of which is incorporated herein by reference in its entirety.

FIELD OF THE INVENTION

The invention relates to compositions, preferably compositions comprising a permanent polymer network with chemical crosslinks, said compositions being able to be hot-fashioned. The present invention also relates to a process for manufacturing these compositions, to articles comprising these compositions and to processes for reshaping/recycling and/or healing these articles.

BACKGROUND OF THE INVENTION

Polymer materials are classically subdivided in two main classes, thermosets and thermoplastics, according to their thermal behavior. The first synthetic thermosets for practical applications were invented in 1907 by Leo Baekeland by the combination of formaldehyde and phenol. The resulting highly cross-linked network gave a rigid material that does not soften when heated, and due to its versatility it was also called "the material of a thousand uses" (D. Crespy, M. Bozonnet, M. Meier, Angew. Chem. Int. Ed. 2008, 47, 3322). Today, thermosets are used for many demanding applications because of their dimensional stability, creep resistance, chemical resistance and stiffness. Because of their molecular architecture, thermosets cannot be reshaped, processed or recycled after full curing. In contrast, thermoplastics can flow upon heating enabling multiple and easy processing, such as extrusion (N. G. Gaylord, J. R. Van Wazer, Journal of Polymer Science 1961, 51, S77), as well as recycling in many cases (M. Biron, *Thermoplastics and Thermoplastic Composites: Technical Information for Plastics Users*, Elsevier Science, 2007). Designing polymer systems which would combine the benefits of traditional thermosets with the 'plastic' properties that facilitate processing is therefore a challenge that has recently attracted great interest.

A way to make the combination of these properties is offered by the introduction of exchangeable chemical bonds into a polymer network, leading to dynamic cross-links. These bonds should be able to rearrange themselves in a reversible manner, providing on a molecular level a mechanism for macroscopic flow without risking structural damage. Polymer networks containing such exchangeable bonds, also known as covalent adaptable networks or CAN's (a) C. J. Kloxin et al., Macromolecules 2010, 43, 2643; b) C. N. Bowman, C. J. Kloxin, Angew. Chem. Int. Ed. 2012, 51, 4272; c) C. J. Kloxin, C. N. Bowman, Chem. Soc. Rev. 2013, 42), may be further classified into two groups: those relying on dissociative exchange reactions and those relying on associative exchange reactions (a) T. F. Scott, et al., Science 2005, 308, 1615; b) R. Nicolaÿ et al., Macromolecules 2010, 43, 4355; c) Y. Amamoto, et al., Angew. Chem. Int. Ed. 2011, 50, 1660).

The most common 'dissociative' group of CAN's relies on a simple reversible covalent bond formation between two groups attached to the polymer chains. By triggering the reversed bond forming step (bond dissociation) the material can achieve topology rearrangements (stress relaxation and flow) simply because of a decrease in connectivity during the temporary depolymerization, resulting in a strong and sudden viscosity drop. Such systems will always present a sol/gel transition and can thus be solubilized in the presence of solvent. A well-known example of a thermally triggered dissociative CAN relies on the well-known reversible Diels-Alder reaction between furans and maleimides (X. Chen, Science 2002, 295, 1698).

A less common type of CAN's makes use of associative bond exchanges between polymer chains, in which the cross-links between polymer chains are only broken once another bond to another (part of the) polymer chain has been formed. As a result, such systems can change their topology with no loss of connectivity during the dynamic reorganization process, making such networks effectively permanent and insoluble even at (very) high temperatures. Interestingly, as with all chemical reactions, the rate of this associative exchange increases with the temperature, leading to an Arrhenius-like viscosity dependence rather than a sudden and marked viscosity drop at the sol/gel transition. Thermally triggered associative CANs have been coined vitrimers, (M. Capelot et al., J. Am. Chem. Soc. 2012, 134, 7664.) because of their unique combination of insolubility and gradual thermal viscosity behavior which makes these permanent polymer networks processable just like glass.

In 2011, Leibler and co-workers introduced and demonstrated the unique properties of vitrimer materials using simple transesterification chemistry in an epoxy-based resin, cross-linked with polycarboxylic acids. Addition of a mild Lewis acid catalyst like zinc acetate to these classical resins resulted in an insoluble material which combined great mechanical properties, like classical hard epoxy resins, with the ability to be reshaped and reprocessed after full curing (D. Montarnal et al., Science 2011, 334, 965; b) M. Capelot et al., ACS Macro Letters 2012, 1, 789).

Since then, several other systems have been explored as possible vitrimer materials. Altuna and co-workers were able to produce citric acid-based polyester networks capable of some stress-relaxation even in the absence of a catalyst (internally catalyzed by unreacted carboxylic acids) (F. I. Altuna, V. Pettarin, R. Williams, Green Chemistry 2013).

Other polyester network and catalyst combinations have also been explored. (J. P. Brutman et al., ACS Macro Letters 2014, 607). Vitrimer(-like) materials have also been reported based on olefin or disulphide methathesis reactions (Y.-X. Lu, Z. Guan, J. Am. Chem. Soc. 2012, 134, 14226; Y.-X. Lu, et al. J. Am. Chem. Soc. 2012, 134, 8424; A. Rekondo, et al., Materials Horizons 2013; Z. Q. Lei, et al., Chem. Mater. 2014, 26, 2038).

Although different chemistries for vitrimer materials have been explored, the reported materials all have relatively low Tg's (<57° C.) and their mechanical properties are often not comparable to those of commercial resins.

There is therefore a need to develop materials having the property of being able to be heated to temperatures such that they become fashionable without suffering destruction or degradation of their structure.

SUMMARY OF THE INVENTION

According to the present invention, the present compositions are endowed with chemical reversibility, which, when combined with a mechanical constraint, may be used to give an article a new shape. The present inventors have prepared composition comprising polymeric networks which combined great mechanical properties and a suitable glass transition temperature with the ability to flow at elevated temperatures while retaining its insolubility. In some preferred embodiments, the composition comprises a polymeric network made of vinylogous-urethane, vinylogous-amide, or vinylogous-urea units. Vinylogous urethanes are compounds containing the chemical functionality —N—C=C—C(=O)—O—. Vinylogous urea are compounds containing the chemical functionality —N—C=C—C(=O)—NR—. Vinylogous amide are compounds containing the chemical functionality —N—C=C—C(=O)—CR$_2$—.

According to a first aspect of the present invention, a composition is provided, said composition comprising a polymeric network having at least one unit of formula (I), (II), and/or (III),

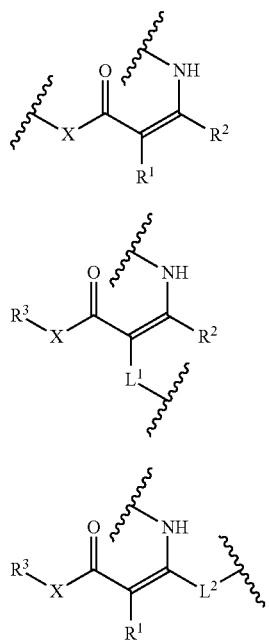

wherein said composition is obtained by contacting:
at least one compound A comprising at least two functions selected from the group of function of formula —X—C(=O)—CHR$^1$—C(=O)—R$^2$, —C(=O)—C≡C—R$^2$; or —C(=O)—CR$^1$=CR$^2$—NR$^4$R$^5$; wherein at least 25% by weight of compound A has a functionality ≤5, with % by weight relative to the total weight of compounds A;
with at least one compound B comprising at least one —NH$_2$, or —NH$_3^+$ groups, or at least one functional group that generates —NH$_2$ or —NH$_3^+$ in situ, such as —N=C=O;
wherein the ratio R=(sum(functionality of compound A×number of moles of compound A))/(sum(functionality of compound B×number of moles of all compound B)) is <1;

$$\frac{\sum f_a N_a}{\sum f_b N_b} = R < 1$$

wherein $f_a N_a$ denotes the number of moles of —X—C(=O)—CHR$^1$—C(=O)—R$^2$, —C(=O)—C≡C—R$^2$; or —C(=O)—CR$^1$=CR$^2$—NR$^4$R$^5$ functions of the at least one compound A, and $f_b N_b$ denotes the number of moles of —NH$_2$, and/or —NH$_3^+$ groups or the number of moles of functional groups which could generate —NH$_2$ or NH$_3^+$ in situ, such as —N=C=O, of the at least one compound B;

R$^1$ is hydrogen or is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkyl C$_{1-20}$alkyl; heteroC$_{1-20}$alkyl; heterocyclyl; heterocyclylC$_{1-20}$alkyl; heteroaryl; and heteroarylC$_{1-20}$alkyl;
wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;
wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkyl C$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;
wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^1$; each Z$^1$ is independently selected from the group consisting of halogen; C$_{1-20}$alkyl; C$_{2-20}$alkenyl; C$_{2-20}$alkynyl; C$_{6-12}$aryl, C$_{3-8}$cycloalkyl, C$_{6-12}$arylC$_{1-20}$alkyl, hetero C$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$; and R$^4$ is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkylC$_{1-20}$alkyl; heteroC$_{1-20}$alkyl; heterocyclyl; heterocyclylC$_{1-20}$alkyl; heteroaryl; and heteroarylC$_{1-20}$alkyl;
wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;
wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkyl C$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;
wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^4$; each Z$^4$ is independently selected from the group consisting of

5

$NR^{11}R^{12}$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl $C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; cyano; —$CO_2R^{10}$; —$C(O)NR^{11}R^{12}$; and —$C(O)R^9$;

or wherein the ratio R=(sum(functionality of compound A×number of moles of compound A))/(sum(functionality of compound A×number of moles of compound A)+sum(functionality of compound B×number of moles of all compound B)) is <1;

$$\frac{\sum f_a N_a}{\sum f_a N_a + \sum f_b N_b} = R < 1$$

when $R^1$ and $R^4$ together with the atom to which they are attached form a 5-, 6-, or 7-membered heterocyclyl or heteroaryl; wherein each of said heterocyclyl; or heteroaryl; can be unsubstituted or substituted with one or more $Z^5$; each $Z^5$ is independently selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halogen; halo$C_{1-20}$alkyl; halo$C_{1-20}$alkyloxy; —$OR^{10}$; —$SR^{10}$; —$S(O)_2R^9$; —$S(O)R^9$; —$SO_2NR^{11}R^{12}$; —$NR^{10}C(O)R^9$; —$NR^{10}S(O)_2R^9$; —$NR^{10}C(O)NR^{11}R^{12}$; —$NR^{11}R^{12}$; nitro; cyano; —$CO_2R^{10}$; —$C(O)NR^{11}R^{12}$; and —$C(O)R^9$;

wherein $f_a N_a$ denotes the number of moles of —X—C(=O)—$CHR^1$—C(=O)—$R^2$, —C(=O)—C≡C—$R^2$; or C(=O)—$CR^1$=$CR^2$—$NR^4R^5$ functions of the at least one compound A, and $f_b N_b$ denotes the number of moles of —$NH_2$, and/or —$NH_3^+$ groups or the number of moles of functional groups which could generate —$NH_2$ or $NH_3^+$ in situ, such as —N=C=O, of the at least one compound B;

and wherein X is selected from O, $NR^{13}$, or $CR^{14}R^{15}$; or X and $R^3$ together form a group $R^6$, wherein $R^6$ is selected from the group consisting of $C_{6-12}$aryl, heteroaryl or heterocyclyl; wherein said $C_{6-12}$aryl, heteroaryl or heterocyclyl can be unsubstituted or substituted with one or more $Z^{31}$; and $Z^{31}$ is independently selected from the group consisting of —X—C(=O)—$CHR^1$—C(=O)—$R^2$, —C(=O)—$CR^1$=$CR^2$—$NR^4R^5$; or —C(=O)—C≡C—$R^2$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$; or $R^3$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$_{1-20}$alkyl; $C_{1-20}$alkyl$C_{3-8}$cycloalkyl$C_{1-20}$alkyl; $C_{3-8}$cycloalkyl $C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl $C_{1-20}$alkyl; $C_{1-20}$alkylheterocyclyl$C_{1-20}$alkyl; heteroaryl; and heteroaryl$C_{1-20}$alkyl;

6 wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; $C_{1-20}$alkylheterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl$C_{1-20}$alkyl; $C_{1-20}$alkylheterocyclyl$C_{1-20}$alkyl; heteroaryl; and heteroaryl $C_{1-20}$alkyl; can be oxidized to form at least one C=O, C=S, N=O, N=S, S=O or $S(O)_2$;

wherein said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; hetero $C_{1-20}$alkyl; heterocyclyl; heterocyclyl$C_{1-20}$alkyl; $C_{1-20}$alkylheterocyclyl$C_{1-20}$alkyl; heteroaryl; and heteroaryl$C_{1-20}$alkyl; can be unsubstituted or substituted with one or more $Z^3$; each $Z^3$ is independently selected from the group consisting of —X—C(=O)—$CHR^1$—C(=O)—$R^2$, —C(=O)—C≡C—$R^2$; or —C(=O)—$CR^1$=$CR^2$—$NR^4R^5$; halogen; $C_{1-20}$alkyl; halo$C_{1-20}$alkyl; halo$C_{1-20}$alkyloxy; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$L^1$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene;

wherein said $C_{1-20}$alkylene, $C_{2-20}$alkenylene, $C_{2-20}$alkynylene, $C_{3-8}$cycloalkylene$C_{1-20}$alkylene; $C_{6-12}$aryl$C_{1-20}$alkylene, heterocyclylene$C_{1-20}$alkylene; and heteroarylene$C_{1-20}$alkylene, optionally comprises one or more heteroatoms in the alkylene, alkenylene, alkynylene moiety, said heteroatoms being each independently selected from O, S and N;

wherein at least one carbon atom or heteroatom of said $C_{1-20}$alkylene, $C_{2-20}$alkenylene; $C_{2-20}$alkynylene; $C_{6-12}$arylene, $C_{3-8}$cycloalkylene; $C_{6-12}$arylene $C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene; can be oxidized to form at least one C=O, C=S, N=O, N=S, S=O or $S(O)_2$;

wherein said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene $C_{1-20}$alkylene hetero$C_{1-20}$alkylene; heterocyclylene; heterocyclylene$C_{1-20}$alkylene; heteroarylene; and heteroarylene$C_{1-20}$alkylene; can be unsubstituted or substituted with one or more $Z^{21}$; each $Z^{21}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

$R^2$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or S(O)$_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^2$; each $Z^2$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

$L^2$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene;

wherein said $C_{1-20}$alkylene, $C_{2-20}$alkenylene, $C_{2-20}$alkynylene, $C_{3-8}$cycloalkylene$C_{1-20}$alkylene; $C_{6-12}$aryl$C_{1-20}$alkylene, heterocyclylene$C_{1-20}$alkylene; and heteroarylene$C_{1-20}$alkylene, optionally comprises one or more heteroatoms in the alkylene, alkenylene, alkynylene moiety, said heteroatoms being each independently selected from O, S and N;

wherein at least one carbon atom or heteroatom of said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene; can be oxidized to form at least one C=O, C=S, N=O, N=S, S=O or S(O)$_2$;

wherein said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene; can be unsubstituted or substituted with one or more $Z^{22}$; each $Z^{22}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

or wherein $R^2$ and $R^4$ together with the atom to which they are attached form a 5-, 6-, or 7-membered heterocyclyl or heteroaryl; wherein each of said heterocyclyl; or heteroaryl; can be unsubstituted or substituted with one or more $Z^6$; each $Z^6$ is independently selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halogen; halo$C_{1-20}$alkyl; halo$C_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

$R^5$ is hydrogen or is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or S(O)$_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^7$; each $Z^7$ is independently selected from the group consisting of NR$^{11}$R$^{12}$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; cyano; —CO$_2$R$^{10}$; —C(O)NR$^{11}$R$^{12}$; and —C(O)R$^9$;

each $R^9$ is independently selected from hydroxyl; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$ alkyl; heterocyclyl; heteroaryl; heterocyclyl $C_{1-20}$alkyl; and heteroaryl$C_{1-20}$alkyl; can be oxidized to form at least one C=O, C=S, N=O, N=S, S=O or $S(O)_2$;

each $R^{10}$ is independently selected from the group consisting of hydrogen, $C_{1-20}$alkyl, $C_{2-20}$alkenyl, $C_{2-20}$alkynyl, $C_{6-12}$aryl, $C_{3-8}$cycloalkyl, $C_{6-12}$aryl $C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl $C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

or wherein $R^{11}$ and $R^{12}$ together with the atom to which they are attached form a 5-, 6-, or 7-membered heterocyclyl;

$R^{13}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

$R^{14}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

$R^{15}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$.

According to a second aspect of the present invention, a compound is provided comprising at least two units and at most 5 units of formula (I), (II), and/or (III);

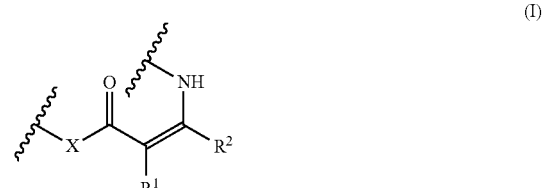

(I)

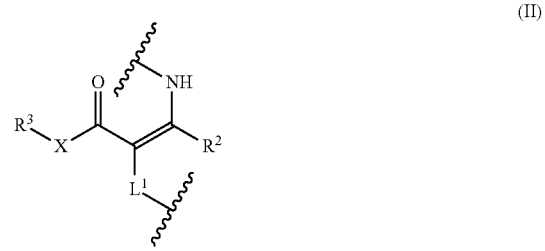

(II)

-continued

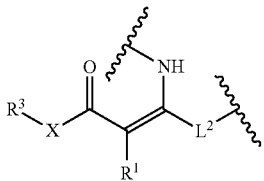
(III)

wherein $R^1$ is hydrogen or is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;
- wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;
- wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or $S(O)^2$;
- wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^1$; each $Z^1$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$; and X is selected from O, $NR^{13}$, or $CR^{14}R^{15}$; or X and $R^3$ together form a group $R^6$, wherein $R^6$ is selected from the group consisting of $C_{6-12}$aryl, heteroaryl or heterocyclyl; wherein said $C_{6-12}$aryl, heteroaryl or heterocyclyl can be unsubstituted or substituted with one or more $Z^{31}$; and $Z^{31}$ is independently selected from the group consisting of —C(=O)—C≡C—$R^2$; —X—C(=O)—CHR$^1$—C(=O)—$R^2$, or —C(=O)—CR$^1$=CR$^2$—NR$^4$R$^5$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl $C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$; or $R^3$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$_{1-20}$alkyl; $C_{1-20}$alkyl$C_{3-8}$cycloalkyl$C_{1-20}$alkyl; $C_{3-8}$cycloalkyl $C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl$C_{1-20}$alkyl; $C_{1-20}$alkylheterocyclyl$C_{1-20}$alkyl; heteroaryl; and heteroaryl$C_{1-20}$alkyl;
- wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; $C_{1-20}$alkyl$C_{3-8}$cycloalkyl $C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; $C_{1-20}$alkylheterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;
- wherein at least one carbon atom or heteroatom of said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$_{1-20}$alkyl; $C_{1-20}$alkyl$C_{3-8}$cycloalkyl $C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl$C_{1-20}$alkyl; $C_{1-20}$alkylheterocyclyl$C_{1-20}$alkyl; heteroaryl; and heteroaryl $C_{1-20}$alkyl; can be oxidized to form at least one C=O, C=S, N=O, N=S, S=O or $S(O)_2$;
- wherein said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl $C_{1-20}$alkyl; $C_{1-20}$alkylheterocyclyl$C_{1-20}$alkyl; heteroaryl; and heteroaryl$C_{1-20}$alkyl; can be unsubstituted or substituted with one or more $Z^3$; each $Z^3$ is independently selected from the group consisting of —X—C(=O)—CHR$^1$—C(=O)—$R^2$, —C(=O)—C≡C—$R^2$; or —C(=O)—CR$^1$=CR$^2$—NR$^4$R$^5$; halogen; $C_{1-20}$alkyl; halo$C_{1-20}$alkyl; halo$C_{1-20}$alkyloxy; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$L^1$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene;
- wherein said $C_{1-20}$alkylene, $C_{2-20}$alkenylene, $C_{2-20}$alkynylene, $C_{3-8}$cycloalkylene$C_{1-20}$alkylene; $C_{6-12}$aryl$C_{1-20}$alkylene, heterocyclylene$C_{1-20}$alkylene; and heteroarylene$C_{1-20}$alkylene, optionally comprises one or more heteroatoms in the alkylene, alkenylene, alkynylene moiety, said heteroatoms being each independently selected from O, S and N;
- wherein at least one carbon atom or heteroatom of said $C_{1-20}$alkylene, $C_{2-20}$alkenylene; $C_{2-20}$alkynylene; $C_{6-12}$arylene, $C_{3-8}$cycloalkylene; $C_{6-12}$arylene $C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene; can be oxidized to form at least one C=O, C=S, N=O, N=S, S=O or $S(O)_2$;

wherein said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; heteroC$_{1-20}$alkylene; heterocyclylene; heteroarylene; and heteroarylene$C_{1-20}$alkylene; can be unsubstituted or substituted with one or more $Z^{21}$; each $Z^{21}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl $C_{1-20}$alkyl, heteroC$_{1-20}$alkyl; heterocyclyl; heteroaryl; $C_{3-8}$cycloalkyl$C_{1-20}$alkyl; heterocyclyl $C_{1-20}$alkyl; heteroaryl$C_{1-20}$alkyl; haloC$_{1-20}$alkyl; haloC$_{1-20}$alkyloxy; —OR$^{10}$; —SR$^{10}$; —S(O)R$^{9}$; —S(O)$_{2}$R$^{9}$; —SO$_{2}$NR$^{11}$R$^{12}$; nitro; —NR$^{10}$C(O)R$^{9}$; —NR$^{10}$S(O)$_{2}$R$^{9}$; —NR$^{10}$C(O)NR$^{11}$R$^{12}$; NR$^{11}$R$^{12}$; cyano; —CO$_{2}$R$^{10}$; —C(O)NR$^{11}$R$^{12}$; and —C(O)R$^{9}$;

$R^{2}$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; heteroC$_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N; wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or S(O)$_{2}$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^{2}$; each $Z^{2}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl $C_{1-20}$alkyl; heterocyclyl$C_{1-20}$alkyl; heteroaryl $C_{1-20}$alkyl; haloC$_{1-20}$alkyl; haloC$_{1-20}$alkyloxy; —OR$^{10}$; —SR$^{10}$; —S(O)R$^{9}$; —S(O)$_{2}$R$^{9}$; —SO$_{2}$NR$^{11}$R$^{12}$; nitro; —NR$^{10}$C(O)R$^{9}$; —NR$^{10}$S(O)$_{2}$R$^{9}$; —NR$^{10}$C(O)NR$^{11}$R$^{12}$; NR$^{11}$R$^{12}$; cyano; —CO$_{2}$R$^{10}$; —C(O)NR$^{11}$R$^{12}$; and —C(O)R$^{9}$;

$L^{2}$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$arylene $C_{1-20}$alkylene; $C_{3-8}$cycloalkylene$C_{1-20}$alkylene; heteroC$_{1-20}$alkylene; heterocyclylene; heterocyclylene$C_{1-20}$alkylene; heteroarylene; and heteroarylene$C_{1-20}$alkylene;

wherein said $C_{1-20}$alkylene, $C_{2-20}$alkenylene, $C_{2-20}$alkynylene, $C_{3-8}$cycloalkylene$C_{1-20}$alkylene; $C_{6-12}$aryl$C_{1-20}$alkylene, heterocyclylene$C_{1-20}$alkylene; and heteroarylene$C_{1-20}$alkylene, optionally comprises one or more heteroatoms in the alkylene, alkenylene, alkynylene moiety, said heteroatoms being each independently selected from O, S and N; wherein at least one carbon atom or heteroatom of said $C_{1-20}$alkylene, $C_{2-20}$alkenylene, $C_{2-20}$alkynylene; $C_{6-12}$arylene, $C_{3-8}$cycloalkylene; $C_{6-12}$arylene $C_{1-20}$alkylene; $C_{3-8}$cycloalkylene$C_{1-20}$alkylene; heteroC$_{1-20}$alkylene; heterocyclylene; heterocyclylene$C_{1-20}$alkylene; heteroarylene; and heteroarylene$C_{1-20}$alkylene; can be oxidized to form at least one C=O, C=S, N=O, N=S, S=O or S(O)$_{2}$;

wherein said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$ alkylene; heteroC$_{1-20}$alkylene; heterocyclylene; heterocyclylene$C_{1-20}$alkylene; heteroarylene; and heteroarylene$C_{1-20}$alkylene; can be unsubstituted or substituted with one or more $Z^{22}$; each $Z^{22}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; haloC$_{1-20}$alkyl; haloC$_{1-20}$alkyloxy; —OR$^{10}$; —SR$^{10}$; —S(O)R$^{9}$; —S(O)$_{2}$R$^{9}$; —SO$_{2}$NR$^{11}$R$^{12}$; nitro; —NR$^{10}$C(O)R$^{9}$; —NR$^{10}$S(O)$_{2}$R$^{9}$; —NR$^{10}$C(O)NR$^{11}$R$^{12}$; NR$^{11}$R$^{12}$; cyano; —CO$_{2}$R$^{10}$; —C(O)NR$^{11}$R$^{12}$; and —C(O)R$^{9}$;

$R^{4}$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; heteroC$_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N; wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or S(O)$_{2}$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^{4}$; each $Z^{4}$ is independently selected from the group consisting of NR$^{11}$R$^{12}$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl $C_{1-20}$alkyl, heteroC$_{1-20}$alkyl; heterocyclyl; heteroaryl; $C_{3-8}$cycloalkyl$C_{1-20}$alkyl; heterocyclyl $C_{1-20}$alkyl; heteroaryl$C_{1-20}$alkyl; haloC$_{1-20}$alkyl; haloC$_{1-20}$alkyloxy; —OR$^{10}$; —SR$^{10}$; —S(O)R$^{9}$; —S(O)$_{2}$R$^{9}$; —SO$_{2}$NR$^{11}$R$^{12}$; nitro; —NR$^{10}$C(O)R$^{9}$; —NR$^{10}$S(O)$_{2}$R$^{9}$; —NR$^{10}$C(O)NR$^{11}$R$^{12}$; cyano; —CO$_{2}$R$^{10}$; —C(O)NR$^{11}$R$^{12}$; and —C(O)R$^{9}$;

or $R^{1}$ and $R^{4}$ together with the atom to which they are attached form a 5-, 6-, or 7-membered heterocyclyl or heteroaryl; wherein each of said heterocyclyl; or heteroaryl; can be unsubstituted or substituted with one or more $Z^{5}$; each $Z^{5}$ is independently selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl;

heteroarylC$_{1-20}$alkyl; halogen; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

R$^5$ is hydrogen or is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkyl C$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;

wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^7$; each Z$^7$ is independently selected from the group consisting of NR$^{11}$R$^{12}$; halogen; C$_{1-20}$alkyl; C$_{2-20}$alkenyl, C$_{2-20}$alkynyl, C$_{6-12}$aryl, C$_{3-8}$cycloalkyl, C$_{6-12}$aryl C$_{1-20}$alkyl, heteroC$_{1-20}$alkyl; heterocyclyl; heteroaryl; C$_{3-8}$cycloalkylC$_{1-20}$alkyl; heterocyclyl C$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; cyano; —CO$_2$R$^{10}$; —C(O)NR$^{11}$R$^{12}$; and —C(O)R$^9$;

each R$^9$ is independently selected from hydroxyl; C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

each R$^{10}$ is independently selected from the group consisting of hydrogen, C$_{1-20}$alkyl, C$_{2-20}$alkenyl, C$_{2-20}$alkynyl, C$_{6-12}$aryl, C$_{3-8}$cycloalkyl, C$_{6-12}$aryl C$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

each R$^{11}$ and R$^{12}$ is independently selected from the group consisting of hydrogen; C$_{1-20}$alkyl, C$_{2-20}$alkenyl, C$_{2-20}$alkynyl, C$_{6-12}$aryl, C$_{3-8}$cycloalkyl, C$_{6-12}$aryl C$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

or wherein R$^{11}$ and R$^{12}$ together with the atom to which they are attached form a 5-, 6-, or 7-membered heterocyclyl;

R$^{13}$ is hydrogen or is selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

R$^{14}$ is hydrogen or is selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

R$^{15}$ is hydrogen or is selected from the group consisting of C$_{1-20}$alkyl, C$_{2-20}$alkenyl, C$_{2-20}$alkynyl, C$_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)^2$.

According to a third aspect of the present invention, a process is provided for preparing a composition according to the first aspect, or a compound according to the second aspect, wherein said process comprises the step of contacting at least one compound A comprising at least two functions selected from the group of function of formula —X—C(=O)—CHR$^1$—C(=O)—R$^2$, —C(=O)—C≡C—R$^2$; or —C(=O)—CR$^1$=CR$^2$—NR$^4$R$^5$; wherein at least 25% by weight of compounds A have a functionality ≤5, preferably ≤4, more preferably ≤3, with % by weight being relative to the total weight of compound A used;

with at least one compound B comprising at least one —NH$_2$, or —NH$_3^+$ groups, or at least one functional group that generates —NH$_2$ or NH$_3^+$ in situ, such as —N=C=O, wherein $$\frac{\sum f_a N_a}{\sum f_b N_b} = R < 1;$$

or wherein $$\frac{\sum f_a N_a}{\sum f_a N_a + \sum f_b N_b} = R < 1,$$

when R$^1$ and R$^4$ together with the atom to which they are attached form a 5-, 6-, or 7-membered heterocyclyl or heteroaryl; and
wherein X, R$^2$, and R$^5$ have the same meaning as that defined herein.

The present invention also encompasses the use of a composition according to the first aspect of the invention, or the use of a compound according to the second aspect, as a reactant for preparing a polymer composition.

The present invention also encompasses a material resulting from the curing of the composition according to the first aspect, and a material resulting from a compound according to the second aspect.

The present invention also encompasses an article comprising the composition according to the first aspect, or a compound according to the second aspect or a material comprising said composition or said compound.

The present invention also encompasses processes for recycling an article comprising said composition, said compound, or a material made therefrom.

The present invention also encompasses the use of a composition according to the first aspect, or a compound according to the second aspect of the invention in polymers, membranes, adhesives, foams, sealants, molded articles, films, extruded articles, fibers, polymer based additives, varnishes, paints, coatings, inks, composite material, organic LEDs, organic semiconductors, or conducting organic polymers.

The present invention also encompasses a process for reshaping and/or repairing an article comprising a composition according to the first aspect, or a compound according to the second aspect, comprising the step of thermally treating the article at a temperature (T) above room temperature.

The present invention also encompasses the use of a compound comprising at least two units and at most 5 units of formula (I), (II), and/or (III); for the preparation of a polymeric network,

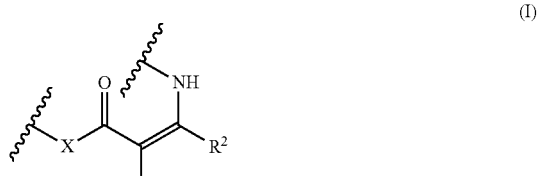

(I)

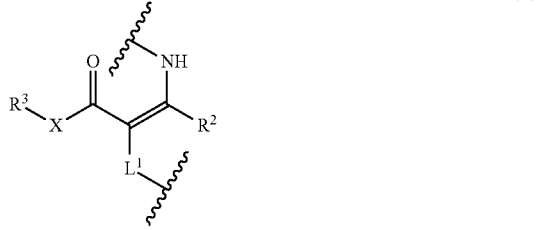

(II)

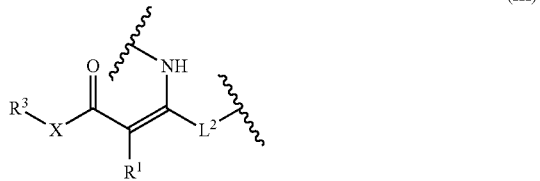

(III)

wherein X, R$^1$, R$^2$, R$^3$, L$^1$ and L$^2$ have the same meaning as that defined herein.

The compositions, compounds, and material and articles made therefrom can be reworked to any shape while being at the same time permanently cross-linked.

These compositions, and the compounds as well as the processes of the invention may thus be used in all the usual applications of thermosetting resins, but have the advantageous properties that have been mentioned above and are illustrated in detail in the description and the implementation examples. The present invention also encompasses composite materials comprising such composition, or compounds, a process for manufacturing an article or a material based on this composition or compounds, a process for transforming a resin-based article, a process for manufacturing an object with controlled transformation, a process for transforming an object with controlled transformation, a process for assembling and bonding materials and composites based on this composition or compounds, a process for repairing an article based on this composition or compounds, a process for recycling based on this composition or compounds.

The independent and dependent claims set out particular and preferred features of the invention. Features from the dependent claims may be combined with features of the independent or other dependent claims as appropriate.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION OF THE INVENTION

Figure 1:
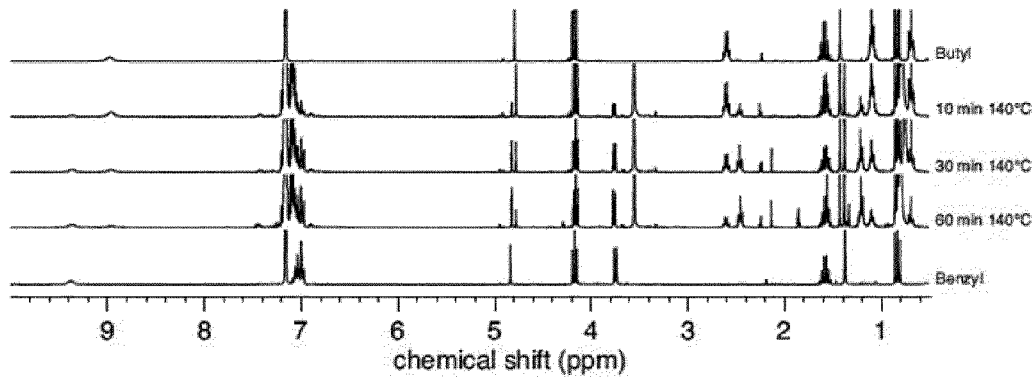
FIG. 1 represents the NMR spectra of propyl-3-(butylamino)but-2-enoate (upper), propyl-3-(benzylamino)but-2-enoate (lower) and of the mixture after 10, 30 and 60 minutes at 140° C.

When describing the invention, the terms used are to be construed in accordance with the following definitions, unless a context dictates otherwise.

As used herein, the singular forms "a", "an", and "the" include both singular and plural referents unless the context clearly dictates otherwise. By way of example, "a compound" means one compound or more than one compound.

As used herein, the term "and/or," when used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

All references cited in the present specification are hereby incorporated by reference in their entirety. In particular, the teachings of all references herein specifically referred to are incorporated by reference.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

When describing the present invention, the terms used are to be construed in accordance with the following definitions, unless a context dictates otherwise.

Whenever the term "substituted" is used herein, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation from a reaction mixture.

Where groups can be substituted, such groups may be substituted with one or more, and preferably one, two or three substituents. Substituents may be selected from but not limited to, for example, the group comprising halogen; $C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; or —$C(O)R^9$.

The terminology "optionally comprises one or more heteroatoms, said heteroatoms being selected from the atoms O, S, or N" as used herein, refers to a group where one or more carbon atoms are replaced by at least one oxygen, nitrogen or sulfur atom and thus includes, depending on the group to which is referred, heteroalkyl, heteroalkenyl, heteroalkynyl, heteroalkylene, heteroalkenylene, heteroalkynylene, cycloheteroalkyl, cycloheteroalkenyl, cycloheteroalkynyl, heteroaryl, arylheteroalkyl(ene), heteroarylalkyl(ene), heteroarylheteroalkyl(ene), arylheteroalkenyl(ene), heteroarylalkenyl(ene), heteroarylheteroalkenyl(ene), heteroarylheteroalkenyl(ene), arylheteroalkynyl(ene), heteroarylalkynyl(ene), heteroarylheteroalkynyl(ene), among others. This term therefore comprises, depending on the group to which is referred, as an example "heteroalkyl" such as alkoxy, alkoxyalkyl, mono- or di-alkylamino, mono- or di-alkylaminoalkyl, alkylthio, alkylthioalkyl; "heteroalkenyl" such as alkenyloxy, alkenyloxyalkenyl, mono- or di-alkenylamino, mono- or di-alkenylaminoalkenyl, alkenylthio, alkenylthioalkenyl, and "heteroalkynyl" such as alkynyloxy, alkynyloxyalkynyl, mono- or di-alkynylamino, mono- or di-alkynylaminoalkynyl, alkynylthio, alkynylthioalkynyl. As an example, the terminology "alkyl optionally comprises one or more heteroatoms, said heteroatoms being selected from the atoms of O, S, or N" therefore refers to heteroalkyl, meaning an alkyl which comprises one or more heteroatoms in the hydrocarbon chain, whereas the heteroatoms may be positioned at the beginning of the hydrocarbon chain, in the hydrocarbon chain or at the end of the hydrocarbon chain. Examples of heteroalkyl include alkoxy, alkoxyalkyl, alkylamino, alkylaminoalkyl, alkylthio, alkylthioalkyl, such as methoxy, methylthio, ethoxy, propoxy, $CH_3$—O—$CH_2$—, $CH_3$—S—$CH_2$—, $CH_3$—$CH_2$—O—$CH_2$—, $CH_3NH$—, $(CH_3)_2N$—, $(CH_3)_2$—$CH_2$—$NHCH_2$—$CH_2$—, among many other examples. The term "hetero$C_{1-20}$alkyl", as a group or part of a group, also encompasses groups of Formula —$X^1$—$R^f$ or —$R^e$—$X^1$—$R^f$, and $C_{1-20}$alkyl substituted with one or more groups of formula —$X^1$—$R^f$ or —$R^e$—$X^1$—$R^f$, wherein $R^e$ is as defined above for $C_{1-20}$alkylene and $X^1$ is selected from $NR^c$, S or O, and $R^c$ is selected from hydrogen, or $C_{1-20}$alkyl, and $R^f$ is selected from hydrogen, $C_{1-20}$acyl, $C_{1-20}$alkyl, or $C_{3-6}$cycloalkyl. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, and the like.

As an example, the terminology "arylalkyl optionally comprises one or more heteroatoms in the alkyl chain, said heteroatoms being selected from the atoms O, S, or N" therefore refers to aryl-heteroalkyl, meaning an arylalkyl which comprises one or more heteroatoms in the hydrocarbon chain, whereas the heteroatoms may be positioned at the beginning of the hydrocarbon chain, in the hydrocarbon chain or at the end of the hydrocarbon chain. "Aryl-heteroalkyl" thus includes aryloxy, arylalkoxy, aryl-alkyl-NH— and the like and examples are phenyloxy, benzyloxy, aryl-$CH_2$—S—$CH_2$—, aryl-$CH_1$—O—$CH_2$—, aryl-NH—$CH_2$— among many other examples.

The terminology regarding a chemical group "wherein at least one carbon atom or heteroatom of said group can be oxidized to form at least one C=O, C=S, N=O, N=S, S=O or $S(O)^2$" as used herein, refers to a group where two or more hydrogen atoms on a carbon atom or heteroatom of said group are taken together to form C=O, C=S, N=O, N=S, S=O or $S(O)^2$. As an example, the terminology refers to "an alkyl wherein a carbon atom or heteroatom of said alkyl can oxidized to form a C=O, C=S, N=O, N=S, S=O or $S(O)^{2}$", includes among other examples $CH_3$—C(O)—$CH_2$—, $CH_3$—C(O)—, $CH_3$—C(S)—$CH_2$— and $(CH_3)_2$—$CH_2$—C(O)—$CH_2$—$CH_2$—.

The combination for a group "optionally comprises one or more heteroatoms, said heteroatoms being selected from the atoms O, S, or N" and "wherein a carbon atom or heteroatom of said group can be oxidized to form a C=O, C=S, N=O, N=S, S=O or $S(O)^{2}$" can combine the two aspects described herein above and includes, if the group referred to is alkyl, among other examples $CH_3$—COO—, $CH_3$—COO—$CH_2$—, $CH_3$—NH—CO—, $CH_3$—NH—CO—$CH_2$—, $CH_3$—NH—CS—$CH_2$—, $CH_3$—NH—CS—NH—$CH_2$—, $CH_3$—NH—$S(O)^2$— and $CH_3$—NH—$S(O)^2$—NH—$CH_2$—.

The term "halo" or "halogen" as a group or part of a group is generic for fluoro, chloro, bromo, iodo.

The term "oxo" as used herein refers to the group =O.

The term "amino" refers to the group —$NH_2$.

The term "hydroxyl" or "hydroxy" as used herein refers to the group —OH.

The term "nitro" as used herein refers to the group —$NO_2$.

The term "cyano" as used herein refers to the group —CN.

The term "carboxy" or "carboxyl" or "hydroxycarbonyl" as used herein refers to the group —$CO_2H$.

The term "alkyl", as a group or part of a group, refers to a hydrocarbyl group of Formula $C_nH_{2n+1}$ wherein n is a number of at least 1. Alkyl groups may be linear, or branched and may be substituted as indicated herein. Generally, the alkyl groups comprise from 1 to 20 carbon atoms, preferably from 1 to 12 carbon atoms, preferably from 1 to 10 carbon atoms, preferably from 1 to 6 carbon atoms, more preferably 1, 2, 3, 4, 5, 6 carbon atoms. When a subscript is used herein following a carbon atom, the subscript refers to the number of carbon atoms that the named group may contain. For example, the term "$C_{1-20}$alkyl", as a group or part of a group, refers to a hydrocarbyl group of Formula $C_nH_{2n+1}$ wherein n is a number ranging from 1 to 20. Thus, for example, $C_{1-20}$alkyl groups include all linear, or branched alkyl groups having 1 to 20 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers, undecyl and its isomers, dodecyl and its isomers, tridecyl and its isomers, tetradecyl and its isomers, pentadecyl and its isomers, hexadecyl and its isomers, heptadecyl and its isomers, octadecyl and its isomers, nonadecyl and its isomers, icosyl and its isomers, and the like. For example, $C_{1-20}$alkyl includes all linear, or branched alkyl groups having 1 to 20 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers and the like, etc. For example, $C_{1-6}$alkyl includes all linear, or branched alkyl groups having 1 to 6 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers. When the suffix "ene" is used in conjunction with an alkyl group, i.e. "alkylene", this is intended to mean the alkyl group as defined herein having two single bonds as points of attachment to other groups. Non-limiting examples of alkylene groups includes methylene, ethylene, methylmethylene, propylene, ethylethylene, and 1,2-dimethylethylene. Similarly, where alkenyl groups as defined herein and alkynyl groups as defined herein, respectively, are divalent groups having single bonds for attachment to two other groups, they are termed "alkenylene" and "alkynylene" respectively.

The term "$C_{2-20}$alkenyl" as a group or part of a group, to an unsaturated hydrocarbyl group, which may be linear, branched or cyclic, comprising one or more carbon-carbon double bonds. Alkenyl groups thus preferably comprise between 2 and 20 carbon atoms, preferably between 2 and 10 carbon atoms, still more preferably between 2 and 6 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "$C_{2-20}$alkynyl" as a group or part of a group, refers to a class of monovalent unsaturated hydrocarbyl groups, wherein the unsaturation arises from the presence of one or more carbon-carbon triple bonds. Alkynyl groups thus preferably comprise between 2 and 20 carbon atoms, preferably between 2 and 10 carbon atoms, still more preferably between 2 and 6 carbon atoms. Non limiting examples of alkynyl groups are ethynyl, 2-propynyl, 2-butynyl, 3-butynyl, 2-pentynyl and its isomers, 2-hexynyl and its isomers—and the like.

The term "cycloalkyl", as a group or part of a group, refers to a cyclic alkyl group, that is a monovalent, saturated, hydrocarbyl group having 1 or more cyclic structure, and comprising from 3 to 12 carbon atoms, more preferably from 3 to 8 carbon atoms, more preferably from 5 to 6 carbon atoms, still more preferably from 5 to 6 carbon atoms. Cycloalkyl includes all saturated hydrocarbon groups containing 1 or more rings, including monocyclic or bicyclic groups. The further rings of multi-ring cycloalkyls may be either fused, bridged and/or joined through one or more spiro atoms. The term "$C_{3-8}$cycloalkyl", refers to a monovalent, saturated, hydrocarbyl group having 1 or more cyclic structure, and comprising from 3 to 8 carbon atoms, more preferably from 5 to 8 carbon atoms, more preferably from 5 to 6 carbon atoms. Examples of $C_{3-8}$cycloalkyl groups include but are not limited to cyclopropyl, cyclobutyl, cyclopentyl, cyclohexyl. Cycloalkyl groups may also be considered to be a subset of homocyclic rings discussed hereinafter. When the suffix "ene" is used in conjunction with a cycloalkyl group, i.e. cycloalkylene, this is intended to mean the cycloalkyl group as defined herein having two single bonds as points of attachment to other groups. Non-limiting examples of "$C_{3-8}$cycloalkylene" include 1,2-cyclopropylene, 1,1-cyclopropylene, 1,1-cyclobutylene, 1,2-cyclobutylene, 1,3-cyclopentylene, 1,1-cyclopentylene, and 1,4-cyclohexylene.

The term "$C_{3-8}$cycloalkyl$C_{1-20}$alkyl" as a group or part of a group, refers to a group or formula —$R^e$—$R''$ wherein $R^e$ is $C_{1-20}$alkylene, and $R''$ is a $C_{3-8}$cycloalkyl group as defined herein.

The term "$C_{1-20}$alkyl$C_{3-8}$cycloalkyl" as a group or part of a group, refers to a group or formula —$R^o$—$R^a$ wherein $R^o$ is $C_{3-8}$cycloalkylene and $R^a$ is a $C_{1-20}$alkyl group as defined herein.

The term "$C_{1-20}$alkyl$C_{3-8}$cycloalkyl$C_{1-20}$alkyl" as a group or part of a group, refers to a group or formula —$R^e$—$R^o$—$R^a$ wherein $R^o$ is $C_{3-8}$cycloalkylene, $R^e$ is $C_{1-20}$alkylene, and $R^a$ is a $C_{1-20}$alkyl group as defined herein.

The term "$C_{3-8}$cycloalkyl$C_{1-20}$alkyl$C_{3-8}$cycloalkyl" as a group or part of a group, refers to a group or formula —$R^o$—$R^e$—$R''$ wherein $R^o$ is $C_{3-8}$cycloalkylene, $R^e$ is $C_{1-20}$alkylene, and $R''$ is a $C_{3-8}$cycloalkyl group as defined herein.

The term "homocyclic ring" as a group or part of a group, refers to a ring wherein the ring atoms comprise only carbon atoms. Non limiting examples of homocyclic rings include cycloalkyl, cycloalkenyl, with cycloalkyl being preferred. Where a ring carbon atom is replaced with a heteroatom, preferably nitrogen, oxygen of sulfur, the heteroatom-containing ring resultant from such a replacement is referred to herein as a heterocyclic ring. More than one carbon atom in a ring may be replaced so forming heterocyclic ring having a plurality of heteroatoms.

The term "halo$C_{1-20}$alkyl" as a group or part of a group, refers to a $C_{1-20}$alkyl group having the meaning as defined above wherein one or more hydrogens are replaced with one or more halogen as defined above. Non-limiting examples of such haloalkyl groups include chloromethyl, 1-bromoethyl, fluoromethyl, difluoromethyl, trifluoromethyl, 1,1,1-trifluoroethyl and the like.

The term "$C_{1-20}$alkoxy" or "$C_{1-20}$alkyloxy", as a group or part of a group, refers to a group having the Formula —$OR^a$ wherein $R^a$ is $C_{1-20}$alkyl as defined herein above. Non-limiting examples of suitable $C_{1-20}$alkoxy include methoxy, ethoxy, propoxy, isopropoxy, butoxy, isobutoxy, sec-butoxy, tert-butoxy, pentyloxy and hexyloxy.

The term "$C_{1-20}$alkoxy$C_{1-20}$alkyl" or "$C_{1-20}$alkyloxy$C_{1-20}$alkyl", as a group or part of a group, refers to a group having the Formula —$R^e$—O—$R^a$ wherein $R^a$ is $C_{1-20}$alkyl as defined herein, and $R^e$ is $C_{1-20}$alkylene.

The term "$C_{1-20}$alkylthio", as a group or part of a group, refers to a group having the Formula —S—$R^a$ wherein $R^a$ is $C_{1-20}$alkyl as defined herein above. Non-limiting examples of $C_{1-20}$alkylthio groups include methylthio (—$SCH_3$), ethylthio (—SCH$_2$CH$_3$), n-propylthio, isopropylthio, n-butylthio, isobutylthio, sec-butylthio, tert-butylthio, and the like.

The term "C$_{1-20}$alkylthioC$_{1-20}$alkyl", as a group or part of a group, refers to a group having the Formula —R$^e$—S—R$^a$ wherein R$^a$ is C$_{1-20}$alkyl as defined herein, and R$^e$ is C$_{1-20}$alkylene.

The term "haloC$_{1-20}$alkoxy", as a group or part of a group, refers to a group of Formula —O—R$^b$ wherein R$^b$ is haloC$_{1-20}$alkyl as defined herein. Non-limiting examples of suitable haloC$_{1-20}$alkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy, trichloromethoxy, 2-bromoethoxy, pentafluoroethyl, 3,3,3-trichloropropoxy, 4,4,4-trichlorobutoxy.

The terms "mono- or di-C$_{1-20}$alkylamino" or "C$_{1-20}$alkylamino", as a group or part of a group, refers to a group of formula —N(R$^c$)(R$^d$) wherein R$^c$ and R$^d$ are each independently selected from hydrogen, or C$_{1-20}$alkyl, wherein at least one of R$^c$ or R$^d$ is C$_{1-20}$alkyl. Thus, alkylamino include mono-alkyl amino group (e.g. mono-C$_{1-20}$alkylamino group such as methylamino and ethylamino), and di-alkylamino group (e.g. di-C$_{1-20}$alkylamino group such as dimethylamino and diethylamino). Non-limiting examples of suitable alkylamino groups include n-propylamino, isopropylamino, n-butylamino, i-butylamino, sec-butylamino, t-butylamino, pentylamino, n-hexylamino, di-n-propylamino, di-i-propylamino, ethylmethylamino, methyl-n-propylamino, methyl-i-propylamino, n-butylmethylamino, i-butylmethylamino, t-butylmethylamino, ethyl-n-propylamino, ethyl-i-propylamino, n-butylethylamino, i-butylethylamino, t-butylethylamino, di-n-butylamino, di-i-butylamino, methylpentylamino, methylhexylamino, ethylpentylamino, ethylhexylamino, propylpentylamino, propylhexylamino, and the like.

The terms "mono- or di-C$_{1-20}$alkylaminoC$_{1-20}$alkyl" or "C$_{1-20}$alkylaminoC$_{1-20}$alkyl", as a group or part of a group, refers to a group of formula —R$^e$—N(R$^c$)(R$^d$) wherein R$^c$ and R$^d$ are each independently selected from hydrogen, or C$_{1-20}$alkyl, wherein at least one of R$^c$ or R$^d$ is C$_{1-20}$alkyl and R$^e$ is C$_{1-20}$alkylene.

The term "C$_{1-20}$alkoxycarbonyl", as a group or part of a group, refers to a group of formula —C(=O)OR$^a$, wherein R$^a$ is as defined above for C$_{1-20}$alkyl.

The term "C$_{1-20}$alkylcarbonyloxy", as a group or part of a group, refers to a group of Formula —O—C(=O)R$^a$ wherein R$^a$ is as defined above for C$_{1-20}$alkyl.

The term "C$_{6-12}$aryl", as a group or part of a group, refers to a polyunsaturated, aromatic hydrocarbyl group having a single ring (i.e. phenyl) or multiple aromatic rings fused together (e.g. naphthalene), or linked covalently, typically containing 6 to 12 atoms; wherein at least one ring is aromatic. The aromatic ring may optionally include one to two additional rings (either cycloalkyl, heterocyclyl or heteroaryl) fused thereto. Examples of suitable aryl include C$_{6-10}$aryl, more preferably C$_{6-8}$aryl. Non-limiting examples of C$_{6-12}$aryl comprise phenyl, biphenylyl, biphenylenyl, or 1- or 2-naphthanelyl; 5- or 6-tetralinyl, 1-, 2-, 3-, 4-, 5-, 6-, 7- or 8-azulenyl, 4-, 5-, 6 or 7-indenyl, 4- or 5-indanyl, 5-, 6-, 7- or 8-tetrahydronaphthyl, 1,2,3,4-tetrahydronaphthyl, and 1,4-dihydronaphthyl. When the suffix "ene" is used in conjunction with an aryl group, i.e. arylene, this is intended to mean the aryl group as defined herein having two single bonds as points of attachment to other groups. Suitable "C$_{6-12}$arylene" groups include 1,4-phenylene, 1,2-phenylene, 1,3-phenylene, biphenylylene, naphthylene, indenylene, 1-, 2-, 5- or 6-tetralinylene, and the like. Where a carbon atom in an aryl group is replaced with a heteroatom, the resultant ring is referred to herein as a heteroaryl ring.

The term "C$_{6-12}$arylC$_{1-20}$alkyl", as a group or part of a group, refers to a group or formula —R$^e$R$^h$ wherein R$^e$ is C$_{1-20}$alkylene, and R$^h$ is a C$_{6-12}$aryl group as defined herein. Non-limiting examples of C$_{6-12}$arylC$_{1-20}$alkyl group include benzyl, phenethyl, dibenzylmethyl, methylphenylmethyl, 3-(2-naphthyl)-butyl, and the like.

The term "C$_{6-12}$arylC$_{1-12}$alkylC$_{6-12}$aryl", as a group or part of a group, refers to a group or formula —R$^m$—R$^e$—R$^h$ wherein R$^m$ is C$_{6-12}$arylene, R$^e$ is C$_{1-20}$alkylene, and R$^h$ is a C$_{6-12}$aryl group as defined herein.

The term "C$_{1-20}$alkylC$_{6-12}$aryl", as a group or part of a group, refers to a group or formula —R$^m$—R$^a$ wherein R$^m$ is C$_{6-12}$arylene and R$^a$ is a C$_{1-20}$alkyl group as defined herein.

The term "C$_{1-20}$alkylC$_{6-12}$arylC$_{1-20}$alkyl", as a group or part of a group, refers to a group or formula —R$^e$—R$^m$—R$^a$ wherein R$^m$ is C$_{6-12}$arylene, R$^e$ is C$_{1-20}$alkylene, and R$^a$ is a C$_{1-20}$alkyl group as defined herein.

The terms "heterocyclyl" or "heterocycle", as a group or part of a group, refer to non-aromatic, fully saturated or partially unsaturated cyclic groups containing one or more cycles (for example, 3 to 7 member monocyclic, 7 to 11 member bicyclic, or containing a total of 3 to 10 ring atoms) which can be fused together or linked covalently, wherein at least one the cycles contains at least one heteroatom, selected from N, O and/or S atoms, wherein the N and S heteroatoms may optionally be oxidized and the N heteroatoms may optionally be quaternized. Preferably, each heterocyclyl may contain from 3 to 12 atoms, preferably from 3 to 8 atoms, more preferably from 3 to 6 atoms. Preferably, each ring of the heterocyclyl contains 1, 2, 3 or 4 heteroatoms selected from N, O and/or S, where the N and S heteroatoms may optionally be oxidized and the N heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. When the suffix "ene" is used in conjunction with a heterocyclyl group (i.e. "heterocyclylene") this is intended to mean the heterocyclyl group as defined herein having two single bonds as points of attachment to other groups.

Non limiting exemplary heterocyclic groups include aziridinyl, oxiranyl, thiiranyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, isoindolinyl, 2H-pyrrolyl, 1-pyrrolinyl, 2-pyrrolinyl, 3-pyrrolinyl, pyrrolidinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, oxetanyl, thietanyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl.

The term "heterocyclylC$_{1-20}$alkyl", as a group or part of a group, refers to a group or formula —R$^e$R$^g$ wherein R$^e$ is C$_{1-20}$alkylene and R$^g$ is a heterocyclyl group as defined herein.

The term "$C_{1-20}$alkylheterocyclyl$C_{1-20}$alkyl", as a group or part of a group, refers to a group or formula —$R^e$—$R^j$—$R^a$ wherein $R^e$ is $C_{1-20}$alkylene, $R^j$ is heterocyclylene and $R^a$ is a $C_{1-20}$alkyl group as defined herein.

The term "heterocyclyloxycarbonyl" as a group or part of a group, refers to a group of Formula —C(=O)—O—$R^g$ wherein $R^g$ is heterocyclyl as defined herein.

The term "heteroaryl" as a group or part of a group, refers but is not limited to 5 to 12 atom aromatic rings or ring systems containing one or more rings (for example 1, 2, or 3 rings) which can be fused together or linked covalently, typically containing 5 to 12 atoms; wherein at least one the rings is aromatic and contains at least one heteroatom, selected from N, O and/or S atoms, wherein the N and S heteroatoms may optionally be oxidized and the N heteroatoms may optionally be quaternized. Preferably each ring may contain from 5 to 10 atoms, preferably from 5 to 8 atoms, more preferably from 5 to 6 atoms. Such rings may be fused to an aryl, cycloalkyl, heteroaryl or heterocyclyl ring. When the suffix "ene" is used in conjunction with a heteroaryl group (i.e. "heteroarylene") this is intended to mean the heteroaryl group as defined herein having two single bonds as points of attachment to other groups.

Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl.

The term "pyrrolyl" (also called azolyl) as used herein includes pyrrol-1-yl, pyrrol-2-yl and pyrrol-3-yl. The term "furanyl" (also called "furyl") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl). The term "pyrazolyl" (also called 1H-pyrazolyl and 1,2-diazolyl) as used herein includes pyrazol-1-yl, pyrazol-3-yl, pyrazol-4-yl and pyrazol-5-yl. The term "imidazolyl" as used herein includes imidazol-1-yl, imidazol-2-yl, imidazol-4-yl and imidazol-5-yl. The term "oxazolyl" (also called 1,3-oxazolyl) as used herein includes oxazol-2-yl; oxazol-4-yl and oxazol-5-yl. The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl), as used herein includes thiazol-2-yl, thiazol-4-yl and thiazol-5-yl (also called 2-thiazolyl, 4-thiazolyl and 5-thiazolyl). The term "isothiazolyl" (also called 1,2-thiazolyl) as used herein includes isothiazol-3-yl, isothiazol-4-yl, and isothiazol-5-yl. The term "triazolyl" as used herein includes 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl. The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl. The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl. The term "tetrazolyl" as used herein includes 1H-tetrazol-1-yl, 1H-tetrazol-5-yl, 2H-tetrazol-2-yl, and 2H-tetrazol-5-yl. The term "oxatriazolyl" as used herein includes 1,2,3,4-oxatriazol-5-yl and 1,2,3,5-oxatriazol-4-yl. The term "thiatriazolyl" as used herein includes 1,2,3,4-thiatriazol-5-yl and 1,2,3,5-thiatriazol-4-yl. The term "pyridinyl" (also called "pyridyl") as used herein includes pyridin-2-yl, pyridin-3-yl and pyridin-4-yl (also called 2-pyridyl, 3-pyridyl and 4-pyridyl). The term "pyrimidyl" as used herein includes pyrimid-2-yl, pyrimid-4-yl, pyrimid-5-yl and pyrimid-6-yl. The term "pyrazinyl" as used herein includes pyrazin-2-yl and pyrazin-3-yl. The term "pyridazinyl as used herein includes pyridazin-3-yl and pyridazin-4-yl. The term "oxazinyl" (also called "1,4-oxazinyl") as used herein includes 1,4-oxazin-4-yl and 1,4-oxazin-5-yl. The term "dioxinyl" (also called "1,4-dioxinyl") as used herein includes 1,4-dioxin-2-yl and 1,4-dioxin-3-yl. The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl. The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl. The term "imidazo[2,1-b][1,3]thiazolyl" as used herein includes imidazo[2,1-b][1,3]thiazol-2-yl, imidazo[2,1-b][1,3]thiazol-3-yl, imidazo[2,1-b][1,3]thiazol-5-yl and imidazo[2,1-b][1,3]thiazol-6-yl. The term "thieno[3,2-b]furanyl" as used herein includes thieno[3,2-b]furan-2-yl, thieno[3,2-b]furan-3-yl, thieno[3,2-b]furan-4-yl, and thieno[3,2-b]furan-5-yl. The term "thieno[3,2-b]thiophenyl" as used herein includes thieno[3,2-b]thien-2-yl, thieno[3,2-b]thien-3-yl, thieno[3,2-b]thien-5-yl and thieno[3,2-b]thien-6-yl. The term "thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl. The term "thieno[2,3-d]imidazolyl" as used herein includes thieno[2,3-d]imidazol-2-yl, thieno[2,3-d]imidazol-4-yl and thieno[2,3-d]imidazol-5-yl. The term "tetrazolo[1,5-a]pyridinyl" as used herein includes tetrazolo[1,5-a]pyridine-5-yl, tetrazolo[1,5-a]pyridine-6-yl, tetrazolo[1,5-a]pyridine-7-yl, and tetrazolo[1,5-a]pyridine-8-yl. The term "indolyl" as used herein includes indol-1-yl, indol-2-yl, indol-3-yl, -indol-4-yl, indol-5-yl, indol-6-yl and indol-7-yl. The term "indolizinyl" as used herein includes indolizin-1-yl, indolizin-2-yl, indolizin-3-yl, indolizin-5-yl, indolizin-6-yl, indolizin-7-yl, and indolizin-8-yl. The term "isoindolyl" as used herein includes isoindol-1-yl, isoindol-2-yl, isoindol-3-yl, isoindol-4-yl, isoindol-5-yl, isoindol-6-yl and isoindol-7-yl. The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl. The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl. The term "benzothiophenyl" (also called benzo[b]thienyl) as used herein includes 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl (also called benzothien-2-yl, benzothien-3-yl, benzothien-4-yl, benzothien-5-yl, benzothien-6-yl and benzothien-7-yl). The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl. The term "indazolyl" (also called 1H-indazolyl or 2-azaindolyl) as used herein includes 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, and 2H-indazol-7-yl. The term "benzimidazolyl" as used herein includes benzimidazol-1-yl, benzimidazol-2-yl, benzimidazol-4-yl, benzimidazol-5-yl, benzimidazol-6-yl and benzimidazol-7-yl. The term "1,3-benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl. The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl. The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl. The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl. The term "1,2-benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl. The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl. The term "benzotriazolyl" as used herein includes benzotriazol-1-yl, benzotriazol4-yl, benzotriazol-5-yl, benzotriazol-6-yl and benzotriazol-7-yl. The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl. The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl. The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl. The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl. The term "thienopyridinyl" as used herein includes thieno[2,3-b]pyridinyl, thieno[2,3-c]pyridinyl, thieno[3,2-c]pyridinyl and thieno[3,2-b]pyridinyl. The term "purinyl" as used herein includes purin-2-yl, purin-6-yl, purin-7-yl and purin-8-yl. The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl. The term "1,3-benzodioxolyl", as used herein includes 1,3-benzodioxol-4-yl, 1,3-benzodioxol-5-yl, 1,3-benzodioxol-6-yl, and 1,3-benzodioxol-7-yl. The term "quinolinyl" as used herein includes quinolin-2-yl, quinolin-3-yl, quinolin-4-yl, quinolin-5-yl, quinolin-6-yl, quinolin-7-yl and quinolin-8-yl. The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl. The term "cinnolinyl" as used herein includes cinnolin-3-yl, cinnolin-4-yl, cinnolin-5-yl, cinnolin-6-yl, cinnolin-7-yl and cinnolin-8-yl. The term "quinazolinyl" as used herein includes quinazolin-2-yl, quinazolin-4-yl, quinazolin-5-yl, quinazolin-6-yl, quinazolin-7-yl and quinazolin-8-yl. The term "quinoxalinyl". as used herein includes quinoxalin-2-yl, quinoxalin-5-yl, and quinoxalin-6-yl.

Where an alkylene, cycloalkylene, or heterocyclylene group is present, connectivity to the molecular structure of which it forms part may be through a common carbon atom or different carbon atom. To illustrate this applying asterisk nomenclature a $C_3$alkylene group may be for example *—$CH_2CH_2CH_2$—*, *—CH(—$CH_2CH_3$)—* or *—$CH_2$CH(—$CH_3$)—*. Likewise a $C_3$cycloalkylene group may be

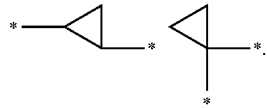

The term "heteroaryloxycarbonyl" as a group or part of a group, refers to a group of Formula —C(=O)—O—$R^i$ wherein $R^i$ is heteroaryl as defined herein.

The term "$C_{6-12}$aryloxycarbonyl" as a group or part of a group, refers to a group of Formula —C(=O)—O—$R^h$ wherein $R^h$ is $C_{6-12}$aryl as defined herein.

The term "heterocyclylcarbonyloxy" as a group or part of a group, refers to a group of Formula —O—C(=O)—$R^g$ wherein $R^g$ is heterocyclyl as defined herein.

The term "arylcarbonyloxy" as a group or part of a group, refers to refers to a group of Formula —O—C(=O)—$R^h$ wherein $R^h$ is aryl as defined herein.

The term "heteroarylcarbonyloxy" as a group or part of a group, refers to refers to a group of Formula —O—C(=O)—$R^i$ wherein $R^i$ is heteroaryl as defined herein.

The term "$C_{1-20}$alkylcarbonylamino" as a group or part of a group, refers to a group of Formula —NH(C=O)$R^a$ or —$NR^a$(C=O)$R^a$, wherein $R^a$ is $C_{1-20}$alkyl.

The term "halo$C_{1-20}$alkylcarbonylamino" as a group or part of a group, refers to a group of Formula —NH(C=O)$R^k$ or —$NR^a$(C=O)$R^k$, wherein $R^a$ is $C_{1-20}$alkyl as defined herein and $R^k$ is halo$C_{1-20}$alkyl as defined herein.

The term "heterocyclylcarbonylamino" as a group or part of a group, refers to a group of Formula —NH(C=O)$R^g$ or —$NR^a$(C=O)$R^g$, wherein $R^a$ is $C_{1-20}$alkyl as defined herein and $R^g$ is heterocyclyl as defined herein The term "$C_{6-12}$arylcarbonylamino" as a group or part of a group, refers to a group of Formula —NH(C=O)$R^h$ or —$NR^a$(C=O)$R^h$, wherein $R^a$ is $C_{1-20}$alkyl as defined herein and $R^h$ is $C_{6-12}$aryl as defined herein.

The term "heteroarylcarbonylamino" as a group or part of a group, refers to a group of Formula —NH(C=O)$R^i$ or —$NR^a$(C=O)$R^i$, wherein $R^a$ is $C_{1-20}$alkyl as defined herein and $R^i$ is heteroaryl as defined herein.

The term "carbamoyl" (aminocarbonyl) as a group or part of a group, refers to the group —(C=O)—$NH_2$.

The term "functionality" as used herein refers to the number of reactive centers and it is calculated from the structural formula. In an embodiment, unless otherwise stated, the term "functionality" refers to the number of reactive species (functions) of formula —X—C(=O)—$CHR^1$—C(=O)—$R^2$, —C(=O)—C≡C—$R^2$; or —C(=O)—$CR^1$=$CR^2$—$NR^4R^5$.

Preferred statements (features) and embodiments of the articles, resins and uses of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous.

Hereto, the present invention is in particular captured by any one or any combination of one or more of the below numbered aspects and embodiments 1 to 34, with any other statement and/or embodiments.

1. A composition comprising a polymeric network having at least one unit of formula (I), (II), and/or (III),

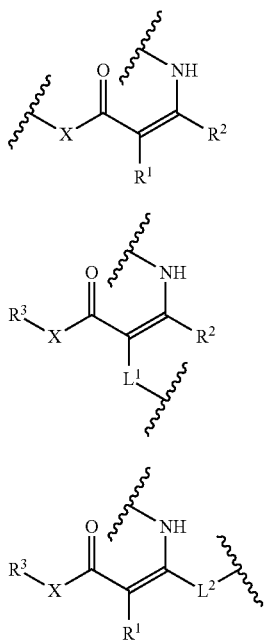

wherein said composition is obtained by contacting at least one compound A comprising at least two functions selected from the group of function of formula —X—C(═O)—CHR$^1$—C(═O)—R$^2$, —C(═O)—C≡C—R$^2$; or —C(═O)—CR$^1$═CR$^2$—NR$^4$R$^5$; wherein at least 25% by weight of compounds A has a functionality ≤5, preferably ≤4, more preferably ≤3, with % by weight based on the total weight of compounds A;

with at least one compound B comprising at least one —NH$_2$, or —NH$_3^+$ groups, or at least one functional group that generates —NH$_2$ or NH$_3^+$ in situ, such as —N═C═O, or a group of formula

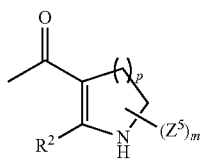

which is a compound generating —NH$_2$ in situ after reaction with another —NH$_2$;
wherein the ratio R=(sum(functionality of compound A×number of moles of compound A))/(sum(functionality of compound B×number of moles of all compound B)) is <1;

$$\left( \frac{\sum f_a N_a}{\sum f_b N_b} = R < 1 \right)$$

wherein $f_a N_a$ denotes the number of moles of —X—C(═O)—CHR$^1$—C(═O)—R$^2$, —C(═O)—C≡C—R$^2$; or —C(═O)—CR$^1$═CR$^2$—NR$^4$R$^5$ functions of the at least one compound A, and $f_b N_b$ denotes the number of moles of —NH$_2$, and/or —NH$_3^+$ groups or the number of moles of functional groups which could generate —NH$_2$ or NH$_3^+$ in situ, such as —N═C═O, of the at least one compound B;

R$^1$ is hydrogen or is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkyl C$_{1-20}$alkyl; heteroC$_{1-20}$alkyl; heterocyclyl; heterocyclylC$_{1-20}$alkyl; heteroaryl; and heteroarylC$_{1-20}$alkyl;
wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;
wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C═O, C═S, N═O, N═S, S═O or S(O)$_2$;
wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^1$; each Z$^1$ is independently selected from the group consisting of halogen; C$_{1-20}$alkyl; C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$; and R$^4$ is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkylC$_{1-20}$alkyl; heteroC$_{1-20}$alkyl; heterocyclyl; heterocyclylC$_{1-20}$alkyl; heteroaryl; and heteroarylC$_{1-20}$alkyl;
wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;
wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C═O, C═S, N═O, N═S, S═O or S(O)$_2$;
wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^4$; each Z$^4$ is independently selected from the group consisting of NR$^{11}$R$^{12}$; halogen; C$_{1-20}$alkyl; C$_{2-20}$alkenyl, $C_{2-20}$alkynyl, $C_{6-12}$aryl, $C_{3-8}$cycloalkyl, $C_{6-12}$aryl $C_{1-20}$alkyl, heteroC$_{1-20}$alkyl; heterocyclyl; heteroaryl; $C_{3-8}$cycloalkylC$_{1-20}$alkyl; heterocyclyl C$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; cyano; —CO$_2$R$^{10}$; —C(O)NR$^{11}$R$^{12}$; and —C(O)R$^9$;

or wherein the ratio R=(sum(functionality of compound A)×number of moles of compound A))/(sum(functionality of compound A×number of moles of compound A)+sum(functionality of compound B×number of moles of all compound B)) is <1;

$$\left(\frac{\sum f_a N_a}{\sum f_a N_a + \sum f_b N_b} = R < 1\right)$$

when R$^1$ and R$^4$ together with the atom to which they are attached form a 5-, 6-, or 7-membered heterocyclyl or heteroaryl; wherein each of said heterocyclyl; or heteroaryl; can be unsubstituted or substituted with one or more Z$^5$; each Z$^5$ is independently selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; halogen; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$; wherein $f_a N_a$ denotes the number of moles of —X—C(=O)—CHR$^1$—C(=O)—R$^2$, —C(=O)—C≡C—R$^2$; or —C(=O)—CR$^1$=CR$^2$—NR$^4$R$^5$ functions of the at least one compound A, and $f_b N_b$ denotes the number of moles of —NH$_2$, and/or —NH$_3^+$ groups or the number of moles of functional groups which could generate —NH$_2$ or NH$_3^+$ in situ, such as —N=C=O, of the at least one compound B; and wherein X is selected from O, NR$^{13}$, or CR$^{14}$R$^{15}$; or X and R$^3$ together form a group R$^6$, wherein R$^6$ is selected from the group consisting of C$_{6-12}$aryl, heteroaryl or heterocyclyl; wherein said C$_{6-12}$aryl, heteroaryl or heterocyclyl can be unsubstituted or substituted with one or more Z$^{31}$; and Z$^{31}$ is independently selected from the group consisting of —C(=O)—C≡C—R$^2$; —X—C(=O)—CHR$^1$—C(=O)—R$^2$, or —C(=O)—CR$^1$=CR$^2$—NR$^4$R$^5$; halogen; C$_{1-20}$alkyl; C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclyl C$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$; or R$^3$ is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkyl$_{1-20}$alkyl; C$_{1-20}$alkylC$_{3-8}$cycloalkylC$_{1-20}$alkyl; C$_{3-8}$cycloalkyl C$_{1-20}$alkylC$_{3-8}$cycloalkyl; C$_{1-20}$alkylC$_{6-12}$aryl C$_{1-20}$alkyl; heteroC$_{1-20}$alkyl; heterocyclyl; heterocyclylC$_{1-20}$alkyl; C$_{1-20}$alkylheterocyclylC$_{1-20}$alkyl; heteroaryl; and heteroarylC$_{1-20}$alkyl;

wherein said C$_{1-20}$alkyl; C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; C$_{1-20}$alkylC$_{3-8}$cycloalkyl C$_{1-20}$alkyl; C$_{3-8}$cycloalkylC$_{1-20}$alkylC$_{3-8}$cycloalkyl; C$_{1-20}$alkylC$_{6-12}$arylC$_{1-20}$alkyl; C$_{1-20}$alkylheterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkyl$_{1-20}$alkyl; C$_{1-20}$alkylC$_{3-8}$cycloalkylC$_{1-20}$alkyl; C$_{3-8}$cycloalkylC$_{1-20}$alkylC$_{3-8}$cycloalkyl; C$_{1-20}$alkylC$_{6-12}$arylC$_{1-20}$alkyl; heteroC$_{1-20}$alkyl; heterocyclyl; heterocyclylC$_{1-20}$alkyl; C$_{1-20}$alkylheterocyclylC$_{1-20}$alkyl; heteroaryl; and heteroaryl C$_{1-20}$alkyl; can be oxidized to form at least one C=O, C=S, N=O, N=S, S=O or S(O)$_2$;

wherein said C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkyl$_{1-20}$alkyl; C$_{1-20}$alkylC$_{3-8}$cycloalkylC$_{1-20}$alkyl; C$_{3-8}$cycloalkylC$_{1-20}$alkylC$_{3-8}$cycloalkyl; C$_{1-20}$alkylC$_{6-12}$arylC$_{1-20}$alkyl; heteroC$_{1-20}$alkyl; heterocyclyl; heterocyclyl C$_{1-20}$alkyl; C$_{1-20}$alkylheterocyclylC$_{1-20}$alkyl; heteroaryl; and heteroarylC$_{1-20}$alkyl; can be unsubstituted or substituted with one or more Z$^3$; each Z$^3$ is independently selected from the group consisting of —X—C(=O)—CHR$^1$—C(=O)—R$^2$, —C(=O)—C≡C—R$^2$; or —C(=O)—CR$^1$=CR$^2$—NR$^4$R$^5$; halogen; C$_{1-20}$alkyl; haloC$_{1-20}$alkyl; haloC$_{1-20}$alkyloxy; C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

L$^1$ is selected from the group consisting of C$_{1-20}$alkylene, C$_{2-20}$alkenylene; C$_{2-20}$alkynylene; C$_{6-12}$arylene, C$_{3-8}$cycloalkylene; C$_{6-12}$aryleneC$_{1-20}$alkylene; C$_{3-8}$cycloalkyleneC$_{1-20}$alkylene; heteroC$_{1-20}$alkylene; heterocyclylene; heterocyclyleneC$_{1-20}$alkylene; heteroarylene; and heteroaryleneC$_{1-20}$alkylene;

wherein said C$_{1-20}$alkylene, C$_{2-20}$alkenylene, C$_{2-20}$alkynylene, C$_{3-8}$cycloalkyleneC$_{1-20}$alkylene; C$_{6-12}$arylC$_{1-20}$alkylene, heterocyclyleneC$_{1-20}$alkylene; and heteroaryleneC$_{1-20}$alkylene, optionally comprises one or more heteroatoms in the alkylene, alkenylene, alkynylene moiety, said heteroatoms being each independently selected from O, S and N;

wherein at least one carbon atom or heteroatom of said C$_{1-20}$alkylene, C$_{2-20}$alkenylene; C$_{2-20}$alkynylene; C$_{6-12}$arylene, C$_{3-8}$cycloalkylene; C$_{6-12}$arylene C$_{1-20}$alkylene; C$_{3-8}$cycloalkyleneC$_{1-20}$alkylene; heteroC$_{1-20}$alkylene; heterocyclylene; heterocycleneC$_{1-20}$alkylene; heteroarylene; and heteroaryleneC$_{1-20}$alkylene; can be oxidized to form at least one C=O, C=S, N=O, N=S, S=O or S(O)$_2$;

wherein said C$_{1-20}$alkylene, C$_{2-20}$alkenylene; C$_{2-20}$alkynylene; C$_{6-12}$arylene, C$_{3-8}$cycloalkylene; C$_{6-12}$aryleneC$_{1-20}$alkylene; C$_{3-8}$cycloalkylene C$_{1-20}$alkylene; heteroC$_{1-20}$alkylene; heterocyclylene; heterocyclyleneC$_{1-20}$alkylene; heteroarylene; and heteroaryleneC$_{1-20}$alkylene; can be unsubstituted or substituted with one or more $Z^{21}$; each $Z^{21}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$R^2$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^2$; each $Z^2$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$L^2$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene;

wherein said $C_{1-20}$alkylene, $C_{2-20}$alkenylene, $C_{2-20}$alkynylene, $C_{3-8}$cycloalkylene$C_{1-20}$alkylene; $C_{6-12}$aryl$C_{1-20}$alkylene, heterocyclylene$C_{1-20}$alkylene; and heteroarylene$C_{1-20}$alkylene, optionally comprises one or more heteroatoms in the alkylene, alkenylene, alkynylene moiety, said heteroatoms being each independently selected from O, S and N;

wherein at least one carbon atom or heteroatom of said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene; can be oxidized to form at least one C=O, C=S, N=O, N=S, S=O or $S(O)_2$;

wherein said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene; can be unsubstituted or substituted with one or more $Z^{22}$; each $Z^{22}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

or wherein $R^2$ and $R^4$ together with the atom to which they are attached form a 5-, 6-, or 7-membered heterocyclyl or heteroaryl; wherein each of said heterocyclyl; or heteroaryl; can be unsubstituted or substituted with one or more $Z^6$; each $Z^6$ is independently selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halogen; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$R^5$ is hydrogen or is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^7$; each $Z^7$ is independently selected from the group consisting of $NR^{11}R^{12}$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; cyano; —$CO_2R^{10}$; —$C(O)NR^{11}R^{12}$; and —$C(O)R^9$;

each $R^9$ is independently selected from hydroxyl; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$;

each $R^{10}$ is independently selected from the group consisting of hydrogen, $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$;

or wherein $R^{11}$ and $R^{12}$ together with the atom to which they are attached form a 5-, 6-, or 7-membered heterocyclyl;

$R^{13}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$;

$R^{14}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$;

$R^{15}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$.

2. A composition comprising a polymeric network, wherein said composition is obtained by contacting at least one compound A comprising at least two functions selected from the group of function of formula —X—C(=O)—CHR$^1$—C(=O)—R$^2$, —C(=O)—C≡C—R$^2$; or —C(=O)—CR$^1$=CR$^2$—NR$^4$R$^5$; wherein at least 25% by weight of compounds A has a functionality ≤5, preferably ≤4, more preferably ≤3, with % by weight based on the total weight of compounds A;

with at least one compound B comprising at least one —NH$_2$, or —NH$_3^+$ groups, or at least one functional group that generates —NH$_2$ or NH$_3^+$ in situ, such as —N=C=O; wherein the ratio R=(sum(functionality of compound A×number of moles of compound A))/(sum(functionality of compound B×number of moles of all compound B)) is <1;

$$\frac{\sum f_a N_a}{\sum f_b N_b} = R < 1$$

wherein $f_a N_a$ denotes the number of moles of —X—C(=O)—CHR$^1$—C(=O)—R$^2$, —C(=O)—C≡C—R$^2$; or —C(=O)—CR$^1$=CR$^2$—NR$^4$R$^5$ functions of the at least one compound A, and $f_b N_b$ denotes the number of moles of —NH$_2$, and/or —NH$_3^+$ groups or the number of moles of functional groups which could generate —NH$_2$ or NH$_3^+$ in situ, such as —N=C=O, of the at least one compound B;

R$^1$ is hydrogen or is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkylC$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;

wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^1$; each Z$^1$ is independently selected from the group consisting of halogen; C$_{1-20}$alkyl; C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$; and R$^4$ is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkylC$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;

wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^4$; each Z$^4$ is independently selected from the group consisting of NR$^{11}$R$^{12}$; halogen; C$_{1-20}$alkyl; C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; cyano; —CO$_2$R$^{10}$; —C(O)NR$^{11}$R$^{12}$; and —C(O)R$^9$;

or wherein the ratio R=(sum(functionality of compound A×number of moles of compound A))/(sum(functionality of compound A×number of moles of compound A)+sum(functionality of compound B×number of moles of all compound B)) is <1;

$$\frac{\sum f_a N_a}{\sum f_a N_a + \sum f_b N_b} = R < 1$$

when R$^1$ and R$^4$ together with the atom to which they are attached form a 5-, 6-, or 7-membered heterocyclyl or heteroaryl; wherein each of said heterocyclyl; or heteroaryl; can be unsubstituted or substituted with one or more Z$^5$; each Z$^5$ is independently selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; halogen; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

wherein $f_a N_a$ denotes the number of moles of —X—C(=O)—CHR$^1$—C(=O)—R$^2$, —C(=O)—C=C—R$^2$; or —C(=O)—CR$^1$=CR$^2$—NR$^4$R$^5$ functions of the at least one compound A, and $f_b N_b$ denotes the number of moles of —NH$_2$, and/or —NH$_3^+$ groups or the number of moles of functional groups which could generate —NH$_2$ or NH$_3^+$ in situ, such as —N=C=O, of the at least one compound B;

and wherein X, R$^2$, R$^5$, R$^9$, R$^{10}$, R$^{11}$, and R$^{12}$ have the same meaning as that defined herein above in statement 1.

3. A compound comprising at least two units and at most 5 units of formula (I), (II), and/or (III);

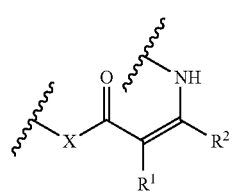

(I)

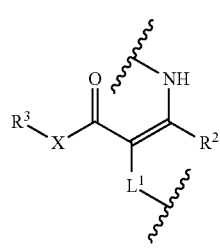

(II)

-continued

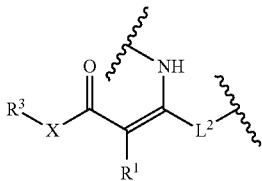

(III)

wherein $R^1$ is hydrogen or is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^1$; each $Z^1$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$; and X is selected from O, $NR^{13}$, or $CR^{14}R^{15}$; or X and $R^3$ together form a group $R^6$, wherein $R^6$ is selected from the group consisting of $C_{6-12}$aryl, heteroaryl or heterocyclyl; wherein said $C_{6-12}$aryl, heteroaryl or heterocyclyl can be unsubstituted or substituted with one or more $Z^{31}$; and $Z^{31}$ is independently selected from the group consisting of —C(=O)—C≡C—$R^2$; —X—C(=O)—CHR$^1$—C(=O)—$R^2$, or —C(=O)—CR$^1$=CR$^2$—NR$^4R^5$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl $C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$; or $R^3$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$_{1-20}$alkyl; $C_{1-20}$alkyl$C_{3-8}$cycloalkyl$C_{1-20}$alkyl; $C_{3-8}$cycloalkyl $C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl $C_{1-20}$alkyl; $C_{1-20}$alkylheterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; $C_{1-20}$alkyl$C_{3-8}$cycloalkyl $C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; $C_{1-20}$alkylheterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$_{1-20}$alkyl; $C_{1-20}$alkyl$C_{3-8}$cycloalkyl $C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl$C_{1-20}$alkyl; $C_{1-20}$alkylheterocyclyl$C_{1-20}$alkyl; heteroaryl; and heteroaryl $C_{1-20}$alkyl; can be oxidized to form at least one C=O, C=S, N=O, N=S, S=O or $S(O)_2$;

wherein said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl $C_{1-20}$alkyl; $C_{1-20}$-alkylheterocyclyl$C_{1-20}$alkyl; heteroaryl; and heteroaryl$C_{1-20}$alkyl; can be unsubstituted or substituted with one or more $Z^3$; each $Z^3$ is independently selected from the group consisting of —X—C(=O)—CHR$^1$—C(=O)—R$^1$, —C(=O)—C≡C—R$^2$; or —C(=O)—CR$^1$=CR$^2$—NR$^4R^5$; halogen; $C_{1-20}$alkyl; halo$C_{1-20}$alkyl; halo$C_{1-20}$alkyloxy; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{1-}$; —$C(O)NR^{11}R^{12}$; and —$C(O)R^9$;

$L^1$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene;

wherein said $C_{1-20}$alkylene, $C_{2-20}$alkenylene, $C_{2-20}$alkynylene, $C_{3-8}$cycloalkylene$C_{1-20}$alkylene; $C_{6-12}$aryl$C_{1-20}$alkylene, heterocyclylene$C_{1-20}$alkylene; and heteroarylene$C_{1-20}$alkylene, optionally comprises one or more heteroatoms in the alkylene, alkenylene, alkynylene moiety, said heteroatoms being each independently selected from O, S and N;

wherein at least one carbon atom or heteroatom of said $C_{1-20}$alkylene, $C_{2-20}$alkenylene; $C_{2-20}$alkynylene; $C_{6-12}$arylene, $C_{3-8}$cycloalkylene; $C_{6-12}$arylene $C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene; can be oxidized to form at least one C=O, C=S, N=O, N=S, S=O or $S(O)_2$;

wherein said $C_{1-20}$alkylene, $C_{2-20}$alkenylene; $C_{2-20}$alkynylene; $C_{6-12}$arylene, $C_{3-8}$cycloalkylene; $C_{6-12}$aryleneC$_{1-20}$alkylene; $C_{3-8}$cycloalkyleneC$_{1-20}$alkylene; heteroC$_{1-20}$alkylene; heterocyclylene; heterocycleneC$_{1-20}$alkylene; heteroarylene; and heteroaryleneC$_{1-20}$alkylene; can be unsubstituted or substituted with one or more $Z^{21}$; each $Z^{21}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$arylC$_{1-20}$alkyl, heteroC$_{1-20}$alkyl; heterocyclyl; heteroaryl; $C_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; $-OR^{10}$; $-SR^{10}$; $-S(O)R^9$; $-S(O)_2R^9$; $-SO_2NR^{11}R^{12}$; nitro; $-NR^{10}C(O)R^9$; $-NR^{10}S(O)_2R^9$; $-NR^{10}C(O)NR^{11}R^{12}$; $NR^{11}R^{12}$; cyano; $-CO_2R^{10}$; $-C(O)NR^{11}R^{12}$; and $-C(O)R^9$;

$R^2$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$arylC$_{1-20}$alkyl; $C_{3-8}$cycloalkylC$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said $C_{1-20}$alkyl, $C_{2-20}$alkenyl, $C_{2-20}$alkynyl, $C_{3-8}$cycloalkylC$_{1-20}$alkyl; $C_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$arylC$_{1-20}$alkyl, heteroC$_{1-20}$alkyl; heterocyclyl; heteroaryl; $C_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$arylC$_{1-20}$alkyl, heteroC$_{1-20}$alkyl; heterocyclyl; heteroaryl; $C_{3-8}$cycloalkylC$_{1-20}$alkyl; heterocyclylC$_{1-20}$alkyl; and heteroarylC$_{1-20}$alkyl; can be unsubstituted or substituted with one or more $Z^2$; each $Z^2$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$arylC$_{1-20}$alkyl, heteroC$_{1-20}$alkyl; heterocyclyl; heteroaryl; $C_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; $-OR^{10}$; $-SR^{10}$; $-S(O)R^9$; $-S(O)_2R^9$; $-SO_2NR^{11}R^{12}$; nitro; $-NR^{10}C(O)R^9$; $-NR^{10}S(O)_2R^9$; $-NR^{10}C(O)NR^{11}R^{12}$; $NR^{11}R^{12}$; cyano; $-CO_2R^{10}$; $-C(O)NR^{11}R^{12}$; and $-C(O)R^9$;

$L^2$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$aryleneC$_{1-20}$alkylene; $C_{3-8}$cycloalkyleneC$_{1-20}$alkylene; heteroC$_{1-20}$alkylene; heterocyclylene; heterocyleneC$_{1-20}$alkylene; heteroarylene; and heteroaryleneC$_{1-20}$alkylene;

wherein said $C_{1-20}$alkylene, $C_{2-20}$alkenylene, $C_{2-20}$alkynylene, $C_{3-8}$cycloalkyleneC$_{1-20}$alkylene; $C_{6-12}$arylC$_{1-20}$alkylene, heterocycleneC$_{1-20}$alkylene; and heteroaryleneC$_{1-20}$alkylene, optionally comprises one or more heteroatoms in the alkylene, alkenylene, alkynylene moiety, said heteroatoms being each independently selected from O, S and N;

wherein at least one carbon atom or heteroatom of said $C_{1-20}$alkylene, $C_{2-20}$alkenylene; $C_{2-20}$alkynylene; $C_{6-12}$arylene, $C_{3-8}$cycloalkylene; $C_{6-12}$arylene $C_{1-20}$alkylene; $C_{3-8}$cycloalkyleneC$_{1-20}$alkylene; heteroC$_{1-20}$alkylene; heterocyclylene; heterocycleneC$_{1-20}$alkylene; heteroarylene; and heteroaryleneC$_{1-20}$alkylene; can be oxidized to form at least one C=O, C=S, N=O, N=S, S=O or $S(O)_2$;

wherein said $C_{1-20}$alkylene, $C_{2-20}$alkenylene; $C_{2-20}$alkynylene; $C_{6-12}$arylene, $C_{3-8}$cycloalkylene; $C_{6-12}$aryleneC$_{1-20}$alkylene; $C_{3-8}$cycloalkyleneC$_{1-20}$ alkylene; heteroC$_{1-20}$alkylene; heterocyclylene; heterocycleneC$_{1-20}$alkylene; heteroarylene; and heteroaryleneC$_{1-20}$alkylene; can be unsubstituted or substituted with one or more $Z^{22}$; each $Z^{22}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$arylC$_{1-20}$alkyl, heteroC$_{1-20}$alkyl; heterocyclyl; heteroaryl; $C_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; $-OR^{10}$; $-SR^{10}$; $-S(O)R^9$; $-S(O)_2R^9$; $-SO_2NR^{11}R^{12}$; nitro; $-NR^{10}C(O)R^9$; $-NR^{10}S(O)_2R^9$; $-NR^{10}C(O)NR^{11}R^{12}$; $NR^{11}R^{12}$; cyano; $-CO_2R^{10}$; $-C(O)NR^{11}R^{12}$; and $-C(O)R^9$;

$R^4$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$arylC$_{1-20}$alkyl; $C_{3-8}$cycloalkylC$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said $C_{1-20}$alkyl, $C_{2-20}$alkenyl, $C_{2-20}$alkynyl, $C_{3-8}$cycloalkylC$_{1-20}$alkyl; $C_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$arylC$_{1-20}$alkyl, heteroC$_{1-20}$alkyl; heterocyclyl; heteroaryl; $C_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$arylC$_{1-20}$alkyl, heteroC$_{1-20}$alkyl; heterocyclyl; heteroaryl; $C_{3-8}$cycloalkylC$_{1-20}$alkyl; heterocyclylC$_{1-20}$alkyl; and heteroarylC$_{1-20}$alkyl; can be unsubstituted or substituted with one or more $Z^4$; each $Z^4$ is independently selected from the group consisting of $NR^{11}R^{12}$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl $C_{1-20}$alkyl, heteroC$_{1-20}$alkyl; heterocyclyl; heteroaryl; $C_{3-8}$cycloalkylC$_{1-20}$alkyl; heterocyclyl $C_{1-20}$alkyl; heteroarylC$_{1-20}$alkyl; haloC$_{1-20}$alkyl; haloC$_{1-20}$alkyloxy; $-OR^{10}$; $-SR^{10}$; $-S(O)R^9$; $-S(O)_2R^9$; $-SO_2NR^{11}R^{12}$; nitro; $-NR^{10}C(O)R^9$; $-NR^{10}S(O)_2R^9$; $-NR^{10}C(O)NR^{11}R^{12}$; cyano; $-CO_2R^{10}$; $-C(O)NR^{11}R^{12}$; and $-C(O)R^9$;

or $R^1$ and $R^4$ together with the atom to which they are attached form a 5-, 6-, or 7-membered heterocyclyl or heteroaryl; wherein each of said heterocyclyl; or heteroaryl; can be unsubstituted or substituted with one or more $Z^5$; each $Z^5$ is independently selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$arylC$_{1-20}$alkyl, heteroC$_{1-20}$alkyl; heterocyclyl; heteroaryl; $C_{3-8}$cycloalkylC$_{1-20}$alkyl; heterocyclylC$_{1-20}$alkyl; heteroarylC$_{1-20}$alkyl; halogen; haloC$_{1-20}$alkyl; halo $C_{1-20}$alkyloxy; $-OR^{10}$; $-SR^{10}$; $-S(O)R^9$;

—S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

R$^5$ is hydrogen or is selected from the group consisting of C$_{1-20}$alkyl, C$_{2-20}$alkenyl; C$_{2-20}$alkynyl; C$_{6-12}$aryl; C$_{3-8}$cycloalkyl; C$_{6-12}$arylC$_{1-20}$alkyl; C$_{3-8}$cycloalkyl C$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;

wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^7$; each Z$^7$ is independently selected from the group consisting of NR$^{11}$R$^{12}$; halogen; C$_{1-20}$alkyl; C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; cyano; —CO$_2$R$^{10}$; —C(O)NR$^{11}$R$^{12}$; and —C(O)R$^9$;

each R$^9$ is independently selected from hydroxyl; C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

each R$^{10}$ is independently selected from the group consisting of hydrogen, C$_{1-20}$alkyl, C$_{2-20}$alkenyl, C$_{2-20}$alkynyl, C$_{6-12}$aryl, C$_{3-8}$cycloalkyl, C$_{6-12}$aryl C$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

each R$^{11}$ and R$^{12}$ is independently selected from the group consisting of hydrogen; C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroaryl C$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

or wherein R$^{11}$ and R$^{12}$ together with the atom to which they are attached form a 5-, 6-, or 7-membered heterocyclyl;

R$^{13}$ is hydrogen or is selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

R$^{14}$ is hydrogen or is selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

R$^{15}$ is hydrogen or is selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; heterocyclyl$C_{1-20}$alkyl; and heteroaryl$C_{1-20}$alkyl; can be oxidized to form at least one C═O, C═S, N═O, N═S, S═O or $S(O)^2$.

4. The composition according to statement 1 or 2, wherein at least 30% by weight of compounds A have a functionality ≤5, preferably at least 35% by weight, preferably at least 40% by weight, preferably at least 45% by weight, most preferably at least 50% by weight.

5. The composition according to any one of statements 1 to 2, and 4, wherein at least 50% by weight of compounds A have a functionality ≤5.

6. The composition according to any one of statements 1 to 2, and 4 to 5, wherein at least 25% by weight of compounds A, preferably at least 30% by weight of compounds A have a functionality ≤5, preferably at least 30% by weight, preferably at least 35% by weight, preferably at least 40% by weight, preferably at least 45% by weight, most preferably at least 50% by weight of compounds A, have a functionality ≤4, more preferably ≤3.

7. The composition according to anyone of statements 1 to 2, and 4 to 6, wherein the ratio (sum(functionality of compound A×number of moles of compound A))/(sum(functionality of compound B×number of moles of all compound B)) is ≥0.90

$$\left(\text{or } \frac{\sum f_a N_a}{\sum f_b N_b} = R \geq 0.90\right),$$

preferably (sum(functionality of compound A×number of moles of compound A))/(sum(functionality of compound B×number of moles of all compound B)) is ≥0.92

$$\left(\text{or } \frac{\sum f_a N_a}{\sum f_b N_b} = R \geq 0.92\right),$$

preferably (sum(functionality of compound A×number of moles of compound A))/(sum(functionality of compound B×number of moles of all compound B)) is ≥0.94

$$\left(\text{or } \frac{\sum f_a N_a}{\sum f_b N_b} = R \geq 0.94\right),$$

preferably (sum(functionality of compound A×number of moles of compound A))/(sum(functionality of compound B×number of moles of all compound B)) is ≥0.95

$$\left(\text{or } \frac{\sum f_a N_a}{\sum f_b N_b} = R \geq 0.95\right),$$

8. The composition according to any one of statements 1 to 2 and 4 to 7, wherein said at least one compound A is a compound of formula (IV); (V); or (VI), or (VII);

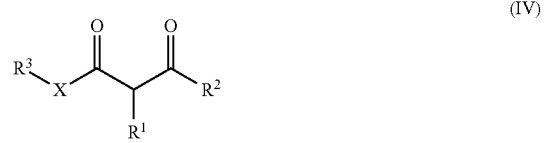

(IV)

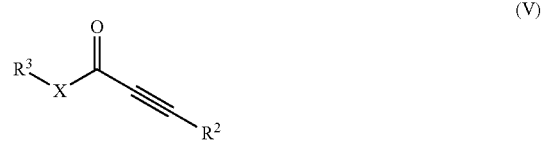

(V)

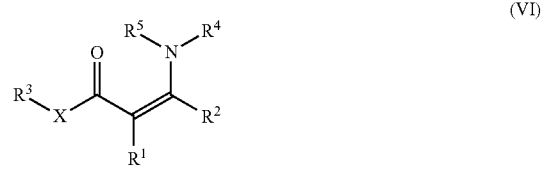

(VI)

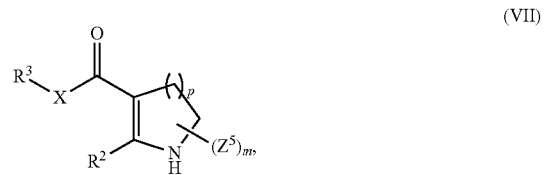

(VII)

wherein m is an integer selected from 0, 1, 2 or 3 and p is an integer selected from 1, 2, or 3.

9. The composition according to any one of statements 1 to 2 and 4 to 8, wherein said at least one compound A is a compound of formula (VIII), (IX), (X), (XI) or (XII)

(VIII)

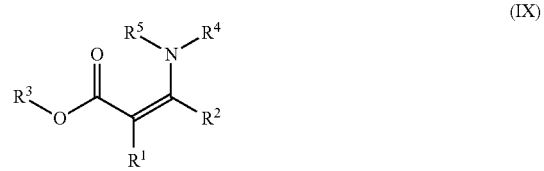

(IX)

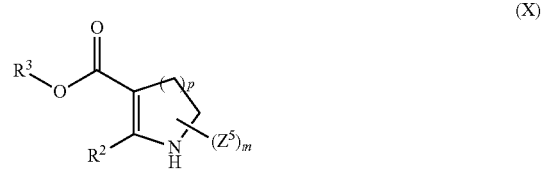

(X)

(XI)

(XII)

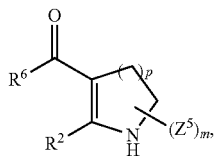

wherein m is an integer selected from 0, 1, 2 or 3 and p is an integer selected from 1, 2, or 3.

10. The composition according to any one of statements 1 to 2 and 4 to 9, wherein said at least one compound A is a compound of formula (XIII), (XIV), (XV), (XVI), (XVII), (XVIII), (XIX), (XX);

(XIII)
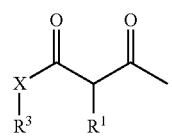

(XIV)
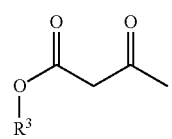

(XV)
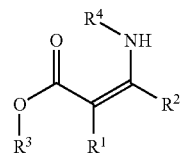

(XVI)
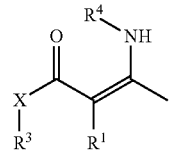

(XVII)
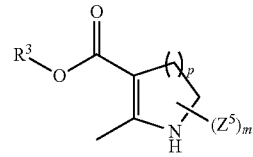

(XVIII)
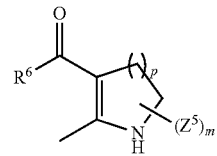

(XIX)
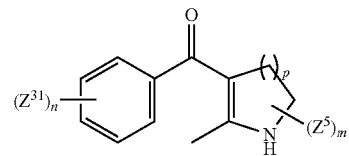

(XX)
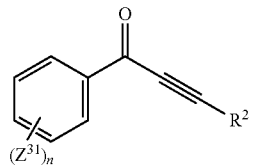

wherein n is an integer selected from 0, 1, 2 or 3; m is an integer selected from 0, 1, 2 or 3 and p is an integer selected from 1, 2, or 3.

11. The composition according to any one of statements 1 to 2 and 4 to 10, wherein said at least one compound A is a compound of formula (XXI), (XXII), (XXIII), (XXIV), (XXV), or (XXVI);

(XXI)
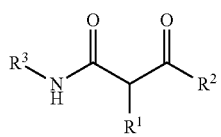

(XXII)
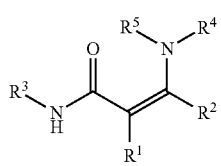

(XXIII)
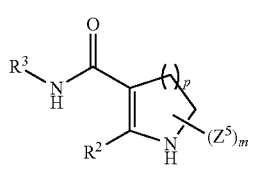

(XXIV)
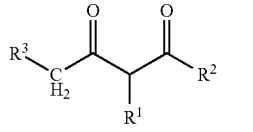

(XXV)
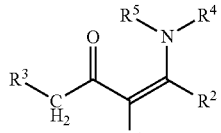

(XXVI)
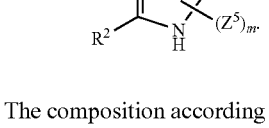

12. The composition according to any one of statements 1 to 2 and 4 to 11, wherein said composition is obtained by contacting at least one compound A with at least two different compounds B, each of said compound B comprising at least one —NH$_2$, or —NH$_3^+$ groups; or at least one functional group that generates —NH$_2$ or —NH$_3^+$ in situ, such as —N═C═O.

13. The composition according to any one of statements 1 to 2 and 4 to 12, wherein said at least one compound B comprises at least two groups selected from the group comprising —$NH_2$, and —$NH_3^+$; or at least two functional groups that generate —$NH_2$ or —$NH_3^+$ in situ, such as —N=C=O.

14. The composition according to any one of statements 1 to 2 and 4 to 13, wherein said at least one compound B comprises at least three groups selected from the group comprising —$NH_2$, and —$NH_3^+$; or at least three functional groups that generate —$NH_2$ or —$NH_3^+$ in situ, such as —N=C=O.

15. The composition according to any one of statements 1 to 2 and 4 to 14, or a compound according to statement 3, wherein $R^3$ is a group selected from -$L^3$-X—C(=O)—$CHR^1$—C(=O)—$R^2$, or -$L^3$-X—C(=O)—$CR^1$=$CR^2$—$NR^4R^5$, or -$L^3$-C(=O)—C≡C—$R^2$;
   wherein $L^3$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{1-20}$alkylene$C_{6-12}$arylene$C_{1-20}$alkylene; $C_{3-8}$cycloalkylene$C_{1-20}$alkylene; $C_{1-20}$alkylene$C_{3-8}$cycloalkylene$C_{1-20}$alkylene; $C_{1-20}$alkylene$C_{3-8}$cycloalkylene; $C_{3-8}$cycloalkylene$C_{1-20}$alkylene$C_{3-8}$cycloalkylene; $C_{1-20}$alkylene$C_{6-12}$aryl$C_{1-20}$alkylene; $C_{1-20}$alkyleneheterocyclylene$C_{1-20}$alkylene; hetero$C_{1-20}$alkylene; heterocyclylene; heterocyclylene$C_{1-20}$alkylene; heteroarylene; heteroaryl$C_{1-20}$alkylene; $C_{1-20}$alkyleneheterocyclylene $C_{1-20}$alkylene; and $C_{1-20}$alkyleneheteroaryl$C_{1-20}$alkylene;
   wherein said $C_{1-20}$alkylene, $C_{2-20}$alkenylene; $C_{2-20}$alkynylene; $C_{6-12}$arylene$C_{1-20}$alkylene; $C_{1-20}$alkylene$C_{6-12}$arylene$C_{1-20}$alkylene; $C_{3-8}$cycloalkylene$C_{1-20}$alkylene; $C_{1-20}$alkylene$C_{3-8}$cycloalkylene$C_{1-20}$alkylene; heterocyclylene $C_{1-20}$alkylene; heteroaryl$C_{1-20}$alkylene; $C_{1-20}$alkyleneheterocyclylene$C_{1-20}$alkylene; $C_{1-20}$alkylene$C_{3-8}$cycloalkylene$C_{1-20}$alkylene; $C_{3-8}$cycloalkylene$C_{1-20}$alkylene$C_{3-8}$cycloalkylene; $C_{1-20}$alkylene$C_{6-12}$aryl$C_{1-20}$alkylene; $C_{1-20}$alkyleneheterocyclylene$C_{1-20}$alkylene; and $C_{1-20}$alkyleneheteroaryl $C_{1-20}$alkylene, optionally comprises one or more heteroatoms in the alkylene, alkenylene, alkynylene moiety, said heteroatoms being each independently selected from O, S and N;
   wherein at least one carbon atom or heteroatom of said $C_{1-20}$alkylene, $C_{2-20}$alkenylene; $C_{2-20}$alkynylene; $C_{6-12}$arylene, $C_{3-8}$cycloalkylene; $C_{6-12}$arylene $C_{1-20}$alkylene; $C_{1-20}$alkylene$C_{6-12}$arylene$C_{1-20}$alkylene; $C_{3-8}$cycloalkylene$C_{1-20}$alkylene; $C_{1-20}$alkylene$C_{3-8}$cycloalkylene$C_{1-20}$alkylene; $C_{1-20}$alkylene $C_{3-8}$cycloalkylene$C_{1-20}$alkylene; $C_{3-8}$cycloalkylene$C_{1-20}$alkylene$C_{3-8}$cycloalkylene; $C_{1-20}$alkylene $C_{6-12}$aryl$C_{1-20}$alkylene; $C_{1-20}$alkyleneheterocyclylene$C_{1-20}$alkylene; hetero$C_{1-20}$alkylene; heterocyclylene; heterocyclylene$C_{1-20}$alkylene; heteroarylene; heteroaryl$C_{1-20}$alkylene; $C_{1-20}$alkyleneheterocyclylene$C_{1-20}$alkylene; and $C_{1-20}$alkyleneheteroaryl$C_{1-20}$alkylene; can be oxidized to form at least one C=O, C=S, N=O, N=S, S=O or $S(O)_2$;
   wherein said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{1-20}$alkylene$C_{6-12}$arylene$C_{1-20}$alkylene; $C_{3-8}$cycloalkylene$C_{1-20}$alkylene; $C_{1-20}$alkylene$C_{3-8}$cycloalkylene$C_{1-20}$alkylene; $C_{1-20}$alkylene$C_{3-8}$cycloalkylene$C_{1-20}$alkylene; $C_{3-8}$cycloalkylene$C_{1-20}$alkylene$C_{3-8}$cycloalkylene; $C_{1-20}$alkylene$C_{6-12}$aryl$C_{1-20}$alkylene; $C_{1-20}$alkyleneheterocyclylene$C_{1-20}$alkylene; hetero$C_{1-20}$alkylene; heterocyclylene; heterocyclylene$C_{1-20}$alkylene; heteroarylene; heteroaryl$C_{1-20}$alkylene; $C_{1-20}$alkyleneheterocyclylene$C_{1-20}$alkylene; and $C_{1-20}$alkyleneheteroaryl$C_{1-20}$alkylene; can be unsubstituted or substituted with one or more $Z^{10}$; each $Z^{10}$ is independently selected from the group consisting of —X—C(=O)—$CHR^1$—C(=O)—$R^2$, —C(=O)—$CR^1$=$CR^2$—$NR^4R^5$; or —C(=O)—C≡C—$R^2$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$.

16. The composition according to any one of statements 1 to 2 and 4 to 16, wherein said at least one compound B is an amine compound having an amine functionality of at least 2, preferably, at least 3, for example at least 4.

17. The composition according to any one of statements 1 to 2 and 4 to 16, wherein said at least one compound B is an amine compound comprising at least one $C_{1-36}$ hydrocarbyl group, wherein said $C_{1-36}$ hydrocarbyl group can be unsubstituted or substituted with one or more $Z^{16}$; each $Z^{16}$ is independently selected from the group consisting of $NR^{11}R^{12}$; cyano, nitro, —C(=O)—C≡C—$R^2$; —X—C(=O)—$CHR^1$—C(=O)—$R^2$, or —C(=O)—$CR^1$=$CR^2$—$NR^4R^5$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl $C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; cyano; —$CO_2R^{10}$; —$C(O)NR^{11}R^{12}$; and —$C(O)R^9$.

18. The composition according to statement 17, wherein said $C_{1-36}$hydrocarbyl group is preferably a $C_{2-36}$ hydrocarbyl group, preferably $C_{3-36}$ hydrocarbyl group, preferably $C_{4-36}$ hydrocarbyl group, preferably $C_{5-36}$ hydrocarbyl group, preferably $C_{6-36}$ hydrocarbyl group.

19. The composition according to any one of statements 1 to 2 and 4 to 18, wherein said at least one compound B is an amine compound comprising at least one group selected from the group comprising $C_{1-20}$alkyl, $C_{2-20}$alkenyl; $C_{2-20}$alkynyl; $C_{6-12}$aryl, $C_{3-8}$cycloalkyl; $C_{6-12}$aryl $C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;
   wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;
   wherein at least one carbon atom or heteroatom of said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl $C_{1-20}$alkyl; hetero$C_{1-20}$alkyl; heterocyclyl; heterocyclyl$C_{1-20}$alkyl; heteroaryl; and heteroaryl$C_{1-20}$alkyl; can be oxidized to form at least one C=O, C=S, N=O, N=S, S=O or $S(O)_2$;
   wherein said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl; can be unsubstituted or substituted with one or more $Z^{16}$; each $Z^{16}$ is independently selected from the group consisting of $NR^{11}R^{12}$; cyano, nitro, —C(=O)—C≡C—$R^2$; —X—C(=O)—CHR$^1$—C(=O)—$R^2$, or —C(=O)—CR$^1$=CR$^2$—NR$^4$R$^5$; halogen; $C_{1-20}$alkyl; $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; heteroaryl$C_{1-20}$alkyl; halo$C_{1-20}$alkyl; halo$C_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; cyano; —CO$_2$R$^{10}$; —C(O)NR$^{11}$R$^{12}$; and —C(O)R$^9$.

20. The composition according to any one of statements 1 to 2 and 4 to 20, wherein said at least one compound B is an amine compound having an amine functionality of at least 2, and comprising at least one group selected from the group comprising $C_{1-20}$alkyl, $C_{2-20}$alkenyl; $C_{1-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;
wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;
wherein at least one carbon atom or heteroatom of said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl; can be oxidized to form at least one C=O, C=S, N=O, N=S, S=O or S(O)$_2$;
wherein said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl; can be unsubstituted or substituted with one or more $Z^{16}$; each $Z^{16}$ is independently selected from the group consisting of $NR^{11}R^{12}$; cyano, nitro, —C(=O)—C≡C—$R^2$; —X—C(=O)—CHR$^1$—C(=O)—$R^2$, or —C(=O)—CR$^1$=CR$^2$—NR$^4$R$^5$; halogen; $C_{1-20}$alkyl; $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; heteroaryl$C_{1-20}$alkyl; halo$C_{1-20}$alkyl; halo$C_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; cyano; —CO$_2$R$^{10}$; —C(O)NR$^{11}$R$^{12}$; and —C(O)R$^9$.

21. The composition according to any one of statements 1 to 2 and 4 to 20, wherein said at least one compound B is an amine compound having a functionality of at least 2 and comprising at least one group selected from the group comprising $C_{5-20}$alkyl, $C_{5-20}$alkenyl; $C_{5-20}$alkynyl; $C_{6-12}$aryl, $C_{5-8}$cycloalkyl; $C_{6-12}$aryl$C_{1-20}$alkyl; $C_{3-8}$cycloalkyl$C_{1-20}$alkyl; hetero$C_{5-20}$alkyl; heterocyclyl; heterocyclyl$C_{1-20}$alkyl; heteroaryl; and heteroaryl$C_{1-20}$alkyl;
wherein said $C_{5-20}$alkyl, $C_{5-20}$alkenyl, $C_{5-20}$alkynyl, $C_{5-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;
wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{5-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or S(O)$_2$;
wherein said $C_{5-20}$alkyl, $C_{5-20}$alkenyl, $C_{5-20}$alkynyl, $C_{6-12}$aryl, $C_{5-8}$cycloalkyl, $C_{6-12}$aryl$C_{1-20}$alkyl, hetero$C_{5-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^{16}$; each $Z^{16}$ is independently selected from the group consisting of $NR^{11}R^{12}$; cyano, nitro, —C(=O)—C≡C—$R^2$; —X—C(=O)—CHR$^1$—C(=O)—$R^2$, or —C(=O)—CR$^1$=CR$^2$—NR$^4$R$^5$; halogen; $C_{1-20}$alkyl; $C_{5-20}$alkenyl, $C_{5-20}$alkynyl, $C_{6-12}$aryl, $C_{5-8}$cycloalkyl, $C_{6-12}$aryl$C_{1-20}$alkyl, hetero$C_{5-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; cyano; —CO$_2$R$^{10}$; —C(O)NR$^{11}$R$^{12}$; and —C(O)R$^9$.

22. The composition according to any one of statements 1 to 2 and 4 to 21, wherein said composition is obtained by contacting at least one compound A, with at least two different compounds B, wherein at least one compound B is an amine compound having an amine functionality of at least 2.

23. The composition according to any one of statements 1 to 2 and 4 to 22, wherein said composition is obtained by contacting at least one compound A, with at least two different compounds B, wherein at least one compound B is an amine compound having an amine functionality of at least 3.

24. Process for preparing a composition according to any one of statements 1 to 2 and 4 to 23, or a compound according to statement 3, comprising contacting at least one compound A comprising at least two functions selected from the group of function of formula —X—C(=O)—CHR$^1$—C(=O)—$R^2$, —C(=O)—C≡C—$R^2$; or —C(=O)—CR$^1$=CR$^2$—NR$^4$R$^5$; wherein at least 25% by weight of compounds A has a functionality ≤5, preferably ≤4, more preferably ≤3, with % by weight relative to the total weight of compounds A;
with at least one compound B comprising at least one —NH$_2$, or —NH$_3^+$ groups, or at least one functional group that generates —NH$_2$ or —NH$_3^+$ in situ, such as —N=C=O;
wherein the ratio R=(sum(functionality of compound A×number of moles of compound A))/(sum(functionality of compound B×number of moles of all compound B)) is <1;

$$\frac{\sum f_a N_a}{\sum f_b N_b} = R < 1$$

wherein $f_a N_a$ denotes the number of moles of —X—C(=O)—CHR$^1$—C(=O)—$R^2$, —C(=O)—C≡C—$R^2$; or —C(=O)—CR$^1$=CR$^2$—NR$^4$R$^5$ functions of the at least one compound A, and $f_b N_b$ denotes the number of moles of —NH$_2$, and/or —NH$_3^+$ groups or the number of moles of functional groups which could generate —NH$_2$ or NH$_3^+$ in situ, such as —N=C=O, of the at least one compound B;

R$^1$ is hydrogen or is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkylC$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;

wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^1$; each Z$^1$ is independently selected from the group consisting of halogen; C$_{1-20}$alkyl; C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$; and R$^4$ is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkylC$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;

wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^4$; each Z$^4$ is independently selected from the group consisting of NR$^{11}$R$^{12}$; halogen; C$_{1-20}$alkyl; C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; cyano; —CO$_2$R$^{10}$; —C(O)NR$^{11}$R$^{12}$; and —C(O)R$^9$;

or wherein the ratio R=(sum(functionality of compound A×number of moles of compound A))/(sum(functionality of compound A×number of moles of compound A)+sum(functionality of compound B×number of moles of all compound B)) is <1;

$$\frac{\sum f_a N_a}{\sum f_a N_a + \sum f_b N_b} = R < 1$$

when R$^1$ and R$^4$ together with the atom to which they are attached form a 5-, 6-, or 7-membered heterocyclyl or heteroaryl; wherein each of said heterocyclyl; or heteroaryl; can be unsubstituted or substituted with one or more Z$^5$; each Z$^5$ is independently selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; halogen; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

wherein f$_a$N$_a$ denotes the number of moles of —X—C(=O)—CHR$^1$—C(=O)—R$^2$, —C(=O)—C≡C—R$^2$; or —C(=O)—CR$^1$=CR$^2$—NR$^4$R$^5$ functions of the at least one compound A, and f$_b$N$_b$ denotes the number of moles of —NH$_2$, and/or —NH$_3^+$ groups or the number of moles of functional groups which could generate —NH$_2$ or NH$_3^+$ in situ, such as —N=C=O, of the at least one compound B; and wherein X is selected from O, NR$^{13}$, or CR$^{14}$R$^{15}$;

R$^2$ is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkylC$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;

wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^2$; each Z$^2$ is independently selected from the group consisting of halogen; C$_{1-20}$alkyl; C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

or wherein R$^2$ and R$^4$ together with the atom to which they are attached form a 5-, 6-, or 7-membered heterocyclyl or heteroaryl; wherein each of said heterocyclyl; or heteroaryl; can be unsubstituted or substituted with one or more Z$^6$; each Z$^6$ is independently selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; halogen; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

R$^5$ is hydrogen or is selected from the group consisting of C$_{1-20}$alkyl, C$_{2-20}$alkenyl; C$_{2-20}$alkynyl; C$_{6-12}$aryl; C$_{3-8}$cycloalkyl; C$_{6-12}$arylC$_{1-20}$alkyl; C$_{3-8}$cycloalkyl C$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;

wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^7$; each Z$^7$ is independently selected from the group consisting of NR$^{11}$R$^{12}$; halogen; C$_{1-20}$alkyl; C$_{2-20}$alkenyl, C$_{2-20}$alkynyl, C$_{6-12}$aryl, C$_{3-8}$cycloalkyl, C$_{6-12}$aryl C$_{1-20}$alkyl, heteroC$_{1-20}$alkyl; heterocyclyl; heteroaryl; C$_{3-8}$cycloalkylC$_{1-20}$alkyl; heterocyclyl C$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; cyano; —CO$_2$R$^{10}$; —C(O)NR$^{11}$R$^{12}$; and —C(O)R$^9$;

each R$^9$ is independently selected from hydroxyl; C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclyl C$_{1-20}$alkyl; and heteroarylC$_{1-20}$alkyl; can be oxidized to form at least one C=O, C=S, N=O, N=S, S=O or S(O)$_2$;

each R$^{10}$ is independently selected from the group consisting of hydrogen, C$_{1-20}$alkyl, C$_{2-20}$alkenyl, C$_{2-20}$alkynyl, C$_{6-12}$aryl, C$_{3-8}$cycloalkyl, C$_{6-12}$aryl C$_{1-20}$alkyl, heteroC$_{1-20}$alkyl, heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

each R$^{11}$ and R$^{12}$ is independently selected from the group consisting of hydrogen; C$_{1-20}$alkyl, C$_{2-20}$alkenyl, C$_{2-20}$alkynyl, C$_{6-12}$aryl, C$_{3-8}$cycloalkyl, C$_{6-12}$aryl C$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

or wherein R$^{11}$ and R$^{12}$ together with the atom to which they are attached form a 5-, 6-, or 7-membered heterocyclyl;

R$^{13}$ is hydrogen or is selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl; can be oxidized to form at least one C=O, C=S, N=O, N=S, S=O or S(O)$_2$;

R$^{14}$ is hydrogen or is selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; heterocyclylC$_{1-20}$alkyl; and heteroarylC$_{1-20}$alkyl;

wherein said C$_{1-20}$alkyl, C$_{2-20}$alkenyl, C$_{2-20}$alkynyl, C$_{6-12}$arylC$_{1-20}$alkyl, heterocyclylC$_{1-20}$alkyl; heteroarylC$_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

$R^{15}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)^2$.

25. Use of a composition according to any one of statements 1 to 2 and 4 to 23, or a compound according to statement 3, as a reactant for preparing a polymer.

26. Use of a composition according to any one of statements 1 to 2 and 4 to 23, or a compound according to statement 3, for the preparation of a permanent polymer network with chemical crosslinks.

27. A Polymer obtained using a composition according to any one of statements 1 to 2 and 4 to 23, or a compound according to statement 3.

28. Polyurethane, polyurea or mixture thereof, obtained by contacting at least one composition according to any one of statements 1 to 2 and 4 to 23, or at least one compound according to statement 3, with at least one isocyanate, optionally in the presence of at least one isocyanate-reactive compound.

29. A material comprising at least one composition according to any one of statements 1 to 2 and 4 to 23, or at least one compound according to statement 3, and at least one component chosen from: polymers, pigments, dyes, fillers, plasticizers, fibers, flame retardants, antioxidants, lubricants, wood, glass, metals.

30. An article comprising the composition according to any one of statements 1 to 2 and 4 to 23, or a compound according to statement 3, or a material according to statement 29.

31. A process for recycling an article according to statement 30, comprising: a) reducing the article into particles by application of mechanical grinding, b) transforming the particles from step a) by applying a mechanical constraint to the particles at a temperature (T) above room temperature.

32. A process for recycling an article according to statement 30, comprising: a) applying a mechanical constraint and optionally a simultaneous increase in temperature to transform the article into an assembly of elemental units, b) cooling the assembly of elemental units.

33. Use of a composition according to any one of statements 1 to 2 and 4 to 23, or at least one compound according to statement 3, or a material according to statement 29, in polymers, membranes, adhesives, foams, sealants, molded articles, films, extruded articles, fibers, polymer based additives, varnishes, paints, coatings, inks, composite material, organic LEDs, organic semiconductors, or conducting organic polymers.

34. A process for reshaping and/or repairing an article according to statement 30, comprising the step of thermally treating the article at a temperature (T) above room temperature.

The present invention also encompasses a composition, this composition resulting from contacting:

at least one compound A comprising at least two functions selected from the group of function of formula —X—C(=O)—CHR$^1$—C(=O)—R$^2$, —C(=O)—C≡C—R$^2$; or —C(=O)—CR$^1$=CR$^2$—NR$^4$R$^5$; wherein at least 25% by weight of compounds A has a functionality ≤5, preferably ≤4, more preferably ≤3, with % by weight based on the total weight of compounds A;

with at least one compound B comprising at least one —NH$_2$, or —NH$_3^+$ groups, or at least one functional group that generates —NH$_2$ or —NH$_3^+$ in situ, such as —N=C=O;

wherein the ratio R=(sum(functionality of compound A×number of moles of compound A))/(sum(functionality of compound B×number of moles of all compound B)) is <1;

$$\frac{\sum f_a N_a}{\sum f_b N_b} = R < 1$$

wherein $f_a N_a$ denotes the number of moles of —X—C(=O)—CHR$^1$—C(=O)—R$^2$, —C(=O)—C≡C—R$^2$; or —C(=O)—CR$^1$=CR$^2$—NR$^4$R$^5$ functions of the at least one compound A, and $f_b N_b$ denotes the number of moles of —NH$_2$, and/or —NH$_3^+$ groups or the number of moles of functional groups which could generate —NH$_2$ or NH$_3^+$ in situ, such as —N=C=O, of the at least one compound B;

$R^1$ is hydrogen or is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^1$; each $Z^1$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$; and R$^4$ is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkylC$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;

wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^4$; each Z$^4$ is independently selected from the group consisting of NR$^{11}$R$^{12}$; halogen; C$_{1-20}$alkyl; C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; cyano; —CO$_2$R$^{10}$; —C(O)NR$^{11}$R$^{12}$; and —C(O)R$^9$;

or wherein the ratio R=(sum(functionality of compound A×number of moles of compound A))/(sum(functionality of compound A×number of moles of compound A)+sum(functionality of compound B×number of moles of all compound B)) is <1;

$$\frac{\sum f_a N_a}{\sum f_a N_a + \sum f_b N_b} = R < 1$$

when R$^1$ and R$^4$ together with the atom to which they are attached form a 5-, 6-, or 7-membered heterocyclyl or heteroaryl; wherein each of said heterocyclyl; or heteroaryl; can be unsubstituted or substituted with one or more Z$^5$; each Z$^5$ is independently selected from the group consisting of C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; halogen; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O) NR$^{11}$R$^{12}$; and —C(O)R$^9$;

wherein f$_a$N$_a$ denotes the number of moles of —X—C(=O)—CHR$^1$—C(=O)—R$^2$, —C(=O)—C≡C—R$^2$; or —C(=O)—CR$^1$=CR$^2$—NR$^4$R$^5$ functions of the at least one compound A, and f$_b$N$_b$ denotes the number of moles of —NH$_2$, and/or —NH$_3^+$ groups or the number of moles of functional groups which could generate —NH$_2$ or NH$_3^+$ in situ, such as —N=C=O, of the at least one compound B;

and wherein X, R$^2$, and R$^5$ have the same meaning as that defined herein.

The present invention also encompasses, a compound comprising at least two units and at most 5 units of formula (I), (II), and/or (III);

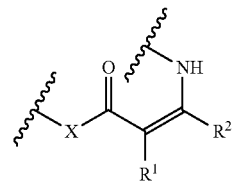
(I)

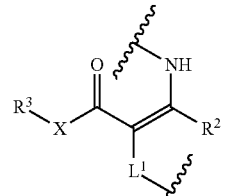
(II)

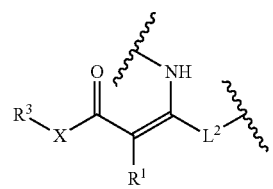
(III)

wherein X, R$^1$, R$^2$, R$^3$, L$^1$ and L$^2$ have the same meaning as that defined herein.

In some preferred embodiments, the compositions or the compounds of this invention are prepared using condensation reaction between acetoacetates and amines, preferably di-, tri- or polyamines. Bis-acetoacetate monomers can easily be prepared from readily available diol monomers, (a) J. S. Witzeman, W. D. Nottingham, The Journal of Organic Chemistry 1991, 56, 1713; b) R. J. Clemens, J. A. Hyatt, The Journal of Organic Chemistry 1985, 50, 2431).

Non-limiting examples of suitable acetoacetates comprise compounds as exemplified below:

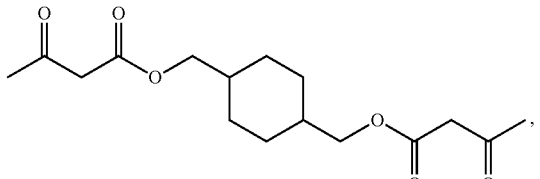

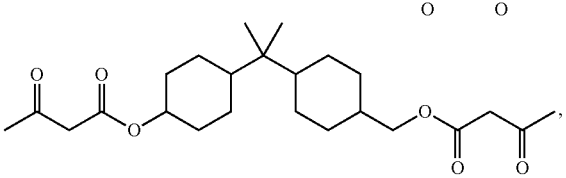

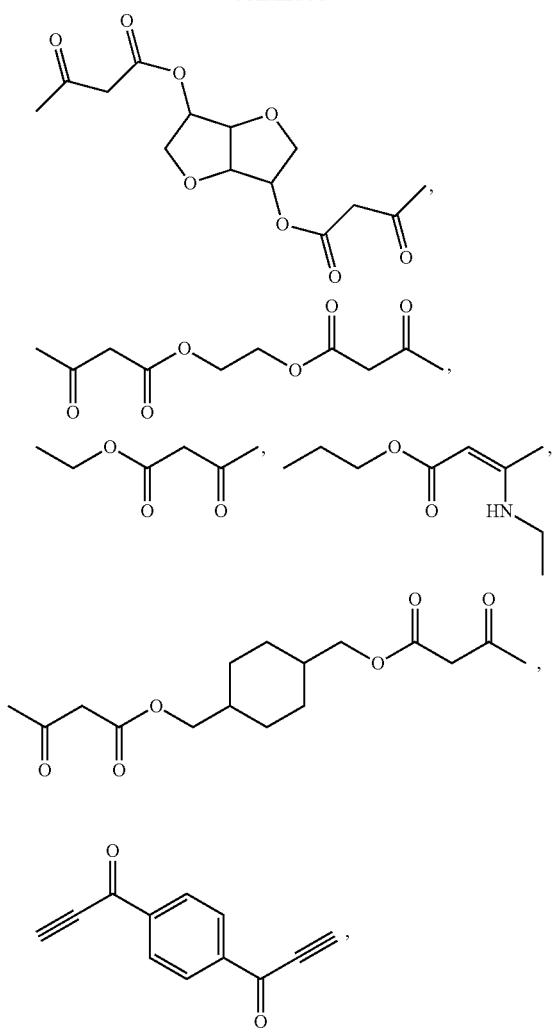

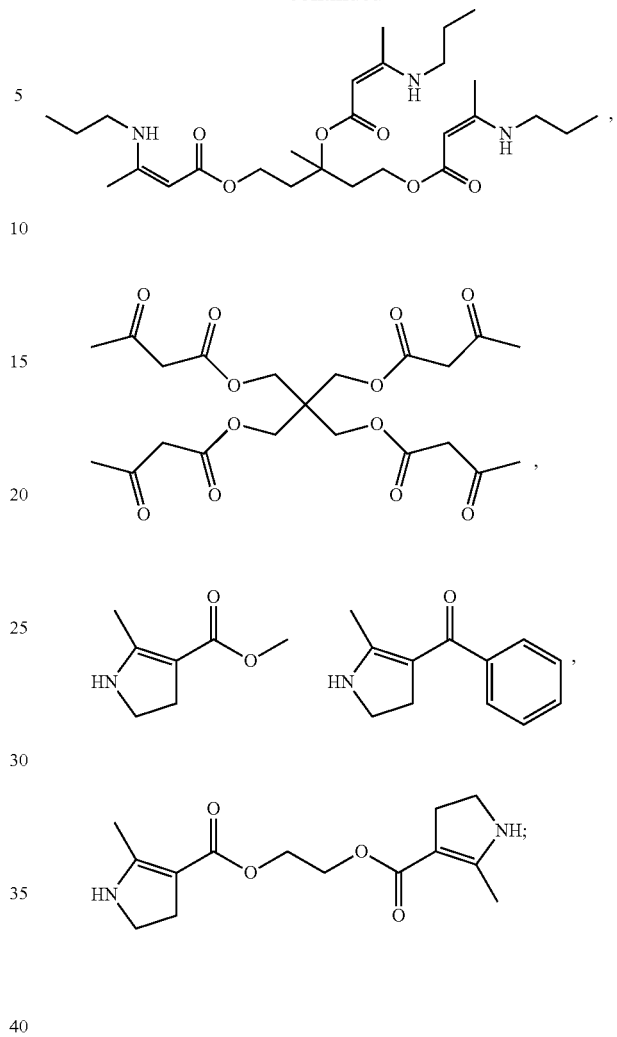

acetoacetylated derivative of alcohol, such as acetoacetylated derivative of Pripol™ 2030 (from Croda).

For example, compound A can be an acetoacetylated derivative of an alcohol selected from the group comprising aliphatic polyols, preferably aliphatic polyols without ester functions, such as cyclohexane dimethanol, 4,4'-Isopropylidenedicyclohexanol, 1,2-benzene dimethanol, 2,2'-biphenyl dimethanol, Trans-1,2-cyclohexanediol; 1,4-Bis(2-hydroxyisopropyl)benzene; Cis-cyclopentanediol; 3,3-Dimethyl-1,2-butanediol; 2,4-Dimethyl-2,4-pentanediol; 1,3-Dioxane-5,5-dimethanol; trans-1,4-Dioxane-2,3-diol; 2,2,4,4-Tetramethyl-1,3-cyclobutanediol; hydrobenzoin, hydroquinone bis(2-hydroxyethyl) ether; 3-Methoxy-1,2-propanediol; 3-Morpholino-1,2-propanediol; 2,2'-(o-Phenylenedioxy)diethanol; 2,2,4-Trimethyl-1,3-pentanediol 97%; 4,4'-Isopropylidenebis[2-(2,6-dibromophenoxy)ethanol]; D-isosorbide; Pripol 2033; Di(trimethylolpropane); 3-methyl-1,3,5-pentanetriol technical grade; Triisopropanolamine; pentaerythritol; polyvinyl alcohol and copolymers thereof; dipentaerythritol.

Non-limiting examples of suitable alcohols are shown in Tables A, and B.

TABLE A

| Name | CAS |
|---|---|
| Aliphatic C2-Cx - diol | / |
| cyclohexane dimethanol | 105-08-8 |
| 4,4'-Isopropylidenedicyclohexanol or hydrogenated bisphenol A + thereof such as HBP-E, C, A, F, BP, FC, Z | 80-04-6; 71402-84-1; 93882-53-2 |
| 1,2-benzene dimethanol | 612-14-6 |
| 2,2'-biphenyl dimethanol | 3594-90-9 |
| Trans-1,2-cyclohexanediol | 1460-57-7 |
| 1,4-Bis(2-hydroxyisopropyl)benzene | 2948-46-1 |
| Cis-cyclopentanediol | 5057-98-7 |
| 3,3-Dimethyl-1,2-butanediol | 59562-82-2 |
| 2,4-Dimethyl-2,4-pentanediol | 24892-49-7 |
| 1,3-Dioxane-5,5-dimethanol | 6228-25-7 |
| trans-1,4-Dioxane-2,3-diol | 4845-50-5 |

TABLE A-continued
| Name | CAS | |
|---|---|---|
| 2,2,4,4-Tetramethyl-1,3-cyclobutanediol, mixture of isomers | 3010-96-6 | 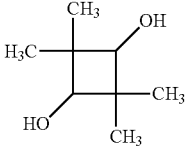 |
| hydrobenzoin | 492-70-6 | 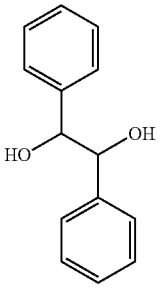 |
| Hydroquinone bis(2-hydroxyethyl) ether | 104-38-1 | 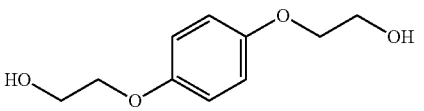 [SMILES: OCCOc1ccc(OCCO)cc1] |
| 3-Methoxy-1,2-propanediol 98% | 623-39-2 | 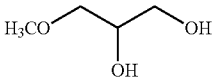 |
| 3-Morpholino-1,2-propanediol | 6425-32-7 | 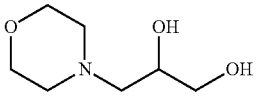 [SMILES: OCC(O)CN1CCOCC1] |
| 2,2'-(o-Phenylenedioxy)diethanol 97% | 10234-40-9 | 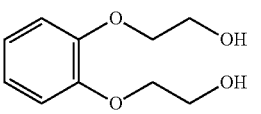 [SMILES: OCCOc1ccccc1OCCO] |
| 2,2,4-Trimethyl-1,3-pentanediol 97% | 144-19-4 | 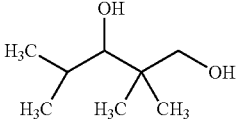 |
| 4,4'-Isopropylidenebis[2-(2,6-dibromophenoxy)ethanol] | 4162-45-2 | 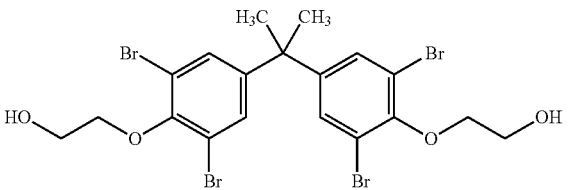 [SMILES: CC(C)(c1cc(Br)c(OCCO)c(Br)c1)c1cc(Br)c(OCCO)c(Br)c1] |
Bio based / renewable carbon
| | | |
|---|---|---|
| D-isosorbide | 652-67-5 | 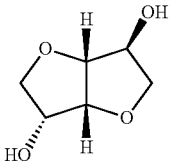 |

TABLE A-continued

| Name | CAS | |
|---|---|---|
| Pripol 2033 | | (structure shown) |

TABLE B

| Name | CAS | |
|---|---|---|
| Di(trimethylolpropane) | 23235-61-2 | (structure shown) |
| 3-Methyl-1,3,5-pentanetriol technical grade, 80% | 7564-64-9 | (structure shown) |
| Triisopropanolamine | 122-20-3 | (structure shown) |
| pentaerythritol | 115-77-5 | (structure shown) |
| Polyvinyl alcohol and copolymers | | (structure shown) |
| Poly(vinyl alcohol-co-ethylene) | | (structure shown) |
| dipentaerythritol | | (structure shown) |

Combination with various commercial available polyamine monomers, a broad range of polyvinylogous urethane, amine or urea polymers could be prepared which can be tuned for material properties by variation of monomer type and stoichiometry. Polymers with good mechanical properties and a high Tg can therefore be obtained, Preferably, compound B is an amine compound and can be selected from the group comprising diamines, triamines and polyamines. In some embodiment, compound B is an amine such as those used as isocyanate precursor, such as dialkyl amines of the formula $R^{30}$—$NH_2$, in which $R^{30}$ can be optionally substituted $C_{1-20}$alkyl, $C_{3-8}$cycloalkyl, $C_{6-12}$aryl, $C_{6-12}$aryl$C_{1-20}$alkyl; hetero$C_{1-20}$alkyl, heterocyclyl, heteroaryl.

Compound B may be chosen, for example, from aliphatic amines such as tris(2-aminoethyl)amine, ethylenediamine, tetramethylenediamine, pentamethylenediamine, hexamethylenediamine, diethylenetriamine, triethylenetetramine, tetraethylenepentamine, dihexylenetriamine, cadaverine, putrescine, hexanediamine, spermine, isophorone diamine, dimerised fatty diamine (such as are available commercially under the trade name "Priamine" from Croda International and the trade name "Versamine" from Cognis Corporation) and also aromatic and benzylic amines such as m-xylylene diamine; phenylenediamine, diaminodiphenylmethane, diaminodiphenyl sulfone and methylenebischlorodiethylaniline. Non-limiting examples include m-xylylene diamine; p-xylylene diamine; 1,3-Cyclohexanebis(methylamine), mixture of isomers; 1,2-Diaminocyclohexane; 1,5-Diamino-2-methylpentane; 4,9-Dioxa-1,12-dodecanediamine; Dytek® EP diamine; 2,2-Dimethyl-1,3-propanediamine; 2,2'-(Ethylenedioxy)bis(ethylamine); Tris(2-aminoethyl)

amine; 4,4'-Methylenebis(cyclohexylamine); 4,7,10-Trioxa-1,13-tridecanediamine; all jeffamines (commercially available from Huntsman).

Non-limiting examples of suitable compound B are shown in Table C.

therefore controlled by increasing or decreasing the speed of exchange reaction. Acid can increase the speed of the exchange reaction and base can slow down the exchange reaction.

TABLE C

| Name | CAS | structure |
|---|---|---|
| Aliphatic amines C2-Cx | | |
| m-xylylene diamine | 1477-55-0 | $H_2N$–CH$_2$–C$_6$H$_4$–CH$_2$–$NH_2$ (meta) |
| p-xylylene diamine | 539-48-0 | $H_2N$–CH$_2$–C$_6$H$_4$–CH$_2$–$NH_2$ (para) |
| 1,3-Cyclohexanebis(methylamine), mixture of isomers | 2579-20-6 | 1,3-cyclohexane-bis(CH$_2NH_2$) |
| 1,2-Diaminocyclohexane, mixture of cis and trans technical grade, 99% | 694-83-7 | 1,2-cyclohexane-di-$NH_2$ |
| 1,5-Diamino-2-methylpentane 99% | 15520-10-2 | $H_2N$–CH$_2$–CH(CH$_3$)–CH$_2$–CH$_2$–CH$_2$–$NH_2$ |
| 4,9-Dioxa-1,12-dodecanediamine | 7300-34-7 | $H_2N$–(CH$_2$)$_3$–O–(CH$_2$)$_4$–O–(CH$_2$)$_3$–$NH_2$ |
| Dytek® EP diamine 98% | 589-37-7 | $H_3C$–CH(NH$_2$)–CH$_2$–CH$_2$–$NH_2$ |
| 2,2-Dimethyl-1,3-propanediamine 99% | 7328-91-8 | $H_2N$–CH$_2$–C(CH$_3$)$_2$–CH$_2$–$NH_2$ |
| 2,2'-(Ethylenedioxy)bis(ethylamine) 98% | 29-59-9 | $H_2N$–CH$_2$CH$_2$–O–CH$_2$CH$_2$–O–CH$_2$CH$_2$–$NH_2$ |
| 4,4'-Methylenebis(cyclohexylamine) technical grade, 95% | 1761-71-3 | $H_2N$–C$_6$H$_{10}$–CH$_2$–C$_6$H$_{10}$–$NH_2$ |
| 4,7,10-Trioxa-1,13-tridecanediamine 97% | 4246-51-9 | $H_2N$–(CH$_2$)$_3$–O–(CH$_2$)$_2$–O–(CH$_2$)$_2$–O–(CH$_2$)$_3$–$NH_2$ |
| Priamine | | |
| All jeffamines | | |
| Tris(2-aminoethyl)amine 96% | 4097-89-6 | N(CH$_2$CH$_2NH_2$)$_3$ |

The composition can be prepared in the presence of a catalyst, or an anticatalyst, or without any catalyst. The speed of stress-relaxation of the polymeric network can be In an embodiment, acids can be selected from acetic acid, trifluoracetic acid, etc. . . . ; and bases can be selected from DBU, dibutylamine etc. . . . Organometallic catalyst can be used. In this embodiments, the catalyst can comprises an element selected from the group comprising tin, iron, lead, bismuth, mercury, titanium, hafnium, zirconium, and combinations thereof. In certain embodiments, the catalyst comprises a tin catalyst. Suitable tin catalysts, for purposes of the present invention, may be selected from tin(II) salts of organic carboxylic acids, e.g. tin(II) acetate, tin(II) octoate, tin(III) ethylhexanoate and tin(II) laurate. In some embodiments, the organometallic catalyst comprises dibutyltin dilaurate, which is a dialkyltin(IV) salt of an organic carboxylic acid. Specific examples of suitable organometallic catalyst, e.g. dibutyltin dilaurates, for purposes of the present invention, are commercially available from Air Products and Chemicals, Inc. under the trademark of DABCO®. The organometallic catalyst can also comprise other dialkyltin (IV) salts of organic carboxylic acids, such as dibutyltin diacetate, dibutyltin maleate and dioctyltin diacetate. Non-limiting examples of other suitable catalysts, may be selected from the group comprising iron(II) chloride; zinc chloride; lead octoate; tris(dialkylaminoalkyl)-s-hexahydrotriazines including tris(N,N-dimethylaminopropyl)-s-hexahydrotriazine; tetraalkylammonium hydroxides including tetramethylammonium hydroxide; alkali metal hydroxides including sodium hydroxide and potassium hydroxide; alkali metal alkoxides including sodium methoxide and potassium isopropoxide; and alkali metal salts of long-chain fatty acids having from 10 to 20 carbon atoms and/or lateral OH groups; triethylamine, N,N,N',N'-tetramethylethylenediamine, N,N-dimethylaminopropylamine, N,N,N',N',N''-pentamethyldipropylenetriamine, tris(dimethylaminopropyl)amine, N,N-dimethylpiperazine, tetramethylimino-bis (propylamine), dimethylbenzylamine, trimethyl amine, triethanolamine, N,N-diethyl ethanolamine, N-methylpyrrolidone, N-methylmorpholine, N-ethylmorpholine, bis(2-dimethylamino-ethyl)ether, N,N-dimethylcyclohexylamine (DMCHA), N,N,N',N',N''-pentamethyldiethylenetriamine, 1,2-dimethylimidazole, 3-(dimethylamino) propylimidazole; N,N,N-dimethylaminopropylhexahydrotriazine, potassium, potassium acetate, N,N,N-trimethyl isopropyl amine/ formate, and combinations thereof. It is to be appreciated that the catalyst may include any combination of two or more of the aforementioned catalysts.

Preferably, the composition is prepared without any catalysts.

The present invention encompasses also materials obtained by contacting
at least one compound A comprising at least two functions selected from the group of function of formula —X—C (=O)—CHR$^1$—C(=O)—R$^2$, —C(=O)—C≡C—R$^2$; or —C(=O)—CR$^1$=CR$^2$—NR$^4$R$^5$; wherein at least 25% by weight of compound A has a functionality <5, with % by weight based on the total weight of compounds A;
with at least one compound B comprising at least one —NH$_2$, or —NH$_3^+$ groups, or at least one functional group that generates —NH$_2$ or —NH$_3^+$ in situ, such as —N=C=O;

and wherein $$\frac{\sum f_a N_a}{\sum f_b N_b} = R < 1;$$

or wherein $$\frac{\sum f_a N_a}{\sum f_a N_a + \sum f_b N_b} = R < 1$$

when R$^1$ and R$^4$ together with the atom to which they are attached form a 5-, 6-, or 7-membered heterocyclyl or heteroaryl;
wherein $f_a N_a$ denotes the number of moles of —X—C (=O)—CHR$^1$—C(=O)—R$^2$, —C(=O)—C≡C—R$^2$; or —C(=O)—CR$^1$=CR$^2$—NR$^4$R$^5$ functions of the at least one compound A, and $f_b N_b$ denotes the number of moles of —NH$_2$, and/or —NH$_3^+$ groups or the number of moles of functional groups which could generate —NH$_2$ or NH$_3^+$ in situ, such as —N=C=O, of the at least one compound B.

The present invention also encompasses a compound comprising at least two units and at most 5 units of formula (I), (II), and/or (III); and their use for preparing permanent polymer network with chemical crosslinks.

For example, compounds comprising at least three units of formula (I) can be used in the presence of an alcohol to prepare a polymer network, as schematically shown in Scheme A.

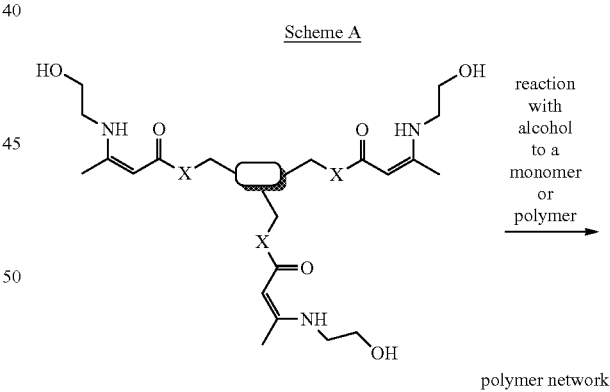

Scheme A polymer network

Non-limiting examples of suitable use of compounds or compositions according to the present invention for the preparation of polyurethane are illustrated in Scheme B, wherein an acetoacetate compound can be reacted with either an aminoalcohol or a polyamine to produce the corresponding vinylogous urethane which can then be contacted with at least one isocyanate compound to prepare a polyurethane.

Scheme B

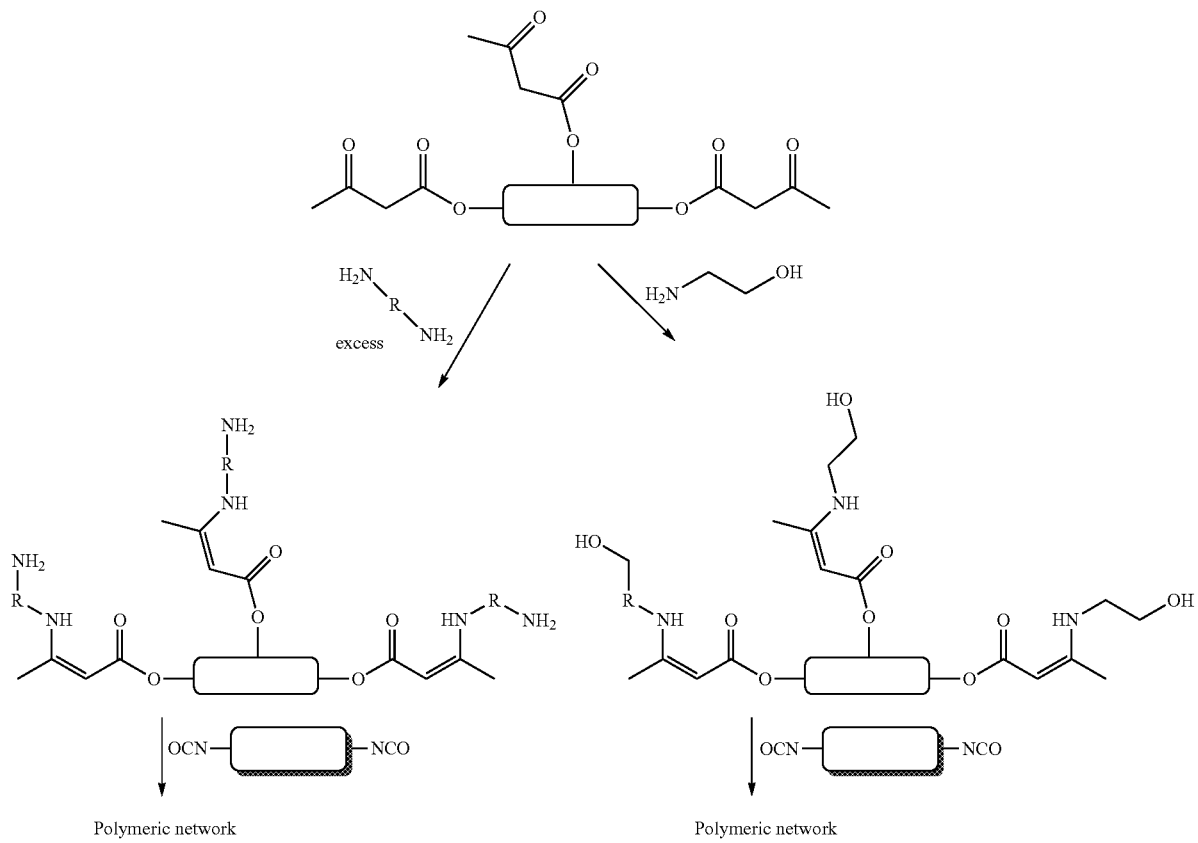

The present invention also encompasses polyurethane, polyurea or mixture thereof, obtained by contacting at least one composition according to the invention, or at least one compound according to the invention, with at least one isocyanate, optionally in the presence of at least one isocyanate-reactive compound.

The at least one isocyanate can be an isocyanate-containing prepolymer. As used herein, the term "isocyanate-containing prepolymer" refers to a prepolymer comprising at least one isocyanate-N=C=O group, whereby the isocyanate group may be a terminating group. Preferably, the isocyanate group is a terminating group. The isocyanate-containing prepolymer can be obtained by reacting at least one isocyanate with at least one isocyanate-reactive compound.

The at least one isocyanate can be selected from the group comprising aromatic, cycloaliphatic, heterocyclic, araliphatic or aliphatic organic isocyanates. Suitable isocyanates include also polyisocyanates.

Suitable polyisocyanates comprise polyisocyanates of the type $R^a$—$(NCO)_x$ with x being at least 1 and $R^a$ being an aromatic or aliphatic group, such as diphenylmethane, toluene, dicyclohexylmethane, hexamethylene, or a similar polyisocyanate. Preferably, said polyisocyanate comprises at least two isocyanate groups.

Non-limiting examples of organic polyisocyanates include diisocyanates, particularly aromatic diisocyanates, and isocyanates of higher functionality. Non-limiting examples of organic polyisocyanates which may be used in the formulation of the present invention include aliphatic isocyanates such as hexamethylene diisocyanate; and aromatic isocyanates such as diphenylmethane diisocyanate (MDI) in the form of its 2,4'-, 2,2'- and 4,4'-isomers and mixtures thereof, the mixtures of diphenylmethane diisocyanates (MDI) and oligomers thereof; m- and p-phenylene diisocyanate, tolylene-2,4- and tolylene-2,6-diisocyanate (also known as toluene diisocyanate, and referred to as TDI, such as 2,4 TDI and 2,6 TDI) in any suitable isomer mixture, chlorophenylene-2,4-diisocyanate, naphthylene-1,5-diisocyanate, diphenylene-4,4'-diisocyanate, 4,4'-diisocyanate-3,3'-dimethyl-diphenyl, 3-methyl-diphenylmethane-4,4'-diisocyanate and diphenyl ether diisocyanate; and cycloaliphatic diisocyanates such as cyclohexane-2,4- and -2,3-diisocyanate, 1-methylcyclohexyl-2,4- and -2,6-diisocyanate and mixtures thereof and bis-(isocyanatocyclohexyl)methane (e.g. 4,4'-diisocyanatodicyclohexylmethane (H12MDI)), triisocyanates such as 2,4,6-triisocyanatotoluene and 2,4,4-triisocyanatodiphenylether, isophorone diisocyanate (IPDI), butylene diisocyanate, trimethylhexamethylene diisocyanate, isocyanatomethyl-1,8-octane diisocyanate, tetramethylxylene diisocyanate (TMXDI), 1,4-cyclohexanediisocyanate (CDI), and tolidine diisocyanate (TODI); any suitable mixture of these polyisocyanates, and any suitable mixture of one or more of these polyisocyanates with MDI in the form of its 2,4'-, 2,2'- and 4,4'-isomers and mixtures thereof, the mixtures of diphenylmethane diisocyanates (MDI) and oligomers thereof, and reaction products of polyisocyanates (e.g. polyisocyanates as set out above).

The polyisocyanates that can be used in the present invention may be mixtures of said isocyanates, polymeric MDI, as well as prepolymers of these isocyanates.

The polymeric methylene diphenyl diisocyanate can be any mixture of MDI (as defined herein above) and higher homologues of formula (A):

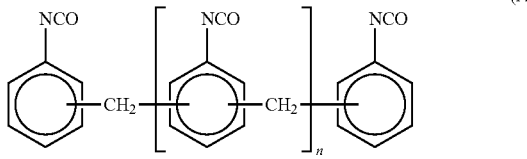

(A)

wherein n is an integer which can be from 1 to 10, preferably from 1 to 5.

In some embodiments, the at least one isocyanate-reactive compound may be a component containing isocyanate-reactive hydrogen atoms. As used herein, the term "isocyanate-reactive hydrogen atom" refers to compounds that contain acidic hydrogen atoms, which make the compounds that bear them, susceptible to electrophilic attack by an isocyanate group. Examples of suitable isocyanate-reactive compounds containing isocyanate-reactive hydrogen atoms include polyols such as glycols or even relatively high molecular weight polyether polyols and polyester polyols, thiols (mercaptans), carboxylic acids such as polybasic acids, amines, polyamines, components comprising at least one alcohol group and at least one amine group, such as polyaminepolyols, urea and amides.

In some embodiments, said at least one isocyanate-reactive compound comprises at least one OH group. In some embodiments, the at least one isocyanate reactive compound is selected from the group comprising hydroxyl terminated polyether (polyether polyols); polyols such as glycols; hydroxyl terminated polyester (polyester polyols); hydroxyl terminated polycarbonate and mixtures thereof, all of which are well known to those skilled in the art.

In some embodiments, the at least one isocyanate reactive compound is selected from the group comprising hydroxyl terminated polyethers (polyether polyols); polyols such as glycols; hydroxyl terminated polyesters (polyester polyols); hydroxyl terminated polycarbonates and mixtures thereof.

Suitable hydroxyl terminated polyester (polyester polyols), can be produced by (1) an esterification reaction of one or more glycols with one or more dicarboxylic acids or anhydrides or (2) by transesterification reaction, i.e. the reaction of one or more glycols with esters of dicarboxylic acids. Mole ratios generally in excess of more than one mole of glycol to acid are preferred so as to obtain linear chains having a preponderance of terminal hydroxyl groups. Suitable polyester also include various lactones such as polycaprolactone typically made from caprolactone and a bifunctional initiator such as diethylene glycol. The dicarboxylic acids of the desired polyester can be aliphatic, cycloaliphatic, aromatic, or combinations thereof. Suitable dicarboxylic acids which can be used alone or in mixtures generally have a total of from 4 to 15 carbon atoms and include: succinic, glutaric, adipic, pimelic, suberic, azelaic, sebacic, dodecanedioic, isophthalic, terephthalic, cyclohexane dicarboxylic, and the like. Anhydrides of the above dicarboxylic acids such as phthalic anhydride, tetrahydrophthalic anhydride, or the like, can also be used. The glycols which are reacted to form a desirable polyester intermediate can be aliphatic, aromatic, or combinations thereof, and have a total of from 2 to 12 carbon atoms, and include ethylene glycol, 1,2-propanediol, 1,3-propanediol, 1,3-butanediol, 1,4-butanediol, 1,5-pentanediol, 1,6-hexanediol, 2,2-dimethyl-1,3-propanediol, 1,4-cyclohexanedimethanol, decamethylene glycol, dodecamethylene glycol, and the like.

Suitable hydroxyl terminated polyethers are preferably polyether polyols derived from a diol or polyol having a total of from 2 to 15 carbon atoms, preferably an alkyl diol or glycol which is reacted with an ether comprising an alkylene oxide having from 2 to 6 carbon atoms, typically ethylene oxide or propylene oxide or mixtures thereof. For example, hydroxyl functional polyether can be produced by first reacting propylene glycol with propylene oxide followed by subsequent reaction with ethylene oxide. Primary hydroxyl groups resulting from ethylene oxide are more reactive than secondary hydroxyl groups and thus are preferred. Useful commercial polyether polyols include poly(ethylene glycol) comprising ethylene oxide reacted with ethylene glycol, poly(propylene glycol) comprising propylene oxide reacted with propylene glycol, poly(tetramethylglycol) (PTMG) comprising water reacted with tetrahydrofuran (THF). Polyether polyols further include polyamide adducts of an alkylene oxide and can include, for example, ethylenediamine adduct comprising the reaction product of ethylenediamine and propylene oxide, diethylenetriamine adduct comprising the reaction product of diethylenetriamine with propylene oxide, and similar polyamide type polyether polyols. Copolyethers can also be utilized in the current invention. Typical copolyethers include the reaction product of glycerol and ethylene oxide or glycerol and propylene oxide.

Suitable hydroxyl terminated polycarbonates can be prepared by reacting a glycol with a carbonate. U.S. Pat. No. 4,131,731 is hereby incorporated by reference for its disclosure of hydroxyl terminated polycarbonates and their preparation. Such polycarbonates are preferably linear and have terminal hydroxyl groups with essential exclusion of other terminal groups. The reactants are glycols and carbonates. Suitable glycols are selected from cycloaliphatic and aliphatic diols containing 4 to 40carbon atoms, and from polyoxyalkylene glycols containing 2 to 20 alkoxy groups per molecule with each alkoxy group containing 2 to 4 carbon atoms. Suitable diols include but are not limited to aliphatic diols containing 4 to 12 carbon atoms such as butanediol-1,4, pentanediol-1,4, neopentyl glycol, hexanediol-1,6, 2,2,4-trimethylhexanedion-1,6, decanediol-1,10, hydrogenated dilinoleylglycol, hydrogenated diolelylglycol; and cycloaliphatic diols such as cyclohexanediol-1,3, dimethylolcyclohexane-1,4, cyclohexanediol-1,4, dimethylolcyclohexane-1,3, 1,4-endomethylene-2-hydroxy-5-hydroxymethyl cyclohexane, and polyalkylene glycols. The diols used in the reaction may be a single diol or a mixture of diols depending on the properties desired in the finished product. Non-limiting examples of suitable carbonates include ethylene carbonate, trimethylene carbonate, tetramethylene carbonate, 1,2-propylene carbonate, 1,2-butylene carbonate, 2,3-butylene carbonate, 1,2-ethylene carbonate, 1,3-pentylene carbonate, 1,4-pentylene carbonate, 2,3-pentylene carbonate and 2,4-pentylene carbonate. Also suitable are dialkylcarbonates, cycloaliphatic carbonates, and diarylcarbonates. The dialkylcarbonates can contain 2 to 5 carbon atoms in each alkyl group and specific examples thereof are diethylcarbonate and dipropylcarbonate. Cycloaliphatic carbonates, especially dicycloaliphatic carbonates, can contain 4 to 7 carbon atoms in each cyclic structure, and there can be one or two of such structures. When one group is cycloaliphatic, the other can be either alkyl or aryl. On the other hand, if one group is aryl, the other can be alkyl or cycloaliphatic. Examples of diarylcarbonates, which can contain 6 to 20 carbon atoms in each aryl group, are diphenylcarbonate, ditolylcarbonate and dinaphthylcarbonate.

In some embodiments, the isocyanate-reactive component can be reacted with the isocyanate, along with extender glycol. Non-limiting examples of suitable extender glycols (i.e., chain extenders) include lower aliphatic or short chain glycols having from about 2 to about 10 carbon atoms and include, for instance, ethylene glycol, diethylene glycol, propylene glycol, dipropylene glycol, 1,4-butanediol, 1,6-hexanediol, 1,3-butanediol, 1,5-pentanediol, 1,4-cyclohexanedimethanol, hydroquinone di(hydroxyethyl)ether, neopentylglycol, and the like.

The polyurethane can be prepared in the presence of a catalyst. In some embodiments, the catalyst is an organometallic catalyst. In these embodiments, the catalyst comprises an element selected from the group comprising tin, iron, lead, bismuth, mercury, titanium, hafnium, zirconium, and combinations thereof. In certain embodiments, the catalyst comprises a tin catalyst. Suitable tin catalysts, for purposes of the present invention, may be selected from tin(II) salts of organic carboxylic acids, e.g. tin(II) acetate, tin(II) octoate, tin(II) ethylhexanoate and tin(II) laurate. In some embodiments, the organometallic catalyst comprises dibutyltin dilaurate, which is a dialkyltin(IV) salt of an organic carboxylic acid. Specific examples of suitable organometallic catalyst, e.g. dibutyltin dilaurates, for purposes of the present invention, are commercially available from Air Products and Chemicals, Inc. under the trademark of DABCO®. The organometallic catalyst can also comprise other dialkyltin(IV) salts of organic carboxylic acids, such as dibutyltin diacetate, dibutyltin maleate and dioctyltin diacetate.

Non-limiting examples of other suitable catalysts, may be selected from the group comprising iron(II) chloride; zinc chloride; lead octoate; tris(dialkylaminoalkyl)-s-hexahydrotriazines including tris(N,N-dimethylaminopropyl)-s-hexahydrotriazine; tetraalkylammonium hydroxides including tetramethylammonium hydroxide; alkali metal hydroxides including sodium hydroxide and potassium hydroxide; alkali metal alkoxides including sodium methoxide and potassium isopropoxide; and alkali metal salts of long-chain fatty acids having from 10 to 20 carbon atoms and/or lateral OH groups; triethylamine, N,N,N',N'-tetramethylethylenediamine, N,N-dimethylaminopropylamine, N,N,N',N',N''-pentamethyldipropylenetriamine, tris(dimethylaminopropyl)amine, N,N-dimethylpiperazine, tetramethylimino-bis(propylamine), dimethylbenzylamine, trimethyl amine, triethanolamine, N,N-diethyl ethanolamine, N-methylpyrrolidone, N-methylmorpholine, N-ethylmorpholine, bis(2-dimethylamino-ethyl)ether, N,N-dimethylcyclohexylamine (DMCHA), N,N,N',N',N''-pentamethyldiethylenetriamine, 1,2-dimethylimidazole, 3-(dimethylamino) propylimidazole; N,N,N-dimethylaminopropylhexahydrotriazine, potassium, potassium acetate, N,N,N-trimethyl isopropyl amine/formate, and combinations thereof. It is to be appreciated that the catalyst component may include any combination of two or more of the aforementioned catalysts.

The polyurethane can be for example prepared by contacting at least one isocyanate, with a vinylogous urethane composition according to the invention. In some embodiments, any polyol can be directly transformed into a vinylogous urethane-containing polyol using for example two synthetic operations as shown in Scheme C: an esterification with a bulk chemical acetoacetic, and a condensation reaction with an aminoalcohol. Thus, vinylogous urethanes can be used into almost any existing formulation for polyurethane materials. Furthermore, the nature and number of vinylogous urethanes can be adapted at will.

Scheme C Synthesis of vinylogous urethane containing polyol monomers, and their use in the production of covalent adaptable PU networks (CAPU).

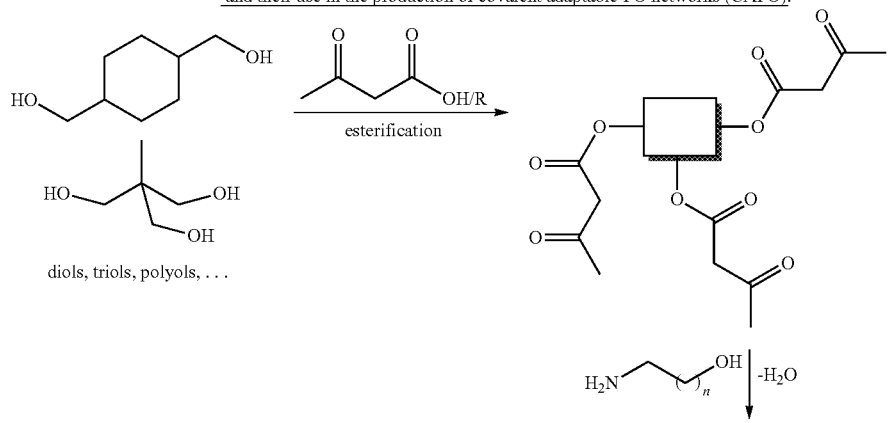

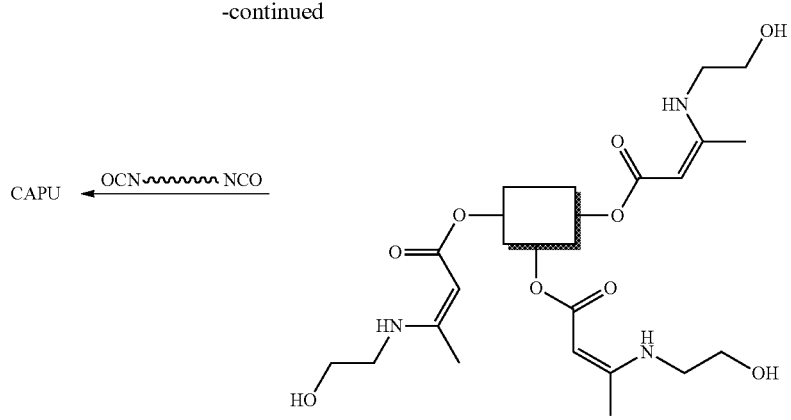

For example isocyanate end capped prepolymers of different nature (polyether, polyester) can be used to prepare the polyurethane network.

The invention also encompasses a formulation comprising the composition according to the first aspect of the invention, at least one polyisocyanate, and optionally at least one isocyanate-reactive compound and/or the adduct of said at least one isocyanate and optionally at least one isocyanate-reactive compound.

The invention encompasses a composition comprising the polyurethane, polyurea, or mixture thereof, according to the invention. In some embodiments, said composition or formulation further comprises one or more additives selected from the group comprising fillers, adhesion promoters, moisture scavengers, plasticizers, UV stabilizers, thixotropic agents or combinations thereof.

The present invention also encompasses the use of a polyurethane, polyurea, or mixture thereof, as described herein, or a composition as described herein or a formulation as described herein, for the preparation of adhesives, coatings, elastomers, or foams. The invention also encompasses said prepared adhesives, coatings, elastomers, foams (such as one component foam).

The invention also encompasses a product comprising the polyurethane, polyurea or mixture thereof, as described herein, or a composition as described herein, or obtained by curing a formulation as described herein. Non-limiting list of suitable products comprises adhesives, coatings, elastomers, foams and the like. In some embodiments, the product may be an adhesive. In some embodiments, the product may be an elastomer. In some other embodiments, the product may be a foam such as a one component foam. In yet other embodiments, the product may be a coating.

The present invention also encompasses material comprising at least one composition as described above or at least one compound as described above. Such a material may comprise, besides the composition according to the invention or the compound according to the invention: one or more polymers, pigments, dyes, fillers, plasticizers, fibers, flame retardants, antioxidants, lubricants, wood, glass, metals.

Among the polymers that may be used mixed with the composition of the invention or the compound according to the invention, mention may be made of: elastomers, thermoplastics, thermoplastic elastomers, impact additives.

The term "pigments" means colored particles that are dispersible in the composition. As pigments that may be used in the invention, mention may be made of titanium oxide, carbon black, carbon nanotubes, metal particles, silica, metal oxides, metal sulfides or any other mineral pigment; mention may also be made of phthalocyanins, anthraquinones, quinacridones, dioxazines, azo pigments or any other organic pigment, natural pigments (madder, indigo, crimson, cochineal, etc.) and mixtures of pigments. The pigments may represent from 0.05% to 15% by weight relative to the total weight of the material.

The term "dyes" means molecules that are soluble in the composition and that have the capacity of absorbing part of the visible radiation.

Among the fillers that may be used in the composition of the invention, mention may be made of: silica, clays, calcium carbonate, carbon black, kaolin, whiskers.

The presence in the compositions of the invention of fibers such as glass fibers, carbon fibers, polyester fibers, polyamide fibers, aramid fibers, cellulose and nanocellulose fibers or plant fibers (linseed, hemp, sisal, bamboo, etc.) may also be envisaged.

It may also be envisaged for the compositions of the invention or the compound according to the invention to be used for manufacturing sandwich materials by alternating superposition of layers of composition with layers of wood, metal or glass.

The presence in the composition of pigments, dyes or fibers capable of absorbing radiation may be used to ensure the heating of an article based on such a material by means of a radiation source such as a laser. The presence in the composition of pigments, fibers or electrically conductive fillers such as carbon black, carbon nanotubes, carbon fibers, metal powders or magnetic particles may be used to ensure the heating of an article based on such a material by the Joule effect, by induction or by microwaves. Such heating may allow the use of a process for manufacturing, transforming or recycling an article made of composition or material as described herein.

The present invention also encompasses a process for manufacturing an article comprising a composition as described above, this process comprising:

a) contacting at least one compound A comprising at least two functions selected from the group of function of formula —X—C(=O)—CHR$^1$—C(=O)—R$^2$, —C(=O)—C=C=R$^2$; or —C(=O)—CR$^1$=CR$^2$—NR$^4$R$^5$; wherein at least 25% by weight of compound A has a functionality ≤5, with % by weight being relative to the total weight of compounds A;

with at least one compound B comprising at least one —NH$_2$, or —NH$_3^+$ groups, or at least one functional group that generates —NH$_2$ or —NH$_3^+$ in situ, such as —N=C=O;

wherein $$\frac{\sum f_a N_a}{\sum f_b N_b} = R < 1;$$

or wherein $$\frac{\sum f_a N_a}{\sum f_a N_a + \sum f_b N_b} = R < 1,$$

when $R^1$ and $R^4$ together with the atom to which they are attached form a 5-, 6-, or 7-membered heterocyclyl or heteroaryl;

wherein $f_a N_a$ denotes the number of moles of —X—C(=O)—CHR$^1$—C(=O)—R$^2$, —C(=O)—C≡C—R$^2$; or —C(=O)—CR$^1$=CR$^2$—NR$^4$R$^5$ functions of the at least one compound A, and $f_b N_b$ denotes the number of moles of —NH$_2$, and/or —NH$_3^+$ groups or the number of moles of functional groups which could generate —NH$_2$ or NH$_3^+$ in situ, such as —N=C=O, of the at least one compound B;

b) the forming of the composition obtained from step a),
c) optionally the application of energy for hardening the article,
d) optionally cooling of the hardened article.

The polymerization can occur at room temperature. For example composition with a low glass-transition (below room temperature) will not require heating. In an embodiment, the application of energy for hardening the article in optional step c) of the process may consist, in a known manner, of heating at a temperature ranging from 30 to 250° C. The optional cooling of the hardened article is usually performed by leaving the article to return to room temperature, with or without use of a cooling means.

For the purposes of the present invention, the term "article" means a component based on a material comprising a composition or the compound according to the invention. It may also be an article made of composite material, may a coating, a terminal, a bead or a film of adhesive. It may especially be envisaged to introduce before, during or after step a) one or more additional components that may be chosen especially from polymers, pigments, dyes, fillers, plasticizers, fibers, flame retardants, antioxidants, lubricants, wood, glass and metals.

In some embodiments, in the article according to the invention, the composition has reached or exceeded the gel point.

The articles according to the invention may also be coatings that are deposited on a support, for instance a protective layer or a paint. They may also be an adhesive material.

An article resulting from the forming and hardening of the composition described above also forms part of the invention.

In an embodiment, an article based on the present composition can be manufactured by mixing the components of the composition, introduction in a mould and raising the temperature. The means for manufacturing such an article are well known to those skilled in the art.

Other methods for forming the article than moulding may be envisaged, such as filament winding, continuous moulding or film-insert moulding, infusion, pultrusion, RTM (resin transfer moulding), RIM (reaction-injection moulding), 3D printing, or any other method known to those skilled in the art.

The materials based on the composition of the invention, on account of their particular composition, can be transformed, repaired and recycled by raising the temperature of the article. Below the Tg temperature, the polymer is vitreous and has the behavior of a rigid solid body.

The materials resulting from the hardening of the composition of the invention described above constitute another object of the invention.

The present invention also encompasses a process for transforming at least one article made from a material as described above, this process comprising: the application to the article of a mechanical constraint at a temperature (T) above room temperature.

Preferably, in order to enable transformation within a time that is compatible with industrial application of the process, the process comprises the application to the article of a mechanical constraint at a temperature (T) above the glass transition temperature Tg of the material of which the article is composed.

Usually, such a process is followed by a step of cooling to room temperature, optionally with application of at least one mechanical constraint.

For the purposes of the present invention, the term "mechanical constraint" means the application of a mechanical force, locally or to all or part of the article, this mechanical force tending towards forming or deforming the article. Among the mechanical constraints that may be used, mention may be made of: pressure, moulding, blending, extrusion, blow-moulding, injection-moulding, stamping, twisting, flexing, pulling and shearing.

It may be, for example, twisting applied to a strip of material of the invention. It may be a pressure applied by means of a plate or a mould onto one or more faces of an article of the invention, stamping a pattern in a plate or sheet made of material of the invention. It may also be a pressure exerted in parallel onto two articles made of materials of the invention in contact with each other so as to bring about bonding of these articles. In the case where the article consists of granules of material of the invention, the mechanical constraint may consist of blending, for example in a blender or around an extruder screw. It may also consist of injection moulding or extrusion. The mechanical constraint may also comprise blow-moulding, which may be applied, for example, to a sheet of material of the invention. The mechanical constraint may also consist of a plurality of separate constraints, of identical or different nature, applied simultaneously or successively to all or part of the article or in a very localized manner.

This transformation may include mixing or agglomeration with one or more additional components chosen from: one or more polymers, pigments, dyes, fillers, plasticizers, fibers, flame retardants, antioxidants, lubricants.

In some embodiment, assembly, bonding and repair are particular cases of the transformation process described above.

This raising of the temperature of the article may be performed by any known means such as heating by conduction, convection, induction, spot heating, infrared, microwave or radiant heating. The means for bringing about an increase in temperature of the article in order to perform the processes of the invention comprise: an oven, a microwave oven, a heating resistance, a flame, an exothermic chemical reaction, a laser beam, a hot iron, a hot-air gun, an ultrasonication tank, a heating punch, etc.

An article made of material of the invention may also be recycled: either via direct treatment of the article: for example, the broken or damaged article is repaired by means of a transformation process as described above and may thus regain its prior working function or another function; or the article is reduced to particles by application of mechanical grinding, and the particles thus obtained may then be used in a process for manufacturing an article. In particular, according to this process, particles of material of the invention are simultaneously subjected to a raising of temperature and a mechanical constraint allowing them to be transformed into an article. The mechanical constraint that allows the transformation of particles into an article may, for example, comprise compression in a mould, blending or extrusion. This method thus makes it possible, by applying a sufficient temperature and an appropriate mechanical constraint, to mould articles from the material. In particular, it makes it possible to mold objects from the material based on composition which has reached or exceeded the gel point.

Another advantage of the invention is that it allows the manufacture of materials made of the present composition such as particles, granules, beads, rods, plates, sheets, films, strips, stems, tubes, etc. via any process known to those skilled in the art.

These elemental components may then be transformed under the combined action of heat and of a mechanical constraint into articles of the desired shape: for example, strips may, by stamping, be chopped into smaller pieces of chosen shape, sheets may be superposed and assembled by compression. These elemental components based on the present material, are easy to store, transport and handle. Specifically, the step for transforming the components according to the invention may be performed by the final user without chemical equipment (no toxicity or expiry date or VOC, and no weighing out of reagents).

The fields of application of these materials are all those of thermosetting resins: materials, high-end thermoplastic materials, and composites for motor vehicles, for aeronautical construction, electronics, sport, construction, furniture, foams, biomedical applications, printing and packaging.

The resins according to the invention can be worked without flowing under its own weight over a much broader range of temperatures, which makes it possible to apply varied transformation methods. These methods can be of the same nature as those used in the metal and glass fields.

The resins and the materials of the invention also make it possible, by applying a sufficient temperature and an appropriate mechanical constraint, to mould articles made of the composition. The resins and the materials of the invention also make it possible, by applying a sufficient temperature and using good contact of the components, to assemble components by welding so as to form a more complex article. The resins and the materials of the invention also make it possible, by applying a sufficient temperature and a mechanical constraint, to repair a crack or damage caused in a component formed from the material or in a coating based on the material.

The invention will now be illustrated by the following, non-limiting illustrations of particular embodiments of the invention.

EXAMPLES

Materials and Methods 1-propanol (>99.5%), butylamine (≥99%), benzylamine (≥99%), m-xylylene diamine (≥99%), tris(2-aminoethyl) amine (96%), cyclohexane dimethanol (mixture of cis and trans, 99%), 2,2,6-trimethyl-4H-1,3-dioxinon-4-one (≥93%) and tert-butyl acetoacetate (≥98%) were purchased from Sigma Aldrich. 2,2,6-trimethyl-4H-1,3-dioxinon-4-one was purified by distillation (0.2 torr, 65-67° C.). The temperature was kept below 90° C. to avoid decomposition.

2-ethyl hexylamine (98%), methyl acetoacetate (99%), octylamine (99%), triazabicyclodecene (98%), sulfuric acid (95-98%), p-toluene sulfonic acid (98%), N,N'-(ethane-1,2-diyl)bis(3-oxobutanamide) (synonym: ethylenediamine-N, N'-bis(acetoacetamide) (ethylene diamine AAm)), piperidine (99%), benzoyl acetone (99%), phenyl acetylene (98%), terephthalaldehyde (99%) were purchased from Sigma Aldrich. Piperazine (98%) was purchased from TCI chemicals. Pripol 2033 and priamine 1074are commercially available from Croda. 1,5-Diazabicyclononane (DBN) was purchased from Sigma Aldrich. Dibutyl tin dilaureate (DBTL) was purchased from TCI chemicals. Xylenes were purchased from Acros Organics. 1,4-phenylene diamine was purchased from TCI chemicals. Manganese(IV) oxide was purchased from Acros Organics. 1,6-Hexane diamine was purchased from Acros Organics.

Nuclear magnetic resonance spectra were recorded on a Bruker Avance 300 or a Bruker Avance II 700 spectrometer at room temperature, or others if specified.

ATR-FT IR spectra were collected using a Perkin-Elmer Spectrum1000 FTIR infrared spectrometer with a diamond ATR probe.

Thermogravimetric analyses were performed with a Mettler Toledo TGA/SDTA851e instrument under air or nitrogen atmosphere at a heating rate of 10° C. min-1 from 25° C. to 500° C.

Differential scanning calorimetry (DSC) analyses were performed with a Mettler Toledo instrument 1/700 system under nitrogen atmosphere at a heating rate of 10° C. min-1.

Dynamic mechanical analysis (DMA) was performed on a SDTA861e DMA from Mettler toledo. For the low $T_g$ samples, Stress-relaxation experiments were conducted on an Anton-Paar physica MRC 301 rheometer with a plate geometry of 25 mm and a strain of 5%.

Frequency sweep experiments were performed on an Anton-Paar physica MRC 301 rheometer with a plate geometry of 25 mm, an amplitude of 0.1%, which is within the linear viscoelastic region according to an amplitude sweep experiment, the frequency was changed from 100 rad s$^{-1}$ to $2*10^{-3}$ rad s$^{-1}$ and a normal force of 10N was used.

Stress-relaxation experiments were conducted on a Ares G2 rheometer from TA-instruments in torsion geometry with samples of (1.3×14.5×22) mm$^3$. An axial force of −0.01 N and a deformation of 1% were applied.

Rheology-experiments of the hard samples were performed on a Ares G2 rheometer from TA-instruments in torsion geometry with samples of dimension (1.3×14.5×22) mm$^3$ using an axial force of −0.01 N and a deformation of 1%.

Creep experiments were performed on a rectangular sample (5 mm×1.4 mm×10 mm) by using a TA-Q800 DMA, a constant stress of 0.1 MPa was applied.

Unless otherwise stated, tensile testing was performed on a Tinus-Olsen H10KT tensile tester equipped with a 100 N load cell for low Tg materials (<25° C.) or 5000 N Load cell for samples with a Tg>25° C. using flat dog bone type specimen with an effective gage length of 13 mm, a width of 2 mm, and a thickness of 1.3 mm. These dogbones were cut out using a Ray-Ran dog bone cutter.

Example 1 Low Molecular Weight Compounds

Propyl Acetoacetate:

2,2,6-Trimethyl-4H-1,3-dioxin-4-one (5.38 g, 34 mmol) and 1-propanol (10 mL) were mixed in a pressure tube and heated for 3 h at 135° C. After the reaction was finished according to thin layer chromatography (TLC), the excess of 1-propanol was removed in vacuo yielding pure propyl acetoacetate. Yield: 98%, 5.34 g. $^1$H NMR (300 MHz, CDCl$_3$, δ): 4.10 (t, J=6.5 Hz, 2H), 3.45 (s, 2H), 2.27 (s, 3H), 1.63 (m, 2H), 0.94 (t, J=6.5 Hz, 3H).

Propyl-3-(butylamino)but-2-enoate 1 and propyl-3-(benzylamino) but-2 enoate 3

Propyl acetoacetate (0.250 g, 1.73 mmol) and butyl- or benzylamine (2 eq, 3.47 mmol) were dissolved in 5 mL methanol and stirred overnight. When the enaminone formation was complete (TLC), the solvent was removed and the mixture was extracted twice with brine and CH$_2$Cl$_2$. The combined organic phases were dried with MgSO$_4$ and evaporated, yielding the desired product. The obtained product was purified by flash chromatography using EtOAc/hexane (25/75).

Yield propyl-3-(butylamino)but-2-enoate: 92%, 0.317 g. $^1$H NMR (300 MHz, CDCl$_3$, δ): 8.55 (s, 1H), 4.44 (s, 1H), 3.98 (t, J=6.77 Hz, 2H), 3.20 (q, J=6.52 Hz, 2H), 1.91 (s, 3H), 1.65-1.39 (m, 7H), 0.936 (t, J=7.37 Hz, 6H)

Yield benzyl-3-(butylamino)but-2-enoate: 94%, 0.379 g. $^1$H NMR (300 MHz, CDCl$_3$, δ)=8.96 (s, 1H), 7.39-7.27 (m, 5H), 4.56 (s, 1H), 4.45 (d, J=6.36, 2H), 4.02 (t, J=6.76, 2H), 1.93 (s, 3H), 1.65 (tt, 2H), 0.96 (t, 7.42)

N-benzyl-3-(benzylamino)but-2-enamide

A solution of 2,2,6-Trimethyl-4H-1,3-dioxin-4-one (0.5 g, 3.52 mmol) and benzylamine (1.13 g, 10.5 mmol) in 1.5 mL xylene was refluxed for 2 h. When the conversion of the starting product was complete (TLC), the solvent was removed. The obtained mixture consists of mainly N,N-benzylacetoacetamide and a small amount of N-benzyl-3-(benzylamine)but-2-enamide according to $^1$H NMR. This mixture was dissolved in 10 mL MeOH and benzylamine (0.75 g, 7.04 mmol) was added. The mixture was stirred at room temperature over 48 hours resulting in a white suspension. This suspension was poured in 25 mL of water and the white precipitate was filtered off, washed with water and dried to obtain N-benzyl-3-(benzylamino)but-2-enamide. Yield: 85%, 0.83 g. $^1$H NMR (300 MHz, CDCl$_3$, δ): 9.53 (s, 1H), 7.38-7.24 (m, 10H), 4.47-4.39 (m, 5H), 1.89 (s, 3H)

Benzylamine 2 (0.25 mmol, 57 mg) was added to a solution of propyl-3-(butylamino)but-2-enoate 1 (0.05 mmol, 20 mg) in benzene-d6 (1.5 mL) (Scheme 1).

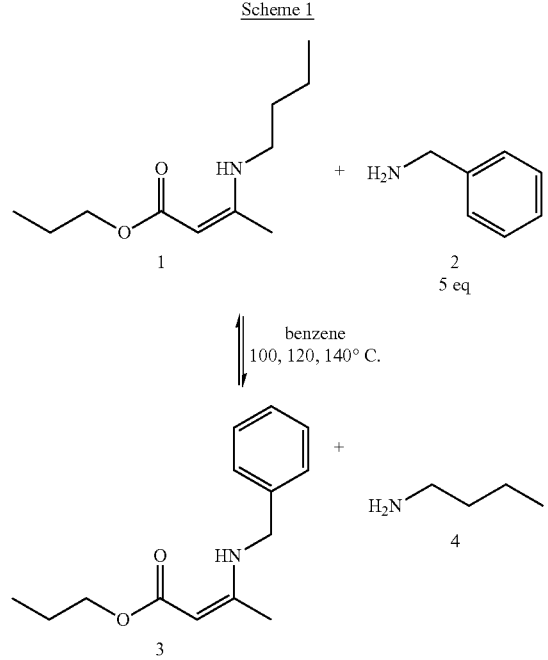

Scheme 1

Five equivalents of benzylamine were used to obtain a pseudo-first order reaction at low conversions. The mixture was heated (100, 120 and 140° C.) in a pressure tube and NMR spectra were taken at different time intervals (FIG. 1). The reaction was followed by integration of the two distinct sharp signals at 4.77 ppm and 4.80 pm for the N-butyl- and N-benzyl compound respectively. The rate of the reaction can be described using the following formula.

$$-\frac{d[\text{butyl vinyloog urethane}]}{dt} = v = k'[\text{butyl vinylogous urethane}]$$

Figure 2:
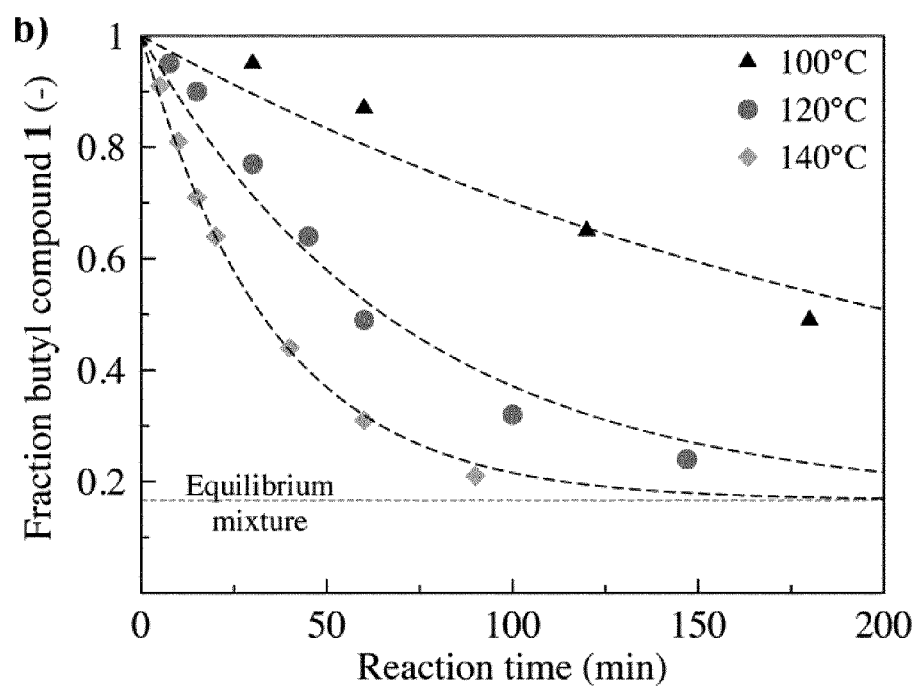
FIG. 2 represents a graph plotting the remaining fraction of propyl-3-(butylamino)but-2-enoate as a function of the reaction time, at different temperature.

The mole fraction of the propyl-3-(butylamino)but-2-enoate 1 was plotted versus the time (FIG. 2). The activation energy was calculated using the ratios of the initial slopes, which represents k'.

$$\frac{v_1}{v_2} = \frac{k'_1}{k'_2} \text{ and } E_a = -\ln\frac{v_1}{v_2}\frac{RT_1}{\left(1-\frac{T_1}{T_2}\right)} = (58 \pm 6)\text{kJ mol}^{-1}$$

At low conversions under these pseudo-first order conditions, a linear decay was observed. At higher conversions, the reaction evolved slowly to a chemical equilibrium, as the backward reaction becomes more important. An activation energy of (58±6) kJ mol−1 was calculated for the exchange reaction, using the initial slopes [S. K. Upadhyay, *Chemical kinetics and reaction dynamics*, Vol. 256, Springer, 2006].

These low MW compounds were also used to verify the thermal stability of these groups under conditions that would mimic thermal treatment of a bulk material. Vinylogous urethane 3 survived a treatment with an excess of benzylamine in bulk after heating overnight at 150° C.

Example 2 Polymer Network Composition Synthesis 1,4-Bis(hydroxymethyl)cyclohexane bisacetoacetate (CDM-AA)

1,4 Cyclohexane dimethanol (88.9 g, 0.61 mol) and tert-butyl acetoacetate (200 g, 1.26 mol) were dissolved in 120 mL of Xylene in a 1 L flask equipped with a still head and cooler. The mixture was heated for 90 minutes at 135° C. The tert-butanol product was removed by distillation during the reaction and the temperature in the still head was typically between 75 and 90° C. When the temperature dropped to 50° C., the mixture was cooled and the solvent was removed in vacuo. The resulting crude product crystallized upon cooling with ice and consisted of a 28:72 mixture of the cis- and trans isomer as indicated by the singlets at 4.08 ppm for the cis-isomer and 3.97 ppm for the trans-isomer. Recrystallization of the crude product in isopropanol yielded 72% of white crystals which consisted of 92% of the trans-acetoacetate. Yield: 72%, 96.5 g. $^1$H NMR (300 MHz, CDCl$_3$, δ)=4.09 (d, J=7.19 Hz, 2H cis), 3.97 (d, 6.48 Hz, 2H trans), 3.47 (s, 2H), 2.28 (s, 3H), 1.83-1.78 (m, 4H), 1.68-1.62 (m, 2H), 1.05-1.01 (m, 4H).

CDM-AA 5, m-xylene diamine 6 were used as monomers, with tris(2-aminoethyl)amine (TREN) 7 as a suitable trifunctional monomer to obtain networks.

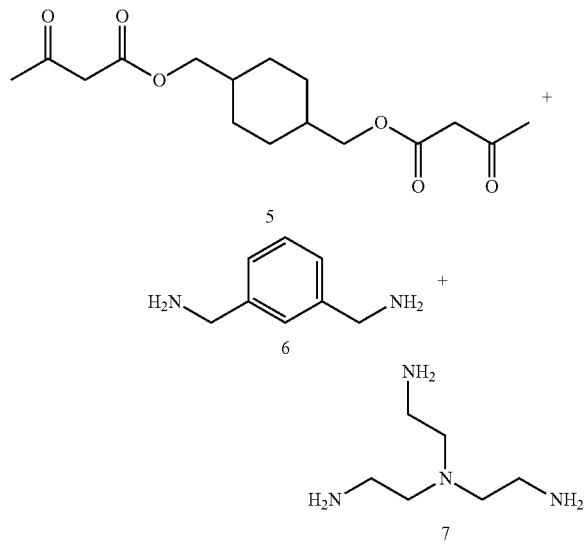

Polymer 2: Xylylene diamine (2.111 g, 15.5 mmol), tris(2-aminoethyl)amine (1.774 g, 12.1 mmol) and CDM-AA (10 g, 32.0 mmol) were mixed in a vial and heated in a heated oil bath at 80° C. When a homogeneous liquid mixture was obtained, the mixture was taken out of the oil-bath while keeping mixing manually. After 2 minutes, the mixture turned white due to phase separation (water release of the condensation reaction). The resulting white paste was taken out of the vial and pressed into a film of 1.3 mm between two Teflon sheets using a pre-heated press at 90° C. After 30 minutes, the film was transferred into a convection oven and dried during 24 h at 90° C. minutes followed by a short post-cure of 30 min at 150° C.

Figure 3:
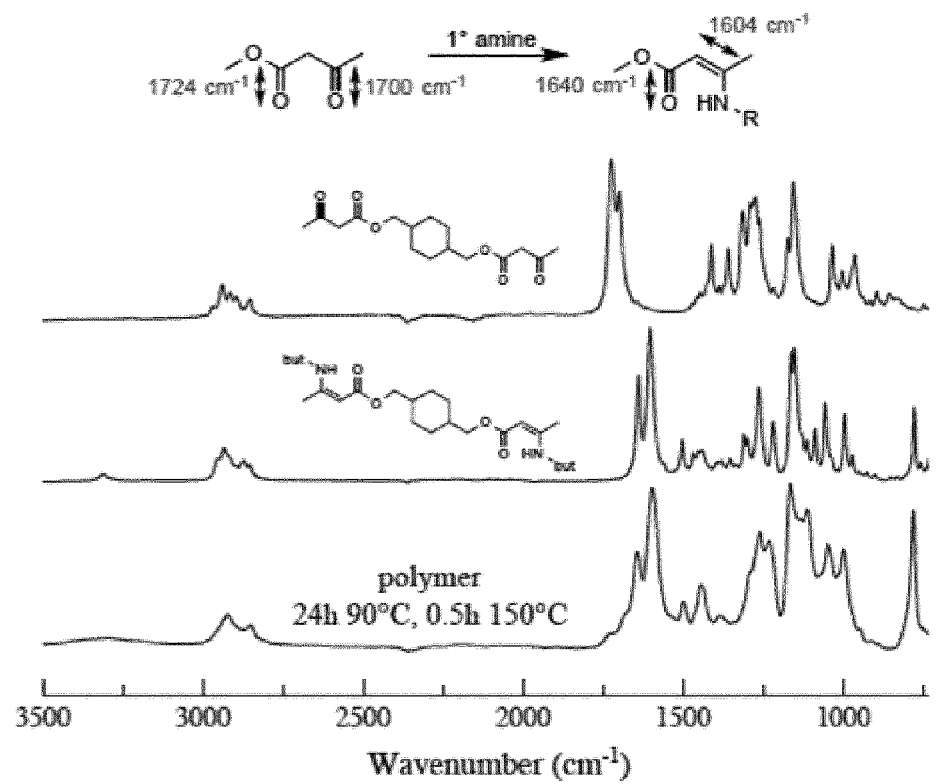
FIG. 3 represents the FTIR spectra of acetoacetate function, vinylogous urethane function and polymer 2 prepared in example 2.

ATR-FTIR confirmed the conversion of acetoacetates to polyvinylogous urethanes by the disappearance of the ester C=O and ketone C=O bands at 1724 and 1700 cm-1 and the appearance of the C=C and C=O bands of the polyvinylogous urethane at 1640 and 1604 cm-1 (FIG. 3).

Three polymers with a constant theoretical gel point of 0.83 (Flory formula) and a stoichiometric ratio [R=(equivalent acetoacetate)/(equivalent amine)] of 1, 0.95 and 0.90 were prepared. The synthesis of polymer 2 is given above. Polymer 2 and 3 could be pressed after grinding into a homogeneous plate (30 min 150° C.).

The swelling ratio and the soluble fraction were determined for all three resins (Table 1).

Solubility tests were carried out with samples of a size of (10×10×1.3) mm$^3$ with a weight of around 170 mg and 25 mL of NMP as solvent. The samples were heated for 24 h at 100° C. Then, the solvent was removed in vacuo and replaced twice by MeOH to remove the NMP as much as possible. Finally, the samples were dried under vacuum, first overnight at 40° C. and then at 120° C. for 2 h to ensure a complete removal of the solvent from the material.

For the determination of the swelling ratio, the samples were swollen for 24 h at 100° C. in NMP as solvent. The solvent was removed and the resulting polymer gels were weighed. The swelling ratio was determined using:

Swelling ratio=100%×$(m_{swollen}-m_{dry})/(m_{dry})$

Swelling ratio=$m$swollen–$m$dry$m$

TABLE 1

Swelling ratio and soluble fraction for different stoichiometric ratios of amine and acetoacetate.

| Polymer | Functionality | 1 Eq | 2 Eq | 3 Eq |
|---|---|---|---|---|
| CDM-AA 5 | 2 | 1.00 | 0.95 | 0.90 |
| TREN 7 | 3 | 0.32 | 0.36 | 0.40 |
| Xylylene diamine 6 | 2 | 0.52 | 0.46 | 0.40 |
| Ratio | | 1 | 0.95 | 0.90 |
| Soluble fraction (%) | | 4 | 11 | 25 |
| Swelling ratio (%) | | 390 | 590 | 750 |

As can be observed in Table 1, material with more free amines showed a higher swelling ratio, which can be attributed to the reorganization of the network. Without an excess of amines, very little amines were available for network reorganization.

The obtained networks showed significant swelling but did not dissolve in N-methylpyrrolidone (NMP), even when heated for 24 h at 100° C., well above the glass transition temperature of these materials (vide infra). Similar treatment, but with additional benzyl amine (equal mass as the polymer sample) in the solvent, resulted in complete dissolution due to the amine exchange reactions giving depolymerization.

The polymer 2 obtained with a stoichiometric ratio of 0.95 was chosen for characterization study (Example 3).

Example 3 Polymer Composition Characterization

Figure 4:
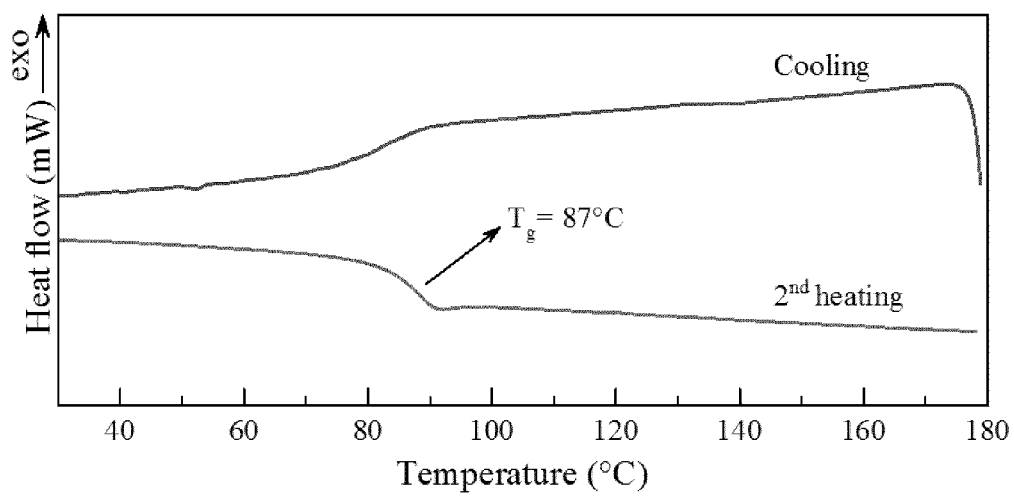
FIG. 4 represents the DSC thermogram of the vinylogous urethane polymer 2 prepared in example 2. A glass transition is observed at 87° C.
Figure 5:
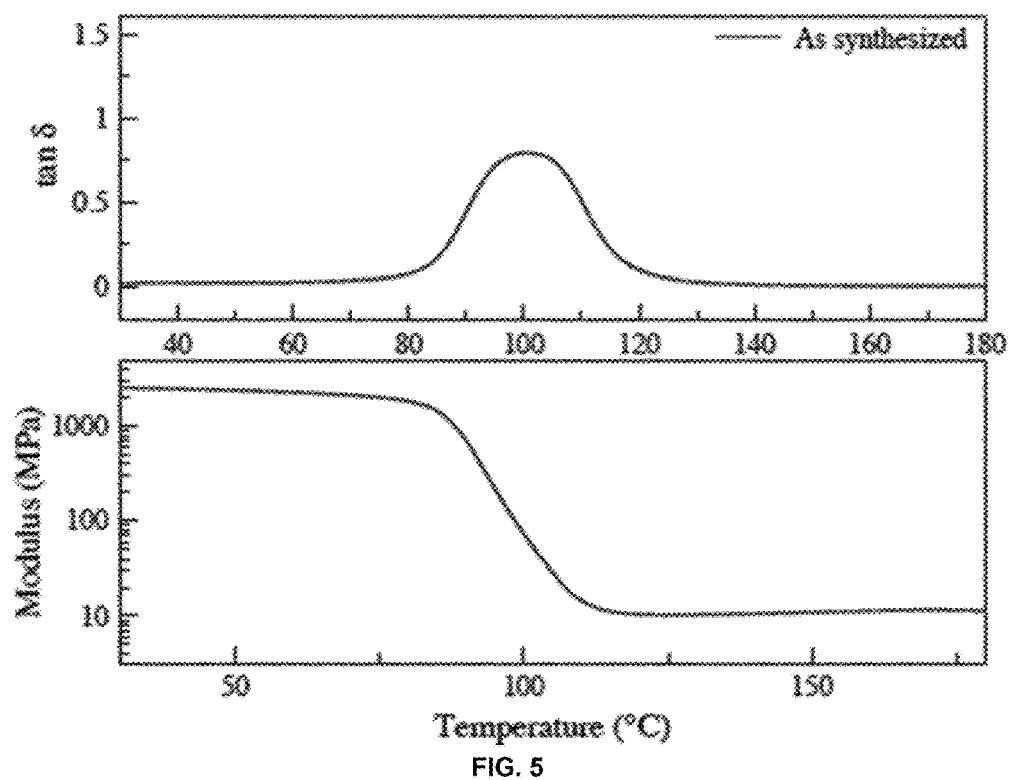
FIG. 5 represents DMA Plots for Storage Modulus, and Tan Delta.
Figure 6:
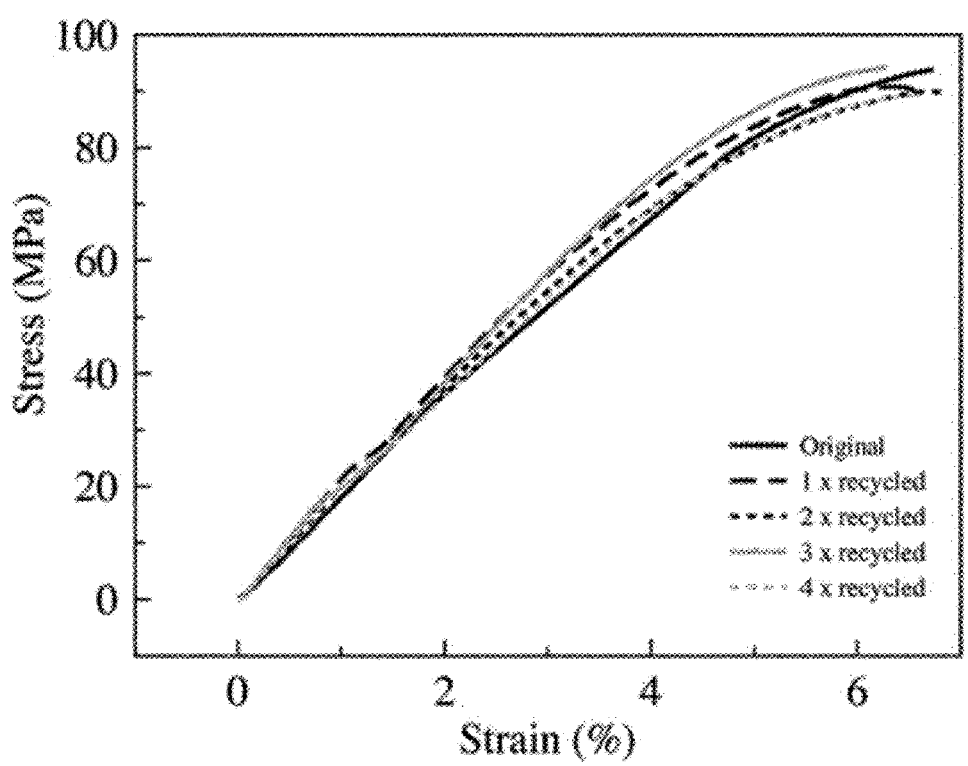
FIG. 6 represents stress-strain curves for the polymer 2 as prepared in example 2 and for recycled samples thereof.

Polymer 2 as prepared in Example 2 was further characterized: The bulk polymerization of CDM-AA, m-xylylene diamine and TREN yielded a glassy network at room temperature with excellent mechanical properties, evidenced by a glass transition temperature of about 87° C. (FIG. 4), a storage modulus of ~2.4 GPa (FIG. 5) and stress at break of ~90 MPa (FIG. 6). Dynamic mechanical analysis (DMA) confirmed the presence of a network with a rubbery plateau of 10 MPa (FIG. 5).

Figure 7:
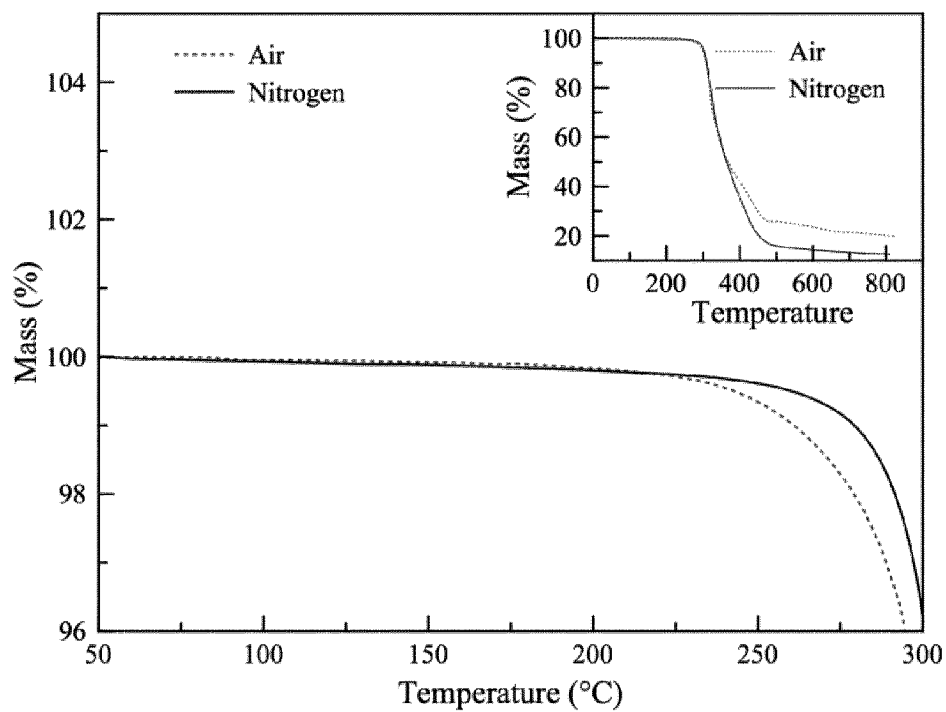
FIG. 7 represents a graph plotting the TGA of the polymer 2 as prepared in example 2 under air and nitrogen atmosphere.
Figure 8:
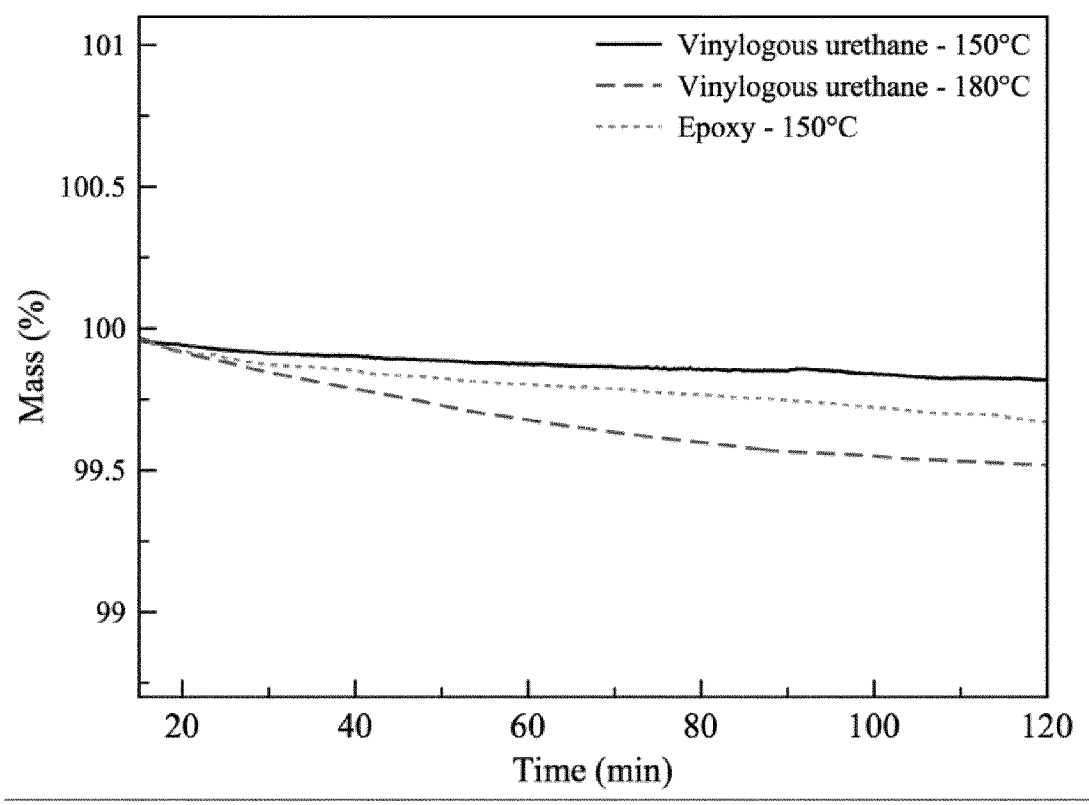
FIG. 8 represents a graph plotting the TGA of the polymer 2 as prepared in example 2 at 150° C. and 180° C. The TGA of a commercial epoxy (EPON 828 cured with diethylenetriamine (DETA)) is shown as a reference.

By thermogravimetic analysis (TGA), the vinylogous urethane networks proved to have good thermal stability with a mass loss of 2.5% at 287° C. (295° C. under nitrogen atmosphere) (FIG. 7). Since the materials are expected to withstand elevated temperatures for longer periods when being processed, isothermal TGA was also conducted (FIG. 8). The weight loss after 2 h at 150° C. and 180° C. was negligible (<0.5%) and comparable to that of a commercial epoxy (EPON 828 cured with DETA), indicating that the vinylogous urethane networks are stable when heated during a reasonable timeframe.

Figure 9:
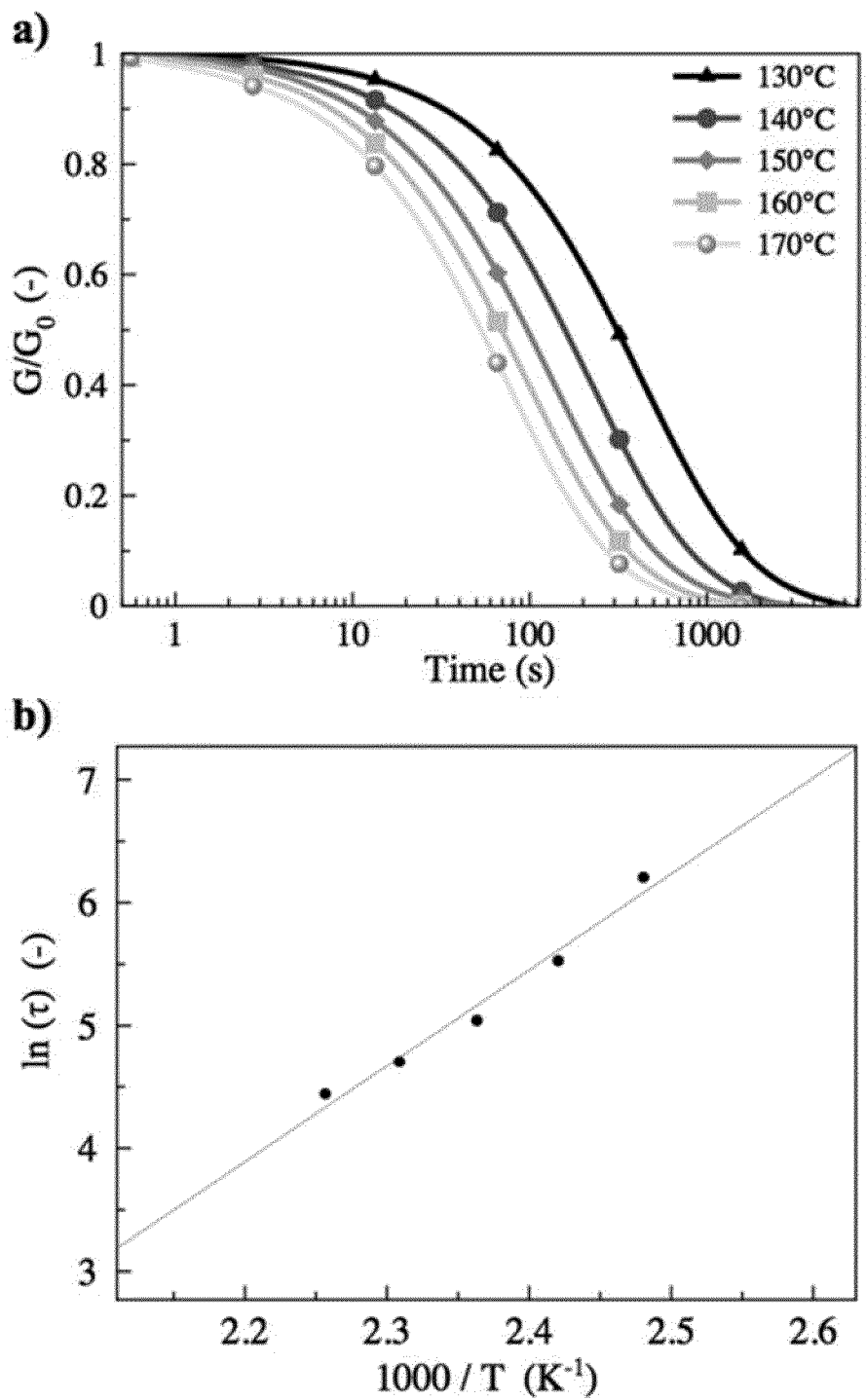
FIG. 9 represents in a) a graph plotting the normalized stress-relaxation curves at different temperatures and in b) a graph plotting the fitting of the relaxation times to the Arrhenius equation.

The flow properties of the vinylogous urethane polymer 2 prepared in Example 2 were studied by stress-relaxation and creep experiments. For the stress-relaxation, a torsional strain of 1% was applied and the relaxation modulus was monitored as a function of time. As shown in FIG. 9a, full stress-relaxation was observed at all temperatures. This behavior is in accordance with a viscoelastic fluid, further indicating that no non-exchangeable cross-links were introduced during the curing step or stress-relaxation experiment.

Based on the Maxwell model for viscoelastic fluids, relaxation times were determined at 37% (1/e) of the normalized relaxation modulus. These relaxation times range from 550 s at 130° C. to 85 s at 170° C. Taking into account the absence of catalyst and the rather rigid polymer structure, no other permanently cross-linked systems or vitrimers exhibit such a fast relaxation. This characteristic likely reflects the very high density of vinylogous urethanes in the network and the low activation energy for exchange (vide supra). Since the relaxation times are controlled by the associative exchange reactions, the temperature dependence of the relaxation time can be described by the Arrhenius equation [L. H. Sperling, *Introduction to Physical Polymer Science*, Wiley-Interscience, 2005.]

$$\tau(T) = \tau_0 \exp\left(\frac{E_a}{RT}\right) \quad \text{(Eq. 1)}$$

As shown in FIG. 9b, the relaxation times indeed followed the Arrhenius law, and an activation energy of (60±5) kJ mol-1 was calculated from the slope. This result is in very good agreement with the activation energy obtained for the compounds prepared in example 1.

Figure 10:
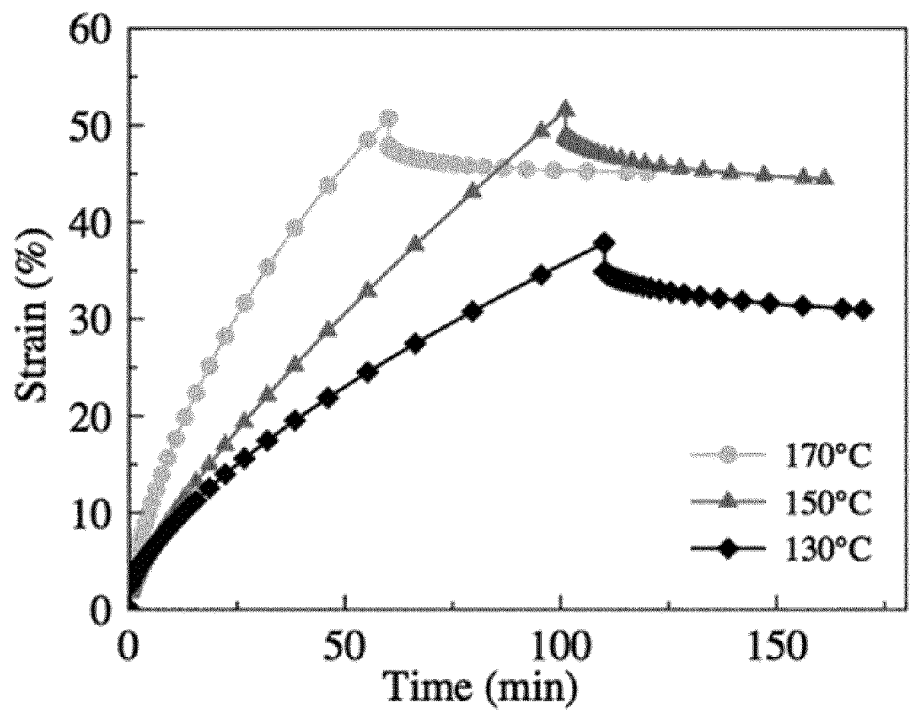
FIG. 10 represents a graph plotting curves of elongational creep of the polymer 2 of example 2 at various temperatures (circles: 170° C.; triangles: 150° C.; diamonds: 130° C.).

In accordance with stress-relaxation experiments, creep experiments also confirmed that the vinylogous urethane polymer according to the invention behaves like a viscoelastic liquid at elevated temperatures. FIG. 10 depicts the results of elongational creep experiments at different temperatures. Following the initial elastic response, primary creep with a rapid rate decrease was observed. Then, a steady state was reached, characterized by a constant creep rate. When the stress was released, the material recovered only its initial elastic response and a permanent deformation remained. The networks were easily deformed up to 45% without rupture over a broad temperature range. These results clearly show that the vinylogous urethane polymers according to the invention can be processed without a precise control of the temperature, in strong contrast to the strict conditions required for processing of thermoplastics.

Figure 11:
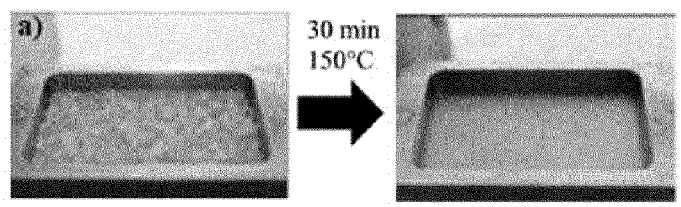
FIG. 11 represents photographs showing the recycling of grinded polymer 2 made in example 2 by compression molding a sample 30 min at 150° C.
Figure 12:
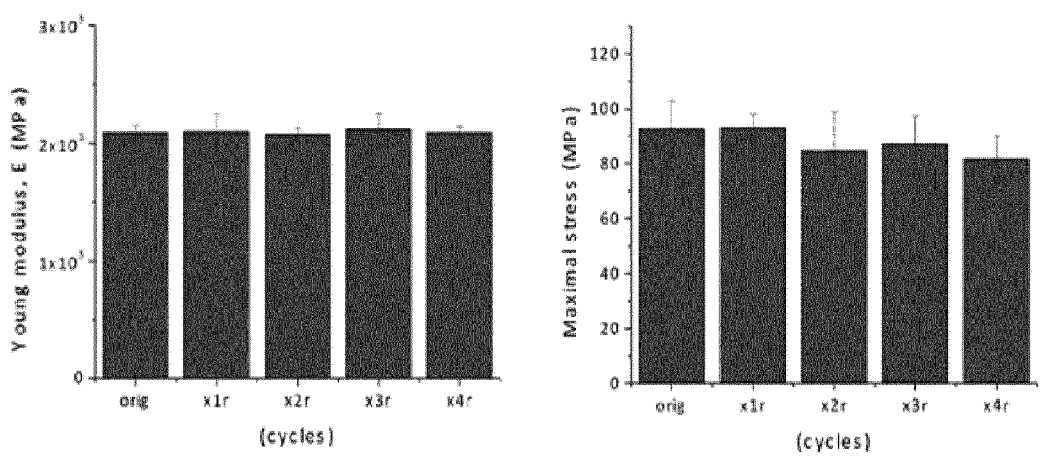
FIG. 12 represent graphs plotting the Young modulus and the Maximal stress for the polymer 2 as prepared in example 2 and for recycled samples thereof.
Figure 13:
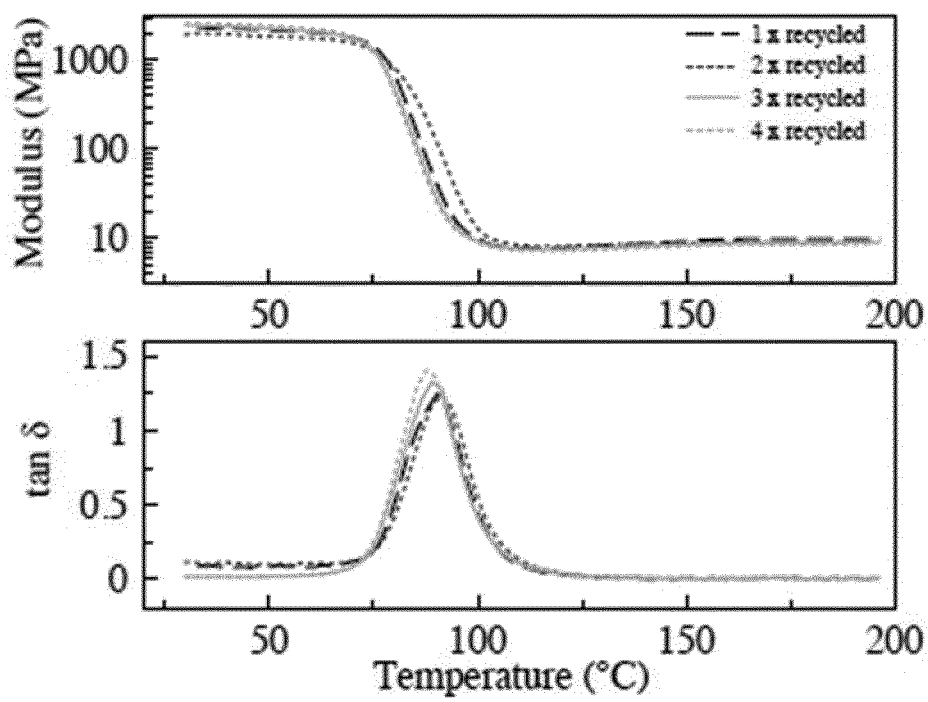
FIG. 13 represents DMA Plots for Storage Modulus, and Tan Delta of the polymer 2 as prepared in example 2 and of recycled samples thereof.
Figure 14:
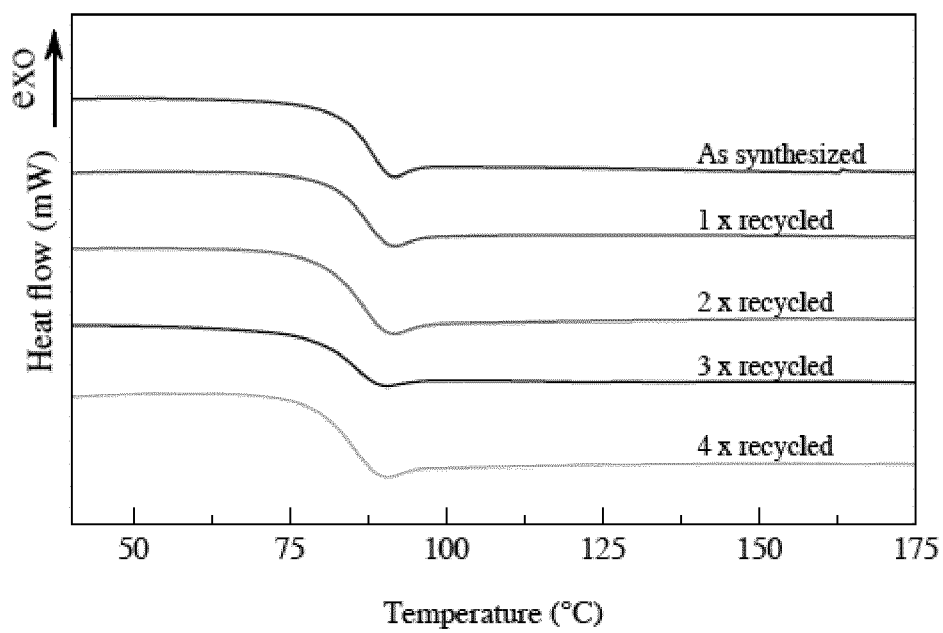
FIG. 14 represents the DSC thermogram of the vinylogous urethane polymer 2 prepared in example 2 and of recycled samples thereof.

Recycling:

The recyclable nature of the networks was examined by first grinding the samples into fine particles which were used as raw substance for compression molding (FIG. 11). To ensure the reversibility, the procedure was repeated four times and the recycled samples were subjected to tensile tests, DMA, DSC, solubility experiments, and ATR-FTIR for characterization. Tensile testing was performed on a Tinus-Olsen H10KT tensile tester equipped with a 100 N load cell, using flat dog bone type specimen with an effective gage length of 13 mm, a width of 2 mm, and a thickness of 1.3 mm. The samples were cut out using a Ray-Ran dog bone cutter. The tensile tests were run at a speed of 10 mm/min. Tensile tests revealed that the mechanical properties of the sample were fully recovered after being remoulded for 30 minutes at 150° C. (FIG. 6). No change was observed in the Young's modulus and stress at break (FIG. 12) while the strain at break ranged between 5.5 and 7.5% independently of the recycling cycle. In addition, DMA confirmed the recovery of the mechanical properties, as the observed rubbery plateau was constant within the experimental error (±5%), which indicates that no cross-links were formed nor broken (FIG. 13). Since a slight shift in the maximum value of tan δ was observed, DSC was performed, and showed that the glass transition (Tg) at the second heating changed by less than 1° C. (FIG. 14). In further agreement with DMA, solubility experiments showed that the soluble fraction varied from 7 to 14% without following a clear trend (Table 2), with the soluble fraction of the polymer as originally prepared being almost identical to that of the material recycled four times.

TABLE 2

| soluble fraction of polymer 2 as originally made and of recycled samples thereof. | |
|---|---|
| Sample | Soluble fraction (%) |
| Polymer 2 as originally prepared | 9-13 |
| 1× recycled | 6-8 |
| 2× recycled | 9-11 |
| 3× recycled | 12-15 |
| 4× recycled | 8-12 |

The lowest and highest values of three measurements are given.

Figure 15:
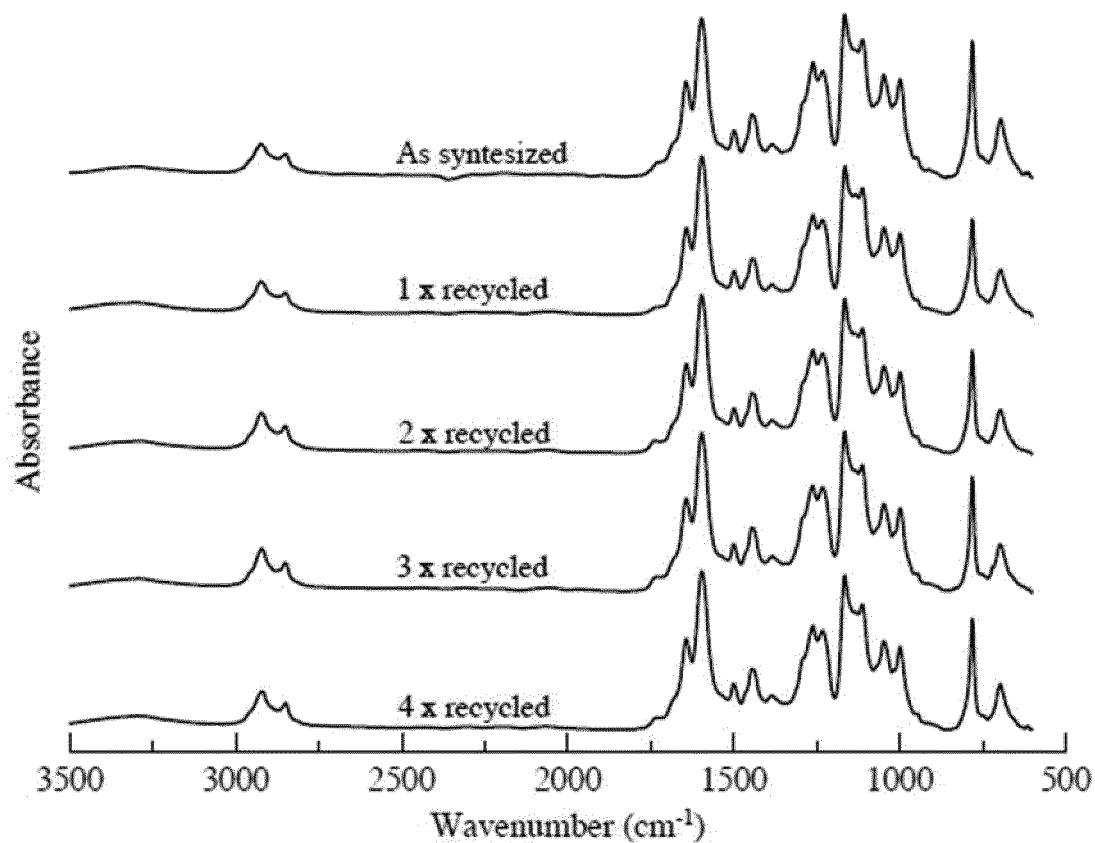
FIG. 15 represents the FTIR spectra of polymer 2 prepared in example 2 and of recycled samples thereof.

Furthermore, no chemical degradation was visible on ATR-FTIR. The IR-spectra after subsequent cycles were almost identical (FIG. 15). In general, the vinylogous urethane polymers exhibited excellent recycling properties over four recycling cycles without loss of mechanical properties or chemical changes.

The present inventors have developed new catalyst-free polymeric network having vitrimer like properties. The polymer of the invention possessed great mechanical properties and a Tg of 87° C. They behaved like classical networks evidenced by DMA and their insolubility. The vinylogous urethane networks were able to flow as shown by stress-relaxation and creep experiments. Moreover, they could be recycled without loss of mechanical properties.

The present inventors have therefore developed new compositions based on the transamination reactions of vinylogous urethanes. These compositions exhibited a Tg of 87° C., and displayed excellent mechanical properties such as a storage modulus of about 2.4 GPa. These compositions were insoluble even at elevated temperatures. Stress-relaxation and creep experiments showed a viscoelastic liquid behavior. Due to the fast exchange reactions and high density of exchangeable bonds throughout the network, relaxation times as short as 85 s at 170° C. were achieved without the use of any catalyst. These compositions could be recycled by grinding and remoulding the material several times without loss of mechanical properties. The compositions and material and articles made therefrom can be reworked to any shape while being at the same time permanently cross-linked.

Example 4

Low molecular weights compounds were prepared as shown in scheme 2.

Scheme 2

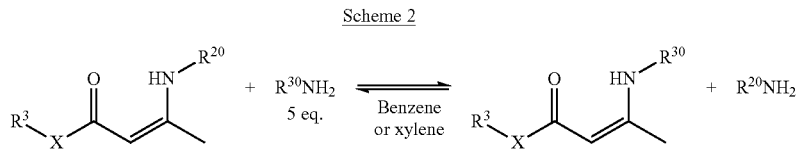

Vinylogous urea (X is $NR^{13}$)
Vinylogous amide (X=$CR^{14}R^{15}$)
All exchange reactions were performed in benzene or xylene at a concentration of 6.11 $10^{-2}$ M of the starting vinylogous compound.

Example 4.1

Synthesis of N,N'-(ethane-1,2-diyl)bis(3-(butylamino)but-2-enamide and N,N'-(ethane-1,2-diyl)bis(3-(benzylamino)but-2-enamide)

N,N'-(ethane-1,2-diyl)bis(3-oxobutanamide) (1 eq., 1 g) and butylamine (2 eq.) or benzylamine (2 eq.) were mixed in 20 mL water and stirred for 6 h at room temperature. The white precipitate was filtered, washed with water (3×10 mL) and dried in vacuo yielding N,N'-(ethane-1,2-diyl)bis(3-(butylamino)but-2-enamide and N,N'-(ethane-1,2-diyl)bis(3-(benzylamino)but-2-enamide) as a white powder.

Yield N,N'-(ethane-1,2-diyl)bis(3-(butylamino)but-2-enamide: 95%, $^1$H NMR (300 MHz, benzene-d6) δ=9.55 (br s, 2H), 5.47 (br s, 2H), 4.28 (s, 2H), 3.32 (2H, s), 2.72 (4H, m), 1.52 (6H, s), 1.19 (m, 8H), 0.73 (t, J=7.15, 6H).

Yield N,N'-(ethane-1,2-diyl)bis(3-(benzylamino)but-2-enamide): 93% $^1$H NMR (300 MHz, benzene-d6) δ=10.00 (br s, 2H), 7.08-5.98 (m, 8H), 5.23 (br s, 2H), 4.24 (s, 2H), 3.86 (d, J=6.68, 4H), 3.27 (brs, 4H)

Kinetics Exchange Reaction N,N'-(ethane-1,2-diyl)bis(3-(butylamino)but-2-enamide and benzylamine (Scheme 3)

Figure 16:
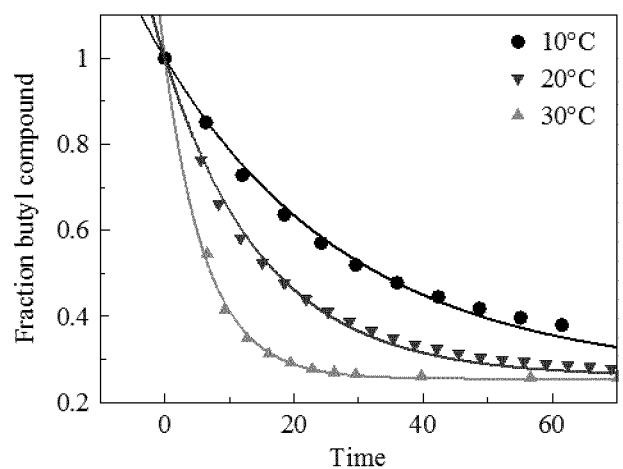
FIG. 16 represents a graph plotting the remaining fraction of N,N'-(ethane-1,2-diyl)bis(3-(butylamino)but-2-enamide as a function of the reaction time, at different temperature.

Benzylamine (0.25 mmol, 26 mg) was added to a solution of N,N'-(ethane-1,2-diyl)bis(3-(butylamino)but-2-enamide (0.05 mmol, 8.15 mg) in benzene-d6 (0.79 mL). Five equivalents of benzylamine versus the vinylogous urea groups were used to obtain a pseudo-first order reaction at low conversions. The mixture was kept at 10° C., 20° C. and 30° C. in a NMR-tube and spectra were recorded on-line at different time intervals. The reaction was followed by integration of t×d signal at 2.72 ppm of the butyl compound and the t signal at 3.86 ppm of the benzyl compound. The mole fraction of the N,N'-(ethane-1,2-diyl)bis(3-(butylamino)but-2-enamide was plotted versus the time. The results are shown in FIG. 16.

Example 4.2

Synthesis of 1-(piperidin-1-yl)butane-1,3-dione (Scheme 4)

Scheme 4

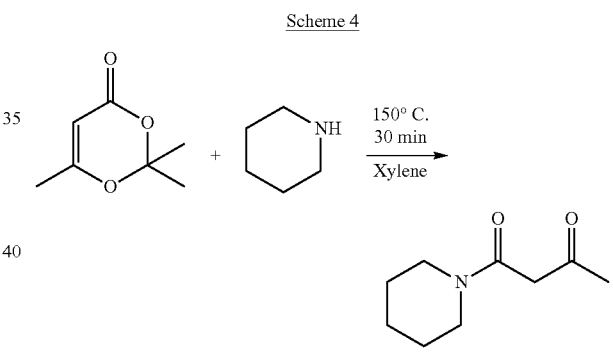

Piperidine (3.29 g, 38.68 mmol) and 2,2,6-trimethyl-4H-1,3-dioxin-4-one (5 g, 35.15 mmol) were dissolved in 7 mL xylenes and heated for 30 min at 150° C. after which full Scheme 3

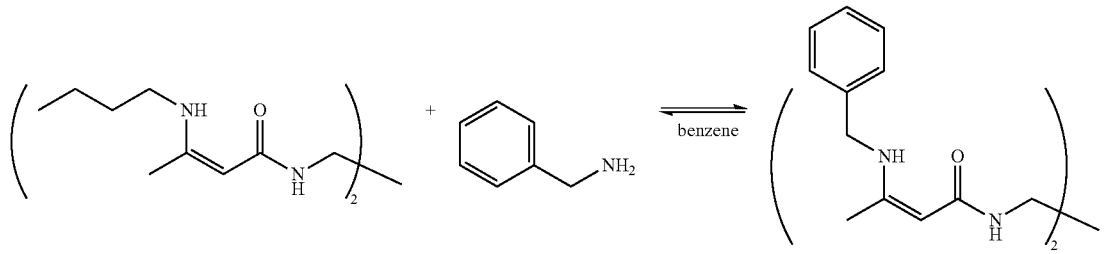

conversion was obtained according to TLC. The solvent and excess of piperidine was removed in vacuo and used without additional purification. Yield: 95%. ¹H NMR (300 MHz, CDCl₃): d=2.75-2.4 (m, 6H), 2.19 (s, 3H), 3.48-3.26 (m, 6H).

Synthesis of 3-(butylamino)-1-(piperidin-1-yl)but-2-en-1-one and 3-(benzylamino)-1-(piperidin-1-yl)but-2-en-1-one (Scheme 5)

Scheme 5

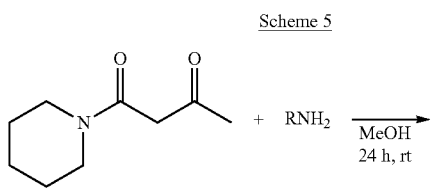

R = n-but or benzyl 1-(piperidin-1-yl)butane-1,3-dione (1 g, 5.91 mmol) and butylamine (0.64 g, 8.86 mmol) or benzyl amine (0.646 g, 6.03 mmol) were mixed in 5 mL MeOH and stirred overnight at room temperature after which the solvent was removed in vacuo. The mixture was extracted using 10 mL water and dichloromethane (3×10 mL). The combined organic fractions were dried with MgSO₄ filtered and dried in vacuo yielding the desired product.

Yield 3-(butylamino)-1-(piperidin-1-yl)but-2-en-1-one: 85% ¹H NMR (300 MHz, CDCl₃): 9.51 (br s, 1H), 4.60 (s, 1H), 3.44 (t, J=5.34, 4H), 3.17 (m, 2H), 1.92 (s, 3H), 1.63-1.36 (m, 10H), 0.92 (t, J=7.23, 3H)

Yield 3-(benzylamino)-1-(piperidin-1-yl)but-2-en-1-one: 92% ¹H NMR (300 MHz, CDCl₃): 9.95 (br s, 1H), 7.34-7.25 (m, 5H), 4.72 (s, 1H), 4.42 (d, J=6.45, 2H), 3.48 (t, J=5.23, 4H), 1.91 (s, 3H), 1.56 (m, 6H)

Kinetics Exchange Reaction 3-(butylamino)-1-(piperidin-1-yl)but-2-en-1-one and benzylamine (Scheme 6)

Figure 17:
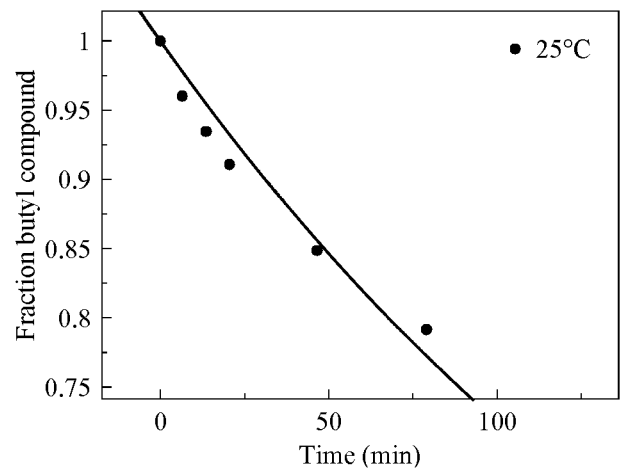
FIG. 17 represents a graph plotting the remaining fraction of 3-(butylamino)-1-(piperidin-1-yl)but-2-en-1-one as a function of the reaction time.

Benzylamine (0.25 mmol, 26 mg) was added to a solution of 3-(butylamino)-1-(piperidin-1-yl)but-2-en-1-one i.e. the N-butyl vinylogous urea compound (0.05 mmol, 11.3 mg) in benzene-d6 (0.79 mL). Five equivalents of benzylamine versus the vinylogous urea groups were used to obtain a pseudo-first order reaction at low conversions. The mixture was kept at 25° C. in a NMR-tube and spectra were recorded on-line at different time intervals. The reaction was followed by integration of t×d signal at 2.89 ppm of the butyl compound and the t signal at 4.00 ppm of the benzyl compound. The mole fraction of the 3-(butylamino)-1-(piperidin-1-yl)but-2-en-1-one was plotted versus the time. The results are shown in FIG. 17.

Example 4.3

Synthesis of 3-(benzylamino)-1-phenylbut-2-en-1-one and 3-(butylamino)-1-phenylbut-2-en-1-one (Scheme 7)

Scheme 7

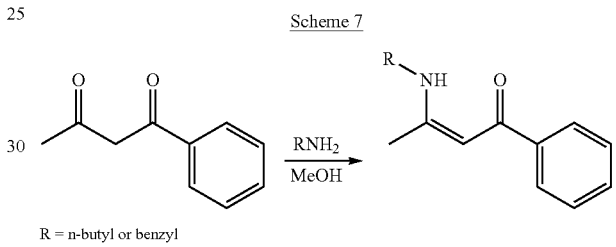

R = n-butyl or benzyl

Benzoyl acetone (1.5 g, 9.25 mmol) and butylamine (1.83 mL, 18.5 mmol) or benzyl amine (2 mL, 18.5 mmol) were mixed in 10 mL MeOH and stirred overnight at room temperature, after which full conversion was observed with TLC (rf=0.36 EtOAc/hept 20/80). The solvent was removed in vacuo and filtered over a short column of silica to remove the excess of amine.

Yield 3-(benzylamino)-1-phenylbut-2-en-1-one: 81%, ¹H NMR (300 MHz, CDCl₃): δ 11.75 (s, 1H), 7.98-7.75 (m, 2H), 7.51-7.16 (m, 8H), 5.75 (s, 1H), 4.54 (d, J=6.3 Hz, 2H), 2.07 (s, 3H)

Yield 3-(butylamino)-1-phenylbut-2-en-1-one: 83%, 1H NMR (300 MHz, CDCl₃): 11.5 (brs, 1H), 7.90-7.86 (m, 2H), 7.43-7.40 (m, 3H), 5.58 (s, 1H), 3.34 (td, J=6.89; 5.92), 2.09 (s, 3H), 1.71-1.62 (m, 3H), 1.52-1.44 (m, 2H), 0.98 (t, J=7.27, 3H)

Scheme 6

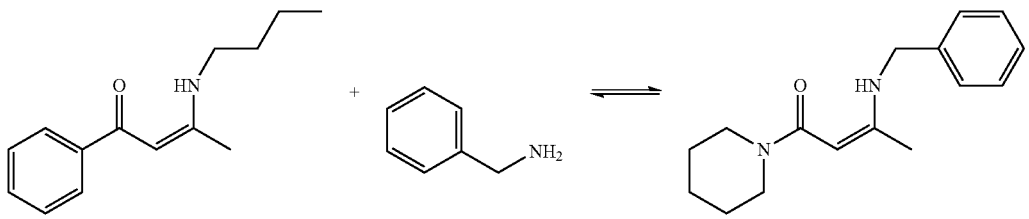

Kinetics Exchange Reaction 3-(butylamino)-1-phenylbut-2-en-1-one and benzylamine (Scheme 8)

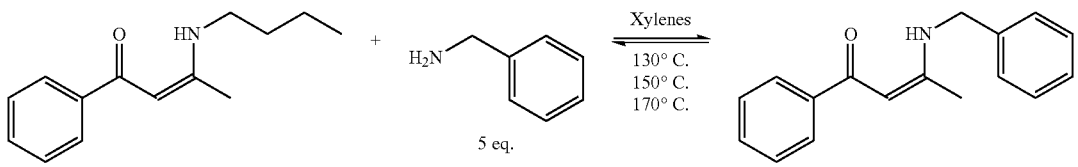

Scheme 8

Figure 18:
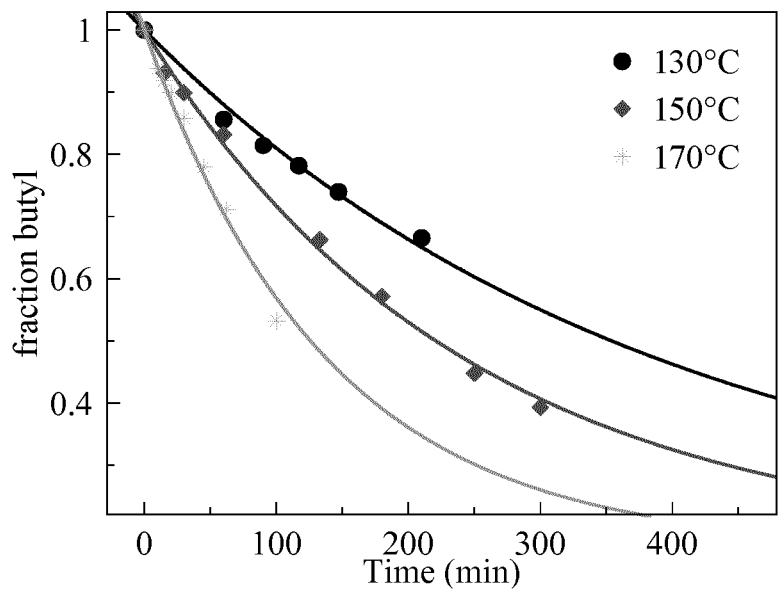
FIG. 18 represents a graph plotting the remaining fraction of 3-(butylamino)-1-phenylbut-2-en-1-one as a function of the reaction time, at different temperature.

Benzylamine (2.3 mmol, 246 mg) was added to a solution of 3-(butylamino)-1-phenylbut-2-en-1-one i.e. the N-butyl vinylogous amide compound (0.46 mmol, 100 mg) in xylenes (7.54 mL). Five equivalents of benzylamine versus the vinylogous amide groups were used to obtain a pseudo-first order reaction at low conversions. The mixture was kept at 130° C., 150° C. and 170° C. in a pressure-tube and GC analysis was performed at different time intervals. The reaction was followed by integration of the free induction decay (FID) signals at 6.7 min and at 7.45 min for the butyl- and benzyl model compound respectively. The integrated signals were corrected using a calibration curve for both compounds to take a different molar response factor in account. Gas chromatography (GC) was performed on an Agilent 7890A system equipped with a VWR Carrier-160 hydrogen generator and an Agilent HP-5 column of 30 m length and 0.320 mm diameter. A FID detector was used and the inlet was set to 250° C. with a split injection of ratio 25:1. Hydrogen was used as carrier gas at a flow rate of 2 mL/min. The oven temperature was increased with 20° C./min from 50° C. to 120° C., followed by a ramp of 50° C./min. to 300° C. and 5 min isothermal at 300° C. The mole fraction of the 3-(butylamino)-1-phenylbut-2-en-1-one was plotted versus time. The results are shown in FIG. 18.

Example 5

Methyl-3-(octylamino)but-2-enoate and methyl-3-((2-ethylhexyl)amino)but-2-enoate (Scheme 9)

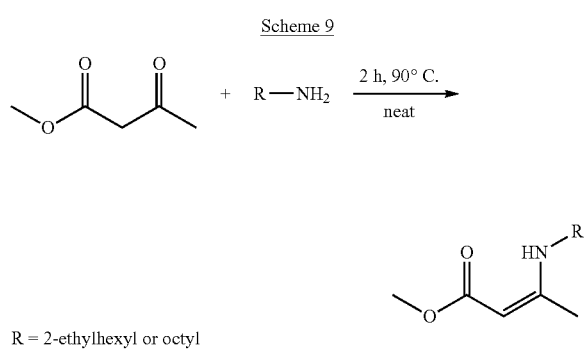

R = 2-ethylhexyl or octyl

Methyl acetoacetate (1.0 eq) and 2-ethyl hexylamine or octylamine (1.1 eq) were mixed in bulk and heated for 2 h at 90° C. while purging $N_2$ to remove $H_2O$. The excess of amine was removed by passing the mixture over a short silica column using ethyl acetate as eluents.

Yield methyl-3-(octylamino)but-2-enoate: 99%, $^1$H NMR (300 MHz, CDCl$_3$): δ (ppm)=0.88 (t, 3H, J=7), 1.26-1.38 (m, 10H), 1.51-1.59 (m, 2H), 1.91 (s, 3H), 3.16-3.22 (m, 2H), 3.55 (s, 3H), 4.36 (s, 1H), 8.47 (brs, 1H)

Yield methyl-3-((2-ethylhexyl)amino)but-2-enoate: 99%, $^1$H NMR (300 MHz, CDCl$_3$): δ (ppm)=0.88 (t, 6H, J=7.3), 1.27-1.30 (m, 9H), 1.90 (s, 3H), 3.04-3.16 (m, 2H), 3.61 (s, 3H), 4.41 (s, 1H), 8.61 (brs, 1H)

Effect of the Presence or Absence of a Catalyst on the Exchange Reaction

Methyl-3-(octylamino)but-2-enoate (5 eq.) was mixed together with 2-ethyl hexylamine (1 eq.), dodecane (Internal standard, 0.5 eq) and a catalyst as listed in table 3 in a test tube.

TABLE 3

| Catalyst | Equivalents |
| --- | --- |
| Blanco | / |
| p-toluene sulfonic acid (pTsOH) | 0.01 |
| Triazabicyclodecene (TBD) | 0.05 |
| Dibutyl tin dilaureate (DBTL) | 0.05 |
| Sulfuric acid | 0.005 |
| 1,5-Diazabicyclononane (DBN) | 0.05 |

Figure 19:
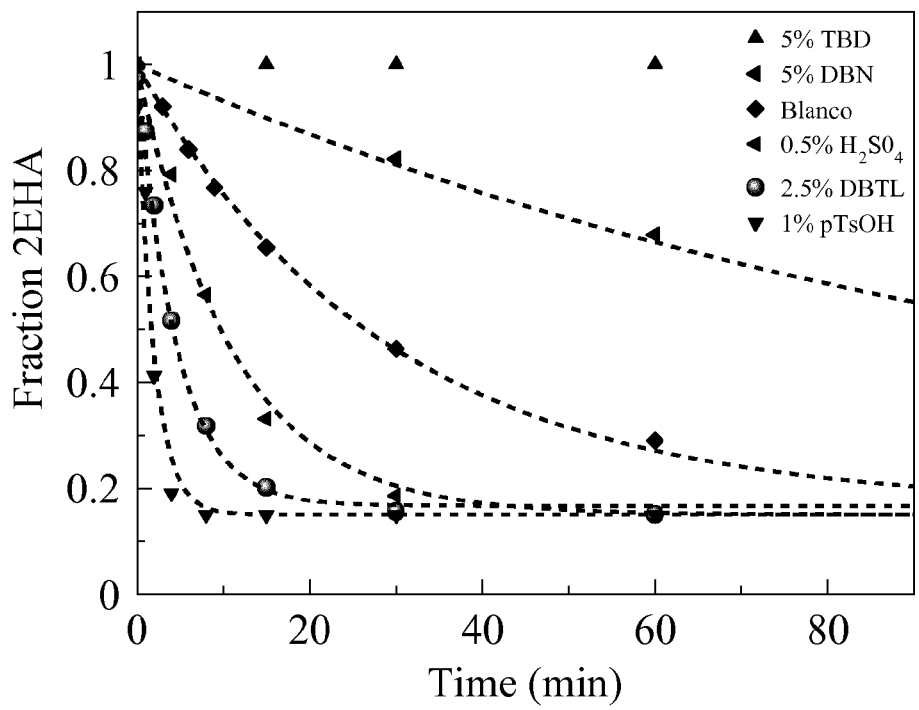
FIG. 19 represents a graph plotting the fraction of 2-ethyl hexyl amine (2EHA) as a function of the reaction time, without catalyst and in the presence of a catalyst.

The resulting mixture was heated at 100° C. At specified time intervals, samples (about 10 mg) were taken and immediately diluted in dichloromethane. The ratio of 2-ethylhexyl amine (3.41 min) and octyl amine (3.67 min) was analyzed using GC. GC was performed on an Agilent 7890A system equipped with a VWR Carrier-160 hydrogen generator and an Agilent HP-5 column of 30 m length and 0.320 mm diameter. A FID detector was used and the inlet was set to 250° C. with a split injection of ratio 25:1. Hydrogen was used as carrier gas at a flow rate of 2 mL/min. The oven temperature was increased with 20° C./min from 50° C. to 120° C., followed by a ramp of 50° C./min. to 300° C. The mole fraction of 2-ethyl hexyl amine was plotted versus time. The results are shown in FIG. 19.

Example 6 Synthesis of Polymers

Example 6.1: Low Tg Vinylogous Urethane Networks

Synthesis of Acetoacetylation of Pripol 2033 (Scheme 10)

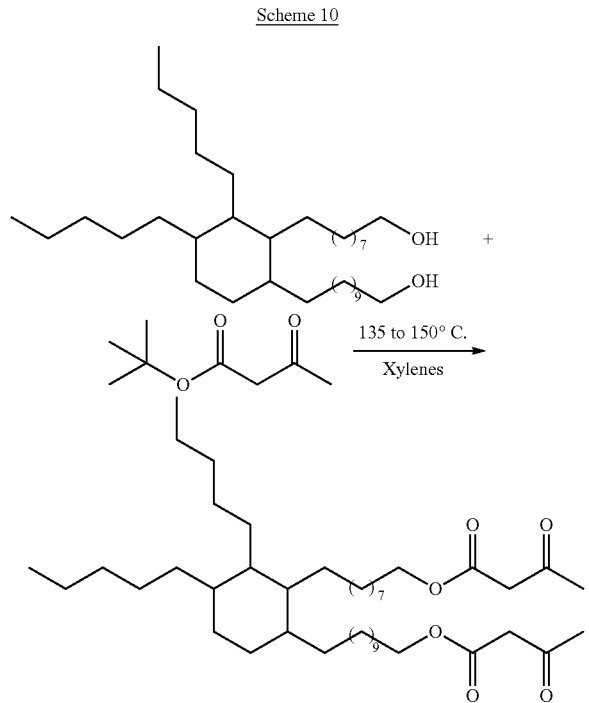

Pripol 2033 (10.0 g, 1 eq) and tert-butyl acetoacetate (6.71 g, 2.3 eq) were dissolved in 8.5 mL xylene and 5.5 mL hexane. The mixture was heated to 135° C. in a distillate set-up until the temperature of the vapor dropped below 63° C. Then the heat was turned up to 150° C. until no more solvent was transferred in the receiving flask. The remainder of the solvent was removed under high vacuum from 80° C. to 100° C., yielding the desired product (PAA). No further purification was required.

Yield: 97%, $^1$H NMR (300 MHz, CDCl$_3$): δ (ppm)=0.79 (m, 6H, CH$_3$CH$_2$—), 1.19 (m, CH$_2$), 1.57 (m, 4H, —CH$_2$CH(CH$_2$)$_2$—), 2.20 (s, 6H, CH$_3$(CO)—), 3.38 (s, 6H, —(CO)CH$_2$(CO)—), 4.06 (t, 4H, —CH$_2$CH$_2$O—)

Synthesis of Polymers: Low Tg Vinylogous Urethane Networks

Priamine 1074, Tris(2-aminoethyl)amine (TREN) and acetoacetylated pripol (PAA) were weighed in a vial in the given sequence (Table 4) resulting in a biphasic system, which was then manually mixed until a homogeneous mixture was obtained. The resulting mixture was poured on a Teflon sheet and manually spread to thickness of around 1 mm and heated for 6 h at 90° C. yielding a yellowish transparent rubbery material. These rubbers were cut in pieces and compression moulded for 30 minutes at 150° C. to defect-free samples of (40.0×70.0×1.3) mm$^3$ from which samples with the desired dimensions for DMTA and tensile tests were cut out. The properties of the obtained compositions are shown in Table 5.

TABLE 4

Used equivalents for stoichiometry screening

| N(priamine) (eq) | 0 | 0.20 | 0.40 | 0.60 | 0.80 |
|---|---|---|---|---|---|
| N(TREN) (eq) | 0.67 | 0.53 | 0.40 | 0.27 | 0.13 |
| N(PAA) | 0.95 | 0.95 | 0.95 | 0.95 | 0.95 |

TABLE 5

Properties of soft vinylogous urethane networks obtained different compositions

| Equivalent Priamine | $T_g$ (° C.) | E' (MPa)$^a$ at 150° C. | Young modulus E (MPa)$^b$ | Yield Stress (MPa)$^b$ |
|---|---|---|---|---|
| 0 | −9 | 3.88 | 3.34 | 2.85 |
| 0.2 | −20 | 3.27 | 2.35 | 1.55 |
| 0.4 | −25 | 2.22 | 1.99 | 1.17 |
| 0.6 | −30 | 1.47 | 1.15 | 0.79 |
| 0.8 | −33.16 | 1.14 | 0.66 | 0.56 |

$^a$measured via DMA, at 150° C.
$^b$measured via tensile testing, at room temperature Low Tg Vinylogous Urethane Network: Effect of the Presence of a Catalyst The catalyst, Priamine 1074, Tris(2-aminoethyl)amine (TREN) and acetoacetylated pripol (PAA) were weighed in a vial in the given sequence (Table 6) resulting in a biphasic system, which was then manually mixed until a homogeneous mixture was obtained. The resulting mixture was poured on a Teflon sheet, manually spread to a thickness of around 1 mm and cured for 6 h at 90° C. yielding transparent, yellowish rubbery materials. These rubbers were cut in pieces and compression moulded for 30 minutes at 150° C. to defect-free samples of (40.0×70.0×1.3) mm$^3$ from which disk shape samples with a diameter of 26 mm were cut out. These disk-shaped samples were used for stress-relaxation experiments. The time measured to decrease a stress, which resulted from a controlled deformation, is measured over time and gives an indication of the processability of the material. The shorter the relaxation time, the faster the processing.

For Brondsted acids, equivalents were calculated versus the amount of free amines: pTsOH (10%): 0.0383 g, H$_2$SO$_4$ (5%): 0.011 g For The Lewis acids, amounts are calculated versus acetoacetate moieties: DBTL (2.5%, 1.2 m %): 0.267 g, DBTL (5%, 2.4 m %): 0.534 g TBD was incorporated via swelling. Catalyst-free disk shape samples were swollen during 15 minutes in dichloromethane in which 14.6 mg/mL TBD was dissolved. The swollen samples were dried at 40° C. in vacuo overnight.

TABLE 6

Used equivalents and amounts for rheologic measurements

| Reagentia | Eq | N (mol) | MW (g/mol) | M (g) |
|---|---|---|---|---|
| Pripol AA | 0.95 | 0.0211 | 710 | 15 g |
| TREN | 0.4 | 0.0089 | 146.23 | 1.3 |
| Priamine | 0.4 | 0.0089 | 547 | 4.8658 |

Stress-relaxation experiments were conducted on an Anton-Paar physica MRC 301 rheometer with a plate geometry of 25 mm and a strain of 5%. The time needed to decrease the initial stress, which resulted from the 5% deformation, to 1/e is given in table 7.

TABLE 7

| Catalyst | Relaxation time at 140° C. (s) |
| --- | --- |
| 10% TBD | 7689 |
| Uncatalyzed | 140 |
| 5% $H_2SO_4$ | 103 |
| 2.4 m % DBTL | 100 |
| 10% pTsOH | 38 |

In accordance with the results obtained on low molecular weight model compounds (example 5), Bronstedt and Lewis acids decreased the relaxation times while a base increased the relaxation time.

Example 6.2: Vinylogous Urea Networks

Synthesis of N,N'-(1,4-phenylene)bis(3-oxobutanamide) (Phenylene diam AA) (Scheme 11)

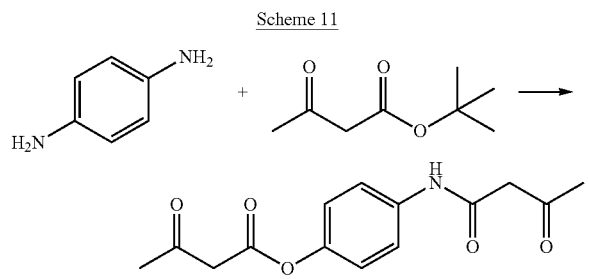

Scheme 11

A solution of tert-butyl acetoacetate (21.0 mmol, 3.38 g) in xylenes (50 mL) was heated to 140° C. (internal temperature) under magnetic stirring. After 10 minutes, a solution of 1,4-phenylene diamine (10 mmol) in xylenes (100 mL) was added dropwise using an addition funnel over a time course of 10 min. After addition, stirring was continued for 1 hour at 140° C. (internal temperature). Afterwards, the bulk xylenes were removed in vacuo affording a pale yellow precipitate. The solids were then redissolved in ethyl acetate (50 mL) and hexane was added dropwise until the solution started to become cloudy. At this point, the solution was left at room temperature for a minimum of 12 hours. The formed white solids were filtered off and dried in vacuo (40° C.) yielding the pure bisacetoacetamide.

Yield: 50%, $^1$H NMR [(DMSO-d6), 300 MHz]: 10.80 (s, 2H, NH), 7.50 (s, 4H, phenyl protons), 3.55 (s, 4H, COCH$_2$CO), 2.22 (s, 6H, COCH$_3$).

Synthesis of 1,1'-(piperazine-1,4-diyl)bis(butane-1,3-dione) (Piperazine Aam)

1,1'-(piperazine-1,4-diyl)bis(butane-1,3-dione) was prepared using the procedure described in Trumbo, D. L. *Polymer Bulletin* 1991, 26 (5), 481-485.

Composition 1:

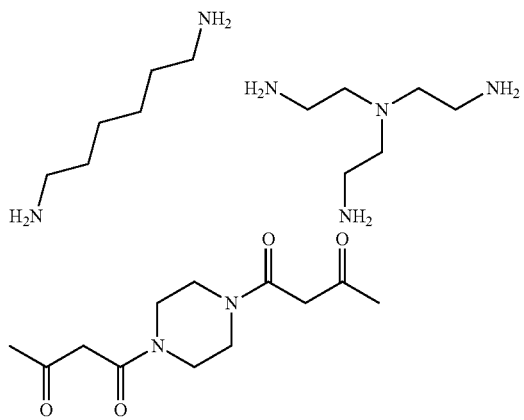

Figure 20:
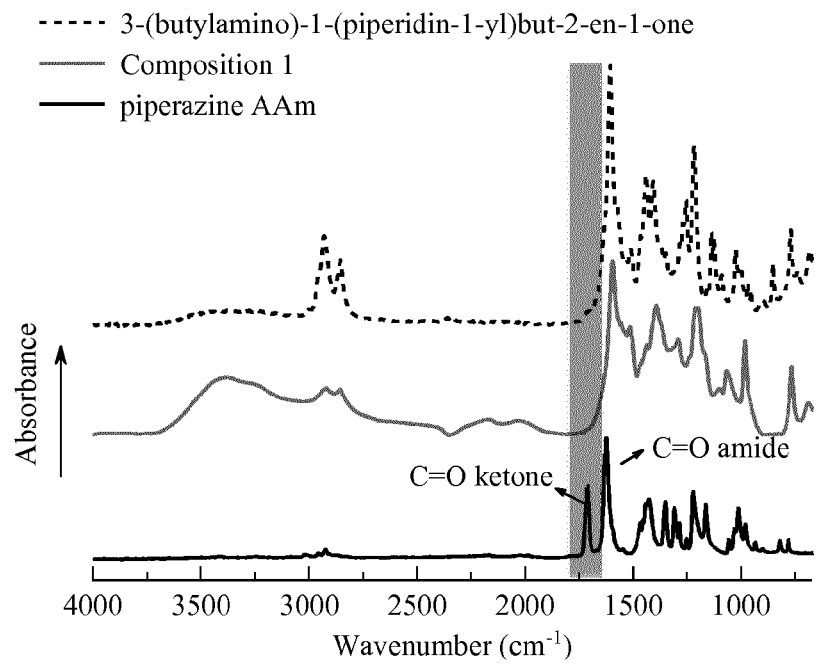
FIG. 20 represents the FTIR spectra of 3-(butylamino)-1-(piperidin-1-yl)but-2-en-1-one, piperazine AAm, and composition 1 prepared in example 6.2.

1,6-Hexane diamine (1.824 g, 16.6 mmol) and TREN (2.241 g; 16.6 mmol,) were weighed in a vial, heated in an oil bath to 80° C. and 1,1'-(piperazine-1,4-diyl)bis(butane-1,3-dione)) (also referred as Piperazine Aam) (10.0 g; 39.3 mmol) was added in bulk while manually stirring. When a fully homogenous mixture was obtained, the mixture was poured on a Teflon sheet and cured for 3 h in vacuo at 150° C. yielding a hard glassy yellowish polymer. The conversion of acetoacetamide groups to the corresponding vinylogous urea was confirmed via IR by the disappearance of the C=O signal at 1711 cm$^{-1}$ (FIG. 20) in good agreement with the IR spectrum of the corresponding model compound, i.e. 3-(butylamino)-1-(piperidin-1-yl)but-2-en-1-one.

The obtained, fully cured network was ground to a fine powder and mold pressed for 15 min at 150° C. after which a homogeneous, defect-free sample was obtained that was used for further characterization.

Compositions 2-6:

Compositions 2 to 6 were prepared as described above for composition 1, with the reagents as listed in Table 8.

TABLE 8

| Composition | Reagent | Molecular weight | eq. | moles | mass (g) |
| --- | --- | --- | --- | --- | --- |
| 1 | Piperazine Aam | 254.29 | 0.95 | 0.039 | 10.00 |
|   | TREN | 146.24 | 0.40 | 0.017 | 2.42 |
|   | hexane diamine | 116.21 | 0.40 | 0.017 | 1.92 |
| 2 | Piperazine Aam | 254.29 | 0.95 | 0.039 | 10.00 |
|   | TREN | 146.24 | 0.40 | 0.017 | 2.42 |
|   | hexane diamine | 116.21 | 0.40 | 0.017 | 1.92 |
|   | pTsOH | 172.2 | 0.01 | 0.0004 | 0.07 |
| 3 | Piperazine Aam | 254.29 | 0.95 | 0.039 | 10.00 |
|   | TREN | 146.24 | 0.40 | 0.017 | 2.42 |
|   | Xylylene diamine | 136.2 | 0.40 | 0.017 | 2.25 |
| 4 | Piperazine Aam | 254.29 | 0.95 | 0.039 | 10.00 |
|   | TREN | 146.24 | 0.40 | 0.017 | 2.42 |
|   | Xylylene diamine | 136.2 | 0.40 | 0.017 | 2.25 |
|   | pTsOH | 172.2 | 0.01 | 0.0004 | 0.07 |
| 5 | ethylene diamine Aam | 228.25 | 0.95 | 0.0438 | 10.00 |
|   | TREN | 146.24 | 0.40 | 0.0184 | 2.70 |
|   | hexane diamine | 116.21 | 0.40 | 0.0184 | 2.14 |
|   | DMF |   |   |   | 5.00 |
| 6 | Phenylene diam AA | 276.29 | 0.95 | 0.0163 | 4.50 |
|   | TREN | 146.24 | 0.40 | 0.0069 | 1.00 |
|   | hexane diamine | 116.21 | 0.40 | 0.0069 | 0.80 |
|   | DMF |   |   |   | 4.00 |

The temperature of 5% mass loss was determined using TGA, Tg via DSC and Modulus (E') and Yield stress via tensile tests as specified in the methods section. The results are shown in Table 9.

TABLE 9

| Composition | Td (95%) | Tg (° C.) | E' (GPa) | Yield stress (Mpa) |
|---|---|---|---|---|
| 1 | 293 | 116 | 2.1 | 61 |
| 2 | 268 | 118 | 2.1 | 74 |
| 3 | 281 | 134 | 2.9 | 100 |
| 4 | 287 | 127 | 2.9 | 74 |
| 5 | 200 | 102 | — | — |
| 6 | 234 | 134 | — | — |

Frequency sweep experiments were conducted on composition 1 and 2. The results are shown in Table 10.

TABLE 10

| Composition | Temperature (° C.) | ω intersection G' and G" (rad s$^{-1}$) | Relaxation time (s) |
|---|---|---|---|
| 1 | 150 | 0.0029 | 336 |
| 1 | 160 | 0.0072 | 138 |
| 1 | 170 | 0.0130 | 76 |
| 1 | 180 | 0.0156 | 64 |
| 2 | 140 | 0.072 | 13.9 |
| 2 | 150 | 0.135 | 7.4 |
| 2 | 160 | 0.201 | 5.0 |
| 2 | 170 | 0.327 | 3.1 |
| 2 | 180 | 0.424 | 2.4 |

Example 6.3: Vinylogous Amide Networks

Synthesis of 1,1'-(1,4-phenylene)bis(3-phenylprop-2-yn-1-one)

a) 1,1'-(1,4-phenylene)bis(3-phenylprop-2-yn-1-ol) (Scheme 12)

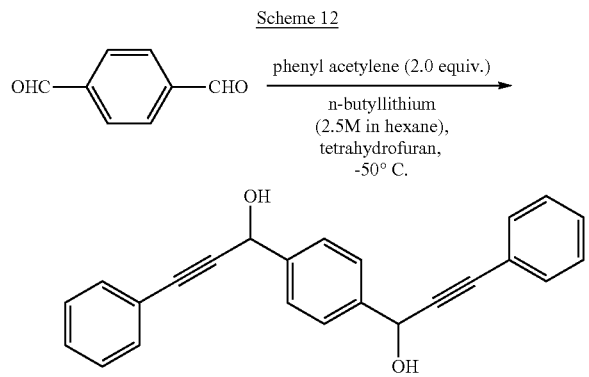

Scheme 12

A solution of phenyl acetylene (11.2 mL, 100 mmol) in anhydrous tetrahydrofuran was first cooled down to −50° C. while maintaining under inert atmosphere, To this solution, a solution of n-butyllithium in hexanes (2.5 M, 40 mL, 100 mmol) was added dropwise over a period of 10 minutes. After stirring the resulting mixture for 5 more minutes, a solution of terephthalaldehyde (6.5 g, 47.6 mmol) in anhydrous tetrahydrofuran (100 mL) was added while keeping the solution temperature at −50° C. Stirring was continued for 1 hour with the temperature steadily increasing to 0° C. After one hour the reaction was worked up with an aqueous saturated ammonium chloride solution (50 mL) dissolving again all solids. Then, the bulk tetrahydrofuran was removed in vacuo and the obtained aqueous phase was combined with diethylether (400 mL). The organic phase was separated, washed with brine (10 mL), dried over magnesium sulphate, filtered over a pad of cotton and concentrated under reduced pressure giving 1,1'-(1,4-phenylene)bis(3-phenylprop-2-yn-1-ol) as a white precipitate (13.82 g, 86%).

$^1$H-NMR (300 MHz, CDCl$_3$) δ=7.68 (s (br.), 4H, CH$_{Ar, centre}$), 7.52-7.47 (band, 4H, CH$_{Ar, meta}$), 7.37-7.32 (band, 6H, CH$_{Ar, ortho+para}$) ppm.

b) 1,1'-(1,4-phenylene)bis(3-phenylprop-2-yn-1-one) (Scheme 13)

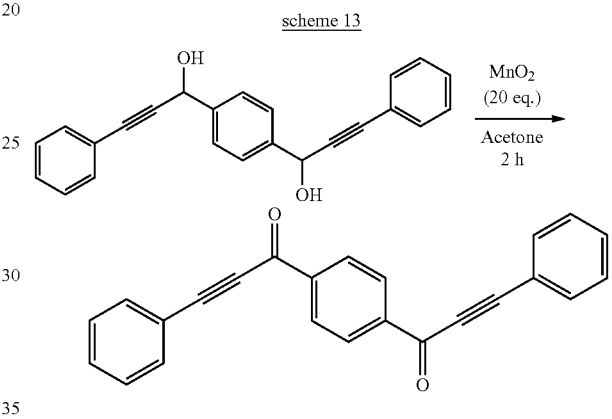

scheme 13

To a solution of 1,1'-(1,4-phenylene)bis(3-phenylprop-2-yn-1-ol) (13.82 g, 40.9 mmol, 1.0 equiv.) in acetone (400 mL) was added all at once solid manganese(IV) oxide (57.6 g, 818 mmol, 20 equiv.) while maintaining room temperature. After full conversion, the solids were filtered off over a pad of magnesium sulphate (50 g) and rinsed thoroughly with boiling acetone (10×150 mL). This step was repeated until all product was extracted out of the magnesium cake. Then, the collected organic phase was evaporated in vacuo giving a pastel yellow precipitate (8.615 g, 63%).

$^1$H-NMR (300 MHz, CDCl$_3$) δ=8.38 (s, 4H, CH$_{Ar, centre}$), 7.77-7.72 (band, 4H, CH$_{Ar, meta}$), 7.56-7.44 (band, 6H, CH$_{Ar, ortho+para}$) ppm.

$^{13}$C-NMR (100 MHZ, CDCl$_3$) δ=177.1 (C=O), 140.5 (C), 133.2 (CH), 131.2 (CH), 129.7 (CH), 128.8 (CH), 119.8 (C), 94.6 (C), 86.9 (C) ppm.

HSQC: 8.38×129.7, 7.77-7.72×133.2, 7.56-7.44×131.2, 7.56-7.44×128.8

Synthesis of Polymers: Vinylogous Amide Networks

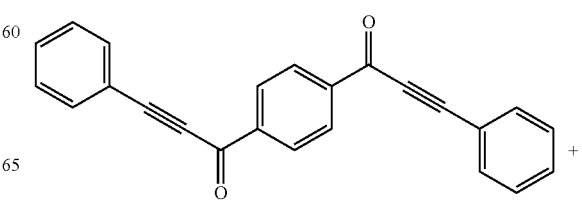

-continued

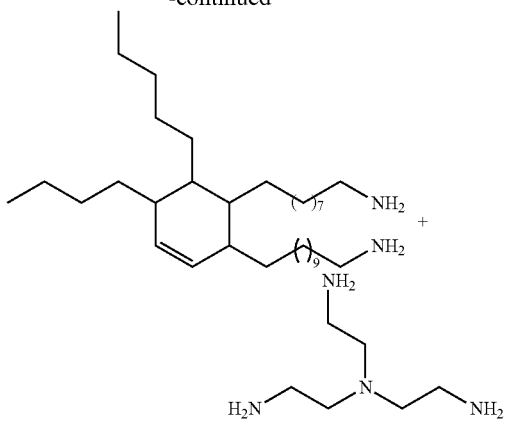

Figure 21:
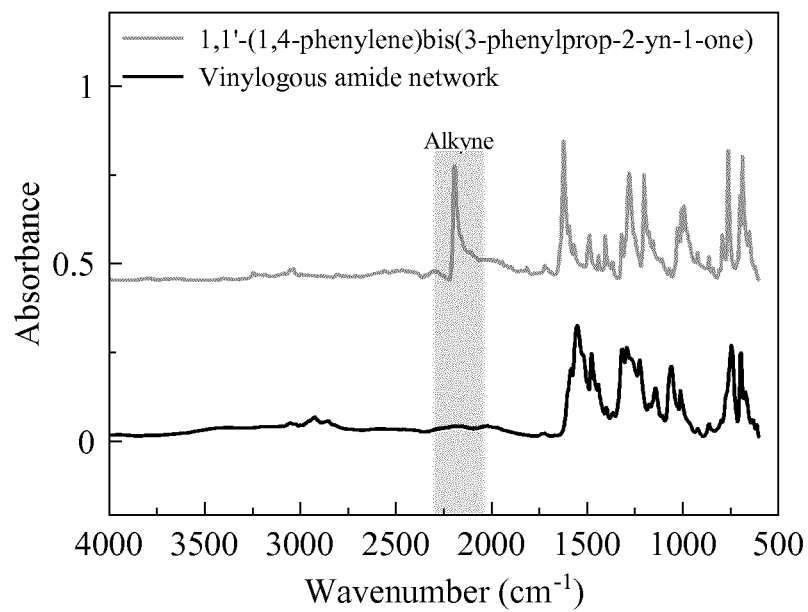
FIG. 21 represents the FTIR spectra of 1,1'-(1,4-phenylene)bis(3-phenylprop-2-yn-1-one), and vinylogous amide network prepared in example 6.3.

1,1'-(1,4-phenylene)bis(3-phenylprop-2-yn-1-one) (15 mmol, 5 g) was dissolved in 50 mL dichloromethane and priamine 1074 (6.3 mmol, 2,413 g) was added. The mixture was stirred for 2 h at room temperature. The solvent was removed in vacuo resulting in a viscous dark green paste. Next, TREN (6.3 mmol, 0.921 g) was added, the mixture was manually stirred until a homogeneous mixture was obtained and transferred to a mould and cured for 2 h at 150° C. Complete disappearance of the alkyne bond at 1291 cm$^{-1}$ was observed (FIG. 21). The obtained material showed a Tg of 56° C. on DSC ($2^{nd}$ heating), a modulus of 1 GPa and a yield stress of 27 MPa according to tensile tests.

The invention claimed is:
1. A composition comprising a polymeric network having at least one unit of formula (I), (II), and/or (III);

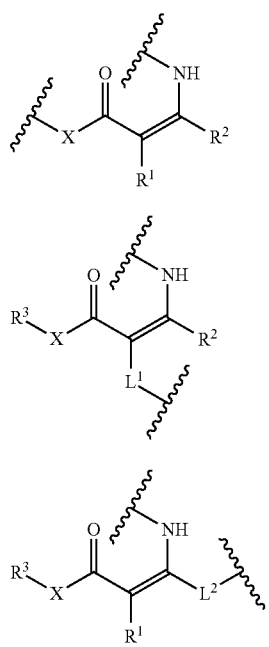

wherein said composition is obtained by contacting at least one compound A comprising at least two functions selected from the group of function of formula —X—C(=O)—CHR$^1$—C(=O)—R$^2$, —C(=O)—C≡C—R$^2$; or —C(=O)—CR$^1$=CR$^2$—NR$^4$R$^5$; wherein at least 25% by weight of compounds A have a functionality ≤5, with % by weight relative to the total weight of compounds A;

with at least one compound B comprising at least one —NH$_2$, or —NH$_3^+$ groups, or at least one functional group that generates —NH$_2$ or —NH$_3^+$ in situ;

wherein the ratio R=(sum(functionality of compound A×number of moles of compound A))/(sum(functionality of compound B×number of moles of all compound B)) is <1;

$$\frac{\sum f_a N_a}{\sum f_b N_b} = R < 1$$

wherein $f_a N_a$ denotes the number of moles of —X—C(=O)—CHR$^1$—C(=O)—R$^2$, —C(=O)—C≡C—R$^2$; or —C(=O)—CR$^1$=CR$^2$—NR$^4$R$^5$ functions of the at least one compound A, and $f_b N_b$ denotes the number of moles of —NH$_2$, and/or —NH$_3^+$ groups or the number of moles of functional groups which could generate —NH$_2$ or NH$_3^+$ in situ, of the at least one compound B;

R$^1$ is hydrogen or is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkyl C$_{1-20}$alkyl; heteroC$_{1-20}$alkyl; heterocyclyl; heterocyclylC$_{1-20}$alkyl; heteroaryl; and heteroarylC$_{1-20}$alkyl; wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be oxidized to form at least one C=O, C=S, N=O, N=S, S=O or S(O)$_2$;

wherein said C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; and heteroarylC$_{1-20}$alkyl; can be unsubstituted or substituted with one or more Z$^1$; each Z$^1$ is independently selected from the group consisting of halogen; C$_{1-20}$alkyl; C$_{2-20}$alkenyl, C$_{2-20}$alkynyl, C$_{6-12}$aryl, C$_{3-8}$cycloalkyl, C$_{6-12}$arylC$_{1-20}$alkyl, heteroC$_{1-20}$alkyl; heterocyclyl; heteroaryl; C$_{3-8}$cycloalkylC$_{1-20}$alkyl; heterocyclylC$_{1-20}$alkyl; heteroarylC$_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$; and R$^4$ is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkylC$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^4$; each $Z^4$ is independently selected from the group consisting of $NR^{11}R^{12}$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; cyano; —$CO_2R^{10}$; —$C(O)NR^{11}R^{12}$; and —$C(O)R^9$;

or wherein the ratio R=(sum(functionality of compound A×number of moles of compound A ))/(sum(functionality of compound A×number of moles of compound A)+sum(functionality of compound B×number of moles of all compound B)) is <1;

$$\frac{\sum f_a N_a}{\sum f_a N_a + \sum f_b N_b} = R < 1$$

when $R^1$ and $R^4$ together with the atom to which they are attached form a 5-, 6-, or 7-membered heterocyclyl or heteroaryl; wherein each of said heterocyclyl; or heteroaryl; can be unsubstituted or substituted with one or more $Z^5$; each $Z^5$ is independently selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halogen; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; $C(O)NR^{11}R^{12}$; and —$C(O)R^9$;

wherein $f_a N_a$ denotes the number of moles of —X—C(=O)—CHR$^1$—C(=O)—R$^2$, —C(=O)—C≡C—R$^2$; or —C(=O)—CR$^1$=CR$^2$—NR$^4$R$^5$ functions of the at least one compound A, and $f_b N_b$ denotes the number of moles of —$NH_2$, and/or —$NH_3^+$ groups or the number of moles of functional groups which could generate —$NH_2$ or $NH_3^+$ in situ of the at least one compound B; and wherein X is selected from O, $NR^{13}$, or $CR^{14}R^{15}$; or X and $R^3$ together form a group $R^6$, wherein $R^6$ is selected from the group consisting of $C_{6-12}$aryl, heteroaryl or heterocyclyl; wherein said $C_{6-12}$aryl, heteroaryl or heterocyclyl can be unsubstituted or substituted with one or more $Z^{31}$; and $Z^{31}$ is independently selected from the group consisting of —C(=O)—C≡C—R$^2$; —X—C(=O)—CHR$^1$—C(=O)—R$^2$, or —C(=O)—CR$^1$=CR$^2$—NR$^4$R$^5$;

halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; $SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$; or $R^3$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl$C_{1-20}$alkyl; $C_{1-20}$alkylheterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; $C_{1-20}$alkylheterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl$C_{1-20}$alkyl; $C_{1-20}$alkylheterocyclyl$C_{1-20}$alkyl; heteroaryl; and heteroaryl$C_{1-20}$alkyl; can be oxidized to form at least one C=O, C=S, N=O, N=S, S=O or $S(O)_2$;

wherein said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl$C_{1-20}$alkyl; $C_{1-20}$alkylheterocyclyl$C_{1-20}$alkyl; heteroaryl; and heteroaryl$C_{1-20}$alkyl; can be unsubstituted or substituted with one or more $Z^3$; each $Z^3$ is independently selected from the group consisting of —X—C(=O)—CHR$^1$—C(=O)—R$^2$, —C(=O)—C≡C—R$^2$; or —C(=O)—CR$^1$=CR$^2$—NR$^4$R$^5$; halogen; $C_{1-20}$alkyl; halo$C_{1-20}$alkyl; halo$C_{1-20}$alkyloxy; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; —$OR^{10}$; —$SR^{10}$; —$S(O)R^9$; —$S(O)_2R^9$; —$SO_2NR^{11}R^{12}$; nitro; —$NR^{10}C(O)R^9$; $NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$L^1$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene;

wherein said $C_{1-20}$alkylene, $C_{2-20}$alkenylene, $C_{2-20}$alkynylene, $C_{3-8}$cycloalkylene$C_{1-20}$alkylene; $C_{6-12}$aryl$C_{1-20}$alkylene, heterocyclylene$C_{1-20}$alkylene; and heteroarylene$C_{1-20}$alkylene, optionally comprises one or more heteroatoms in the alkylene, alkenylene, alkynylene moiety, said heteroatoms being each independently selected from O, S and N;

wherein at least one carbon atom or heteroatom of said $C_{1-20}$alkylene, $C_{2-20}$alkenylene; $C_{2-20}$alkynylene; $C_{6-12}$arylene, $C_{3-8}$cycloalkylene; $C_{6-12}$arylene $C_{1-20}$alkylene; $C_{3-8}$cycloalkylene$C_{1-20}$alkylene; heteroC$_{1-20}$alkylene; heterocyclylene; heterocyclylene$C_{1-20}$alkylene; heteroarylene; and heteroarylene$C_{1-20}$alkylene; can be oxidized to form at least one C=O, C=S, N=O, N=S, S=O or S(O)$_2$;

wherein said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; heteroC$_{1-20}$alkylene; heterocyclylene; heterocyclylene$C_{1-20}$alkylene; heteroarylene; and heteroarylene$C_{1-20}$alkylene; can be unsubstituted or substituted with one or more $Z^{21}$; each $Z^{21}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

$R^2$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; heteroC$_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_2$-20alkenyl, $C_2$-20alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_2$-20alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or S(O)$_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^2$; each $Z^2$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

$L^2$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; heteroC$_{1-20}$alkylene; heterocyclylene; heterocyclylene$C_{1-20}$alkylene; heteroarylene; and heteroarylene$C_{1-20}$alkylene;

wherein said $C_{1-20}$alkylene, $C_{2-20}$alkenylene, $C_{2-20}$alkynylene, $C_{3-8}$cycloalkylene$C_{1-20}$alkylene; $C_{6-12}$aryl$C_{1-20}$alkylene, heterocyclylene$C_{1-20}$alkylene; and heteroarylene$C_{1-20}$alkylene, optionally comprises one or more heteroatoms in the alkylene, alkenylene, alkynylene moiety, said heteroatoms being each independently selected from O, S and N;

wherein at least one carbon atom or heteroatom of said $C_{1-20}$alkylene, $C_{2-20}$alkenylene; $C_{2-20}$alkynylene; $C_{6-12}$arylene, $C_{3-8}$cycloalkylene; $C_{6-12}$arylene $C_{1-20}$alkylene; $C_{3-8}$cycloalkylene$C_{1-20}$alkylene; heteroC$_{1-20}$alkylene; heterocyclylene; heterocyclylene$C_{1-20}$alkylene; heteroarylene; and heteroarylene$C_{1-20}$alkylene; can be oxidized to form at least one C=O, C=S, N=O, N=S, S=O or S(O)$_2$;

wherein said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$ alkylene; heteroC$_{1-20}$alkylene; heterocyclylene; heterocyclylene$C_{1-20}$alkylene; heteroarylene; and heteroarylene$C_{1-20}$alkylene; can be unsubstituted or substituted with one or more $Z^{22}$; each $Z^{22}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

or wherein $R^2$ and $R^4$ together with the atom to which they are attached form a 5-, 6-, or 7-membered heterocyclyl or heteroaryl; wherein each of said heterocyclyl; or heteroaryl; can be unsubstituted or substituted with one or more $Z^6$; each $Z^6$ is independently selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halogen; haloC$_{1-20}$alkyl; haloC$_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$;

$R^5$ is hydrogen or is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl $C_{1-20}$alkyl; heteroC$_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, heteroC$_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or S(O)$_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^7$; each $Z^7$ is independently selected from the group consisting of $NR^{11}R^{12}$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl $C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; $-OR^{10}$; $-SR^{10}$; $-S(O)R^9$; $-S(O)_2R^9$; $-SO_2NR^{11}R^{12}$; nitro; $-NR^{10}C(O)R^9$; $-NR^{10}S(O)_2R^9$; $-NR^{10}C(O)NR^{11}R^{12}$; cyano; $-CO_2R^{10}$; $-C(O)NR^{11}R^{12}$; and $-C(O)R^9$;

each $R^9$ is independently selected from hydroxyl; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

each $R^{10}$ is independently selected from the group consisting of hydrogen, $C_{1-20}$alkyl, $C_{2-20}$alkenyl, $C_{2-20}$alkynyl, $C_{6-12}$aryl, $C_{3-8}$cycloalkyl, $C_{6-12}$aryl $C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl $C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

or wherein $R^{11}$ and $R^{12}$ together with the atom to which they are attached form a 5-, 6-, or 7-membered heterocyclyl;

$R^{13}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

$R^{14}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

$R^{15}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$.

2. The composition according to claim 1, wherein at least 30% by weight of compounds A have a functionality ≤5.

3. The composition according to claim 1, wherein at least 25% by weight of compounds A have a functionality ≤4.

4. The composition according to claim 1, wherein the ratio (sum(functionality of compound A×number of moles of compound A))/(sum(functionality of compound B×number of moles of all compound B)) is ≥0.90

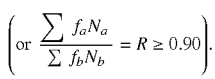

5. The composition according to claim 1, wherein said at least one compound A is a compound of formula (IV); (V); or (VI), or (VII);

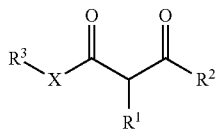

(IV)

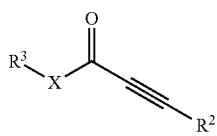

(V)

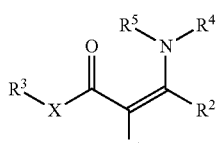

(VI)

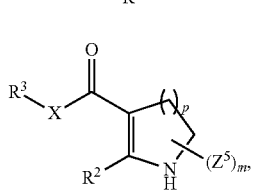

(VII)

wherein m is an integer selected from 0, 1, 2 or 3 and p is an integer selected from 1, 2, or 3.

6. The composition according to claim 1, wherein said at least one compound A is a compound of formula (VIII), (IX), (X), (XI) or (XII);

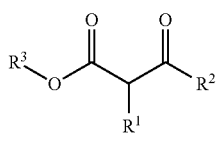

(VIII)

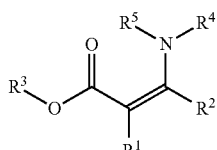

(IX)

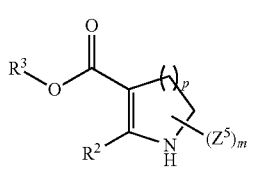

(X)

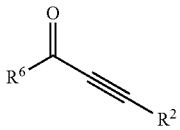

(XI)

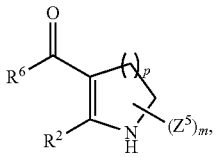

(XII)

wherein m is an integer selected from 0, 1, 2 or 3 and p is an integer selected from 1, 2, or 3.

7. The composition according to claim 1, wherein said at least one compound B comprises at least two groups selected from the group comprising —NH$_2$, and —NH$_3^+$, or at least two functional groups that generate —NH$_2$ or —NH$_3^+$ in situ.

8. The composition according to claim 1, wherein said at least one compound B comprises at least three groups selected from the group comprising —NH$_2$, and —NH$_3^+$, or at least three functional groups that generate —NH$_2$ or —NH$_3^+$ in situ.

9. A process for preparing a composition according to claim 1 comprising contacting at least one compound A comprising at least two functions selected from the group of function of formula —X—C(=O)—CHR$^1$—C(=O)—R$^2$, —C(=O)—C≡C—R$^2$; or —C(=O)—CR$^1$=CR$^2$—NR$^4$R$^5$; wherein at least 25% by weight of compounds A have a functionality ≤5, with % by weight being relative to the total weight of compounds A;

with at least one compound B comprising at least one —NH$_2$, or —NH$_3^+$ groups, or at least one functional group that generates —NH$_2$ or —NH$_3^+$ in situ;

wherein the ratio R=(sum(functionality of compound A×number of moles of compound A))/(sum(functionality of compound B×number of moles of all compound B)) is <1;

$$\frac{\sum f_a N_a}{\sum f_b N_b} = R < 1$$

wherein $f_a N_a$ denotes the number of moles of —X—C(=O)—CHR$^1$—C(=O)—R$^2$, —C(=O)—C≡C—R$^2$; or —C(=O)—CR$^1$=CR$^2$—NR$^4$R$^5$ functions of the at least one compound A, and $f_b N_b$ denotes the number of moles of —NH$_2$, and/or —NH$_3^+$ groups or the number of moles of functional groups which could generate —NH$_2$ or NH$_3^+$ in situ, of the at least one compound B;

R$^1$ is hydrogen or is selected from the group consisting of C$_{1-20}$alkyl, C$_{2-20}$alkenyl; C$_{2-20}$alkynyl; C$_{6-12}$aryl, C$_{3-8}$cycloalkyl; C$_{6-12}$arylC$_{1-20}$alkyl; C$_{3-8}$cycloalkyl C$_{1-20}$alkyl; heteroC$_{1-20}$alkyl; heterocyclyl; heterocyclylC$_{1-20}$alkyl; heteroaryl; and heteroarylC$_{1-20}$alkyl;

wherein said C$_{1-20}$alkyl, C$_{2-20}$alkenyl, C$_{2-20}$alkynyl, C$_{3-8}$cycloalkylC$_{1-20}$alkyl; C$_{6-12}$arylC$_{1-20}$alkyl, heterocyclylC$_{1-20}$alkyl; and heteroarylC$_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^1$; each $Z^1$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^o1$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$; and $R^4$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^4$; each $Z^4$ is independently selected from the group consisting of $NR^{11}R^{12}$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; cyano; —$CO_2R^{10}$; —$C(O)NR^{11}R^{12}$; and —$C(O)R^9$;

or wherein the ratio R=(sum(functionality of compound A×number of moles of compound A ))/(sum(functionality of compound A×number of moles of compound A)+sum(functionality of compound B×number of moles of all compound B)) is <1;

$$\frac{\sum f_a N_a}{\sum f_a N_a + \sum f_b N_b} = R < 1$$

when $R^1$ and $R^4$ together with the atom to which they are attached form a 5-, 6-, or 7-membered heterocyclyl or heteroaryl; wherein each of said heterocyclyl; or heteroaryl; can be unsubstituted or substituted with one or more $Z^5$; each $Z^5$ is independently selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halogen; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; $C(O)NR^{11}R^{12}$; and —$C(O)R^9$;

wherein X is selected from O, $NR^{13}$, or $CR^{14}R^{15}$;

$R^2$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^2$; each $Z^2$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$;

nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

or wherein $R^2$ and $R^4$ together with the atom to which they are attached form a 5-, 6-, or 7-membered heterocyclyl or heteroaryl; wherein each of said heterocyclyl; or heteroaryl; can be unsubstituted or substituted with one or more $Z^6$; each $Z^6$ is independently selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halogen; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$R^5$ is hydrogen or is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl $C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or S(O)$_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^7$; each $Z^7$ is independently selected from the group consisting of $NR^{11}R^{12}$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; cyano; —$CO_2R^{10}$; —$C(O)NR^{11}R^{12}$; and —$C(O)R^9$;

each $R^9$ is independently selected from hydroxyl; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$;

each $R^{10}$ is independently selected from the group consisting of hydrogen, $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$;

or wherein $R^{11}$ and $R^{12}$ together with the atom to which they are attached form a 5-, 6-, or 7-membered heterocyclyl;

$R^{13}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$;

$R^{14}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$;

$R^{15}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or S(O)$_2$.

10. A compound comprising at least two units and at most 5 units of formula (I), (II), and/or (III);

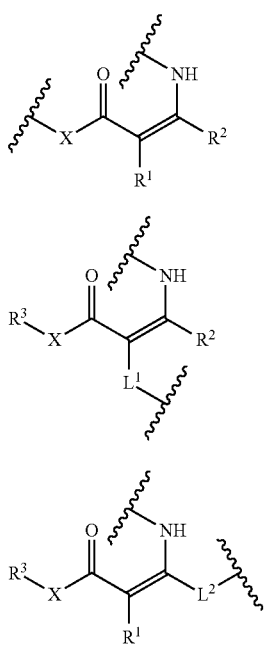

wherein $R^1$ is hydrogen or is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or S(O)$_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^1$; each $Z^1$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$; and X is selected from O, NR$^{13}$, or CR$^{14}$R$^{15}$; or X and R$^3$ together form a group R$^6$, wherein R$^6$ is selected from the group consisting of $C_{6-12}$aryl, heteroaryl or heterocyclyl; wherein said $C_{6-12}$aryl, heteroaryl or heterocyclyl can be unsubstituted or substituted with one or more $Z^{31}$; and $Z^{31}$ is independently selected from the group consisting of —C(=O)—C=C—R$^2$; —X—C(=O)—CHR$^1$—C(=O)—R$^2$, or —C(=O)—CR$^1$=CR$^2$—NR$^4$R$^5$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl $C_{1-20}$alkyl; heteroaryl$C_{1-20}$alkyl; halo$C_{1-20}$alkyl; halo$C_{1-20}$alkyloxy; —OR$^{10}$; SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; and —C(O)R$^9$; or R$^3$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cyclo alkyl; $C_{1-20}$alkyl$C_{6-12}$aryl$C_{1-20}$alkyl; hetero$C_{1-20}$alkyl; heterocyclyl; heterocyclyl$C_{1-20}$alkyl; $C_{1-20}$alkylheterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cyclo alkyl; $C_{1-20}$alkyl$C_{6-12}$aryl$C_{1-20}$alkyl; $C_{1-20}$alkylheterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; $C_{1-20}$alkyl$C_{3-8}$cyclo alkyl$C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl $C_{1-20}$alkyl; $C_{1-20}$alkylheterocyclyl$C_{1-20}$alkyl; heteroaryl; and heteroaryl$C_{1-20}$alkyl; can be oxidized to form at least one C=O, C=S, N=O, N=S, S=O or S(O)$_2$;

wherein said $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; $C_{1-20}$alkyl$C_{3-8}$cycloalkyl$C_{1-20}$alkyl; $C_{3-8}$cycloalkyl$C_{1-20}$alkyl$C_{3-8}$cycloalkyl; $C_{1-20}$alkyl$C_{6-12}$aryl$C_{1-20}$alkyl; hetero$C_{1-20}$alkyl; heterocyclyl; heterocyclyl $C_{1-20}$alkyl; $C_{1-20}$alkylheterocyclyl$C_{1-20}$alkyl; heteroaryl; and heteroaryl$C_{1-20}$alkyl; can be unsubstituted or substituted with one or more $Z^3$; each $Z^3$ is independently selected from the group consisting of —X—C(=O)—CHR$^1$—C(=O)—R$^2$, —C(=O)—C≡C—R$^2$; or —C(=O)—CR$^1$=CR$^2$—NR$^4$R$^5$; halogen; $C_{1-20}$alkyl; halo$C_{1-20}$alkyl; halo$C_{1-20}$alkyloxy; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl;

—$OR^{10}$; —$SR^{10}$; —$S(O)R^9$; —$S(O)_2R^9$; —$SO_2NR^{11}R^{12}$; nitro; —$NR^{10}C(O)R^9$; $NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$L^1$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene;

wherein said $C_{1-20}$alkylene, $C_{2-20}$alkenylene, $C_{2-20}$alkynylene, $C_{3-8}$cycloalkylene$C_{1-20}$alkylene; $C_{6-12}$aryl$C_{1-20}$alkylene, heterocyclylene$C_{1-20}$alkylene; and heteroarylene$C_{1-20}$alkylene, optionally comprises one or more heteroatoms in the alkylene, alkenylene, alkynylene moiety, said heteroatoms being each independently selected from O, S and N;

wherein at least one carbon atom or heteroatom of said $C_{1-20}$alkylene, $C_{2-20}$alkenylene; $C_{2-20}$alkynylene; $C_{6-12}$arylene, $C_{3-8}$cycloalkylene; $C_{6-12}$arylene $C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene; can be oxidized to form at least one $C=O$, $C=S$, $N=O$, $N=S$, $S=O$ or $S(O)_2$;

wherein said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene; can be unsubstituted or substituted with one or more $Z^{21}$; each $Z^{21}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$R^2$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one $C=O$, $C=S$, $N=O$, $N=S$, $S=O$ or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^2$; each $Z^2$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$L^2$ is selected from the group consisting of $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene;

wherein said $C_{1-20}$alkylene, $C_{2-20}$alkenylene, $C_{2-20}$alkynylene, $C_{3-8}$cycloalkylene$C_{1-20}$alkylene; $C_{6-12}$aryl$C_{1-20}$alkylene, heterocyclylene$C_{1-20}$alkylene; and heteroarylene$C_{1-20}$alkylene, optionally comprises one or more heteroatoms in the alkylene, alkenylene, alkynylene moiety, said heteroatoms being each independently selected from O, S and N;

wherein at least one carbon atom or heteroatom of said $C_{1-20}$alkylene, $C_{2-20}$alkenylene; $C_{2-20}$alkynylene; $C_{6-12}$arylene, $C_{3-8}$cycloalkylene; $C_{6-12}$arylene $C_{1-20}$alkylene; $C_{3-8}$cycloalkylene$C_{1-20}$alkylene; hetero$C_{1-20}$alkylene; heterocyclylene; heterocyclylene$C_{1-20}$alkylene; heteroarylene; and heteroarylene$C_{1-20}$alkylene; can be oxidized to form at least one $C=O$, $C=S$, $N=O$, $N=S$, $S=O$ or $S(O)_2$;

wherein said $C_{1-20}$alkylene, $C_{2-20}$alkenylene; $C_{2-20}$alkynylene; $C_{6-12}$arylene, $C_{3-8}$cycloalkylene; $C_{6-12}$arylene$C_{1-20}$alkylene; $C_{3-8}$cycloalkylene$C_{1-20}$ alkylene; hetero$C_{1-20}$alkylene; heterocyclylene; heterocyclylene$C_{1-20}$alkylene; heteroarylene; and heteroarylene$C_{1-20}$alkylene; can be unsubstituted or substituted with one or more $Z^{22}$ each $Z^{22}$ is independently selected from the group consisting of halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; $SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$R^4$ is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl$C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one $C=O$, $C=S$, $N=O$, $N=S$, $S=O$ or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^4$; each $Z^4$ is independently selected from the group consisting of $NR^{11}R^{12}$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl $C_{1-20}$alkyl, hetero$C_{1-20}$alkyl; heterocyclyl; heteroaryl; $C_{3-8}$cycloalkyl$C_{1-20}$alkyl; heterocyclyl $C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; cyano; —$CO_2R^{10}$; —$C(O)NR^{11}R^{12}$; and —$C(O)R^9$;

or $R^1$ and $R^4$ together with the atom to which they are attached form a 5-, 6-, or 7-membered heterocyclyl or heteroaryl; wherein each of said heterocyclyl; or heteroaryl; can be unsubstituted or substituted with one or more $Z^5$; each $Z^5$ is independently selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; heteroaryl$C_{1-20}$alkyl; halogen; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; and —$C(O)R^9$;

$R^5$ is hydrogen or is selected from the group consisting of $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-20}$alkyl; $C_{3-8}$cycloalkyl $C_{1-20}$alkyl; hetero$C_{1-20}$alkyl; heterocyclyl; heterocyclyl$C_{1-20}$alkyl; heteroaryl; and heteroaryl$C_{1-20}$alkyl;

wherein said $C_{1-20}$alkyl, $C_{2-20}$alkenyl, $C_{2-20}$alkynyl, $C_{3-8}$cycloalkyl$C_{1-20}$alkyl; $C_{6-12}$aryl$C_{1-20}$alkyl, heterocyclyl$C_{1-20}$alkyl; and heteroaryl$C_{1-20}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; $C_{3-8}$cycloalkyl$C_{1-20}$alkyl; heterocyclyl$C_{1-20}$alkyl; and heteroaryl$C_{1-20}$alkyl; can be unsubstituted or substituted with one or more $Z^7$; each $Z^7$ is independently selected from the group consisting of $NR^{11}R^{12}$; halogen; $C_{1-20}$alkyl; $C_{2-20}$alkenyl, $C_{2-20}$alkynyl, $C_{6-12}$aryl, $C_{3-8}$cycloalkyl, $C_{6-12}$aryl $C_{1-20}$alkyl, hetero$C_{1-20}$alkyl; heterocyclyl; heteroaryl; $C_{3-8}$cycloalkyl$C_{1-20}$alkyl; heterocyclyl $C_{1-20}$alkyl; heteroaryl$C_{1-20}$alkyl; halo$C_{1-20}$alkyl; halo$C_{1-20}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; cyano; —$CO_2R^{10}$; —$C(O)NR^{11}R^{12}$; and —$C(O)R^9$;

each $R^9$ is independently selected from hydroxyl; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl $C_{1-20}$alkyl; and heteroaryl$C_{1-20}$alkyl; can be oxidized to form at least one C=O, C=S, N=O, N=S, S=O or $S(O)_2$;

each $R^{10}$ is independently selected from the group consisting of hydrogen, $C_{1-20}$alkyl, $C_{2-20}$alkenyl, $C_{2-20}$alkynyl, $C_{6-12}$aryl, $C_{3-8}$cycloalkyl, $C_{6-12}$aryl $C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl $C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

or wherein $R^{11}$ and $R^{12}$ together with the atom to which they are attached form a 5-, 6-, or 7-membered heterocyclyl;

$R^{13}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

$R^{14}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$;

$R^{15}$ is hydrogen or is selected from the group consisting of $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl;

wherein said $C_{1-20}$alkyl, $C_{2-20}$alkenyl, $C_{2-20}$alkynyl, $C_{6-12}$aryl$C_{1-20}$alkyl, heterocyclyl$C_{1-20}$alkyl; heteroaryl$C_{1-20}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-20}$alkyl, hetero$C_{1-20}$alkyl; heterocyclyl; heteroaryl; heterocyclyl$C_{1-20}$alkyl; and heteroaryl$C_{1-20}$alkyl; can be oxidized to form at least one C=O, C=S, N=O, N=S, S=O or $S(O)_2$.

11. A method of preparing a polymeric network comprising providing a composition according to claim 1, and polymerizing said composition.

12. A polymer obtained using a composition according to claim 1.

13. An article comprising the composition according to claim 1.

14. A process for recycling an article according to claim 13, comprising: a) reducing the article into particles by application of mechanical grinding, b) transforming the particles from step a) by applying a mechanical constraint to the particles at a temperature (T) above room temperature.

15. A process for reshaping and/or repairing an article according to claim 13, comprising the step of thermally treating the article at a temperature (T) above room temperature.

16. A method of preparing a polymeric network comprising providing a compound according to claim 10, and polymerizing said compound.

17. A polymer obtained using a composition according to a compound according to claim 10.

18. An article comprising the composition according to a polymer according to claim 12.

* * * * *